(12) United States Patent
Sanghavi et al.

(10) Patent No.: US 12,097,221 B2
(45) Date of Patent: Sep. 24, 2024

(54) PLATELET LYSATE, AND METHOD OF PREPARATION THEREOF

(71) Applicant: REGROW BIOSCIENCES PRIVATE LIMITED, Mumbai (IN)

(72) Inventors: Satyen Sanghavi, Mumbai (IN); Vinayak Kedage, Pune (IN)

(73) Assignee: REGROW BIOSCIENCES PRIVATE LIMITED, Mumbai (IN)

( * ) Notice: Subject to any disclaimer, the term of this patent is extended or adjusted under 35 U.S.C. 154(b) by 638 days.

(21) Appl. No.: 17/428,590

(22) PCT Filed: Feb. 7, 2020

(86) PCT No.: PCT/IN2020/050120
§ 371 (c)(1),
(2) Date: Aug. 4, 2021

(87) PCT Pub. No.: WO2020/161746
PCT Pub. Date: Aug. 13, 2020

(65) Prior Publication Data
US 2022/0184132 A1    Jun. 16, 2022

(30) Foreign Application Priority Data
Feb. 8, 2019    (IN) .............................. 201921005150

(51) Int. Cl.
*A61K 35/19*        (2015.01)
*A61K 35/32*        (2015.01)
(Continued)

(52) U.S. Cl.
CPC .............. *A61K 35/19* (2013.01); *A61K 35/32* (2013.01); *A61K 35/51* (2013.01); *C12N 5/0644* (2013.01);
(Continued)

(58) Field of Classification Search
CPC .................................................. C12N 5/0644
See application file for complete search history.

(56) References Cited

U.S. PATENT DOCUMENTS 9,700,583 B2    7/2017    Centeno et al.
2011/0123503 A1    5/2011    Rebulla et al.

FOREIGN PATENT DOCUMENTS

CA    2 493 795 A1    2/2004
CN    106236779 A    12/2016
(Continued)

OTHER PUBLICATIONS

Shirzad et al., "Umbilical cord platelet lysate as serum substitute in expansion of human mesenchymal stem cells," Cell J 19(3):403-414, 2017.*
(Continued)

*Primary Examiner* — Rosanne Kosson
(74) *Attorney, Agent, or Firm* — Seed IP Law Group LLP

(57) ABSTRACT

The present disclosure discloses a method for preparing a lysate, from a combination of umbilical cord blood (UCB) and maternal blood (MB) derived platelets by obtaining platelet-rich plasma via sedimentation processes and then mixing platelet-rich plasmas so obtained. The present disclosure further discloses a combination of umbilical cord blood and maternal blood platelet lysate (UCB+MB PL), and the PL so obtained shows greater efficacy as cell and tissue culture media supplement over and above its individual components, umbilical cord blood platelet lysate (UCB PL) and maternal blood platelet lysate (MB PL) and especially over foetal bovine serum (FBS). Moreover, the method of the present disclosure provides an economic, environment friendly, ethical and efficacious method to (Continued)

reach a cell and tissue culture supplement with far-reaching therapeutic applications.

18 Claims, 7 Drawing Sheets

Specification includes a Sequence Listing.

(51) Int. Cl.
　　　A61K 35/51　　(2015.01)
　　　C12N 5/0775　　(2010.01)
　　　C12N 5/078　　(2010.01)
(52) U.S. Cl.
　　　CPC ........ *C12N 5/0665* (2013.01); *C12N 2523/00* (2013.01); *C12N 2525/00* (2013.01)

(56) References Cited

FOREIGN PATENT DOCUMENTS

| | | |
|---|---|---|
| CN | 107384856 A | 11/2017 |
| EP | 2 757 879 B1 | 8/2018 |
| WO | 2017/196798 A1 | 11/2017 |

OTHER PUBLICATIONS

Hsu, W.K., et al., "Platelet-rich Plasma in Orthopaedic Applications: Evidence-based Recommendations for Treatment," *J Am Acad Orthop Surg* 21(12):739-748, Dec. 2013.

Bernardi, M., et al., "The Production Method Affects the Efficacy of Platelet Derivatives to Expand Mesenchymal Stromal Cells In Vitro," *Journal of Translational Medicine* 15(90), 2017, 9 pages.

Gannon, T., et al., "The Use of Hydroxy-Ethyl Starch Sedimentation for Autologous Buffy Coat Preparation," *The Journal of the American Society of Extra-Corporeal Technology* 37(3):311-314, 2005.

Gifford, S.C., et al., "A Portable System for Processing Donated Whole Blood Into High Quality Components Without Centrifugation," *PLoS One* 13(1):e0190827, 2018, 20 pages.

Hashemi, S.-S., et al., "The Role of Human Adult Peripheral and Umbilical Cord Blood Platelet-Rich Plasma on Proliferation and Migration of Human Skin Fibroblasts," *World J Plast Surg* 6(2): 198-205, May 2017.

Kandoi, S., et al., "Evaluation of Platelet Lysate as a Substitute for FBS in Explant and Enzymatic Isolation Methods of Human Umbilical Cord MSCs," *Scientific Reports* 8(124239), 2018, 12 pages.

Kummer, H., et al., "Separation of Platelet Rich Plasma and Red Cells With Modified Gelatin," *Vox Sang.* 24:76-88, 1973.

Kwok, Y.K., "Maternal Plasma or Human Serum Albumin in Wash Buffer Enhances Enrichment and Ex Vivo Expansion of Human Umbilical Cord Blood CD34$^+$ Cells," *British Journal of Haematology* 137(5):468-474, 2007.

Mlynarek, R.A., et al., "Platelet-Rich Plasma (PRP) in Orthopedic Sports Medicine," *The American Journal of Orthopedics* 45(4): 290-294, 326, Jul./Aug. 2016.

Murphy, M.B., et al., "Adult and Umbilical Cord Blood-Derived Platelet-Rich Plasma for Mesenchymal Stem Cell Proliferation, Chemotaxis, and Cryo-Preservation," *Biomaterials* 33(21):5308-5316, Jul. 2012.

Padilla, S., et al., "Platelet-Rich Plasma in Orthopaedic Applications: Evidence-Based Recommendations for Treatment," *J Am Acad Orthop Surg.* 22(8):469-470, Aug. 2014.

Shaheen A., "Platelet Rich Plasma (PRP) for Treatment Non-Healing Ulcers: A Review Study," *Austin Journal of Dermatology* 5(1), 2018, 9 pages.

Shirzad, N., et al., "Umbilical Cord Blood Platelet Lysate as Serum Substitute in Expansion of Human Mesenchymal Stem Cells," *Cell Journal* 19(3):403-414, Oct.-Dec. 2017.

\* cited by examiner

SEQUENCE LISTING

```
<160> NUMBER OF SEQ ID NOS: 26

<210> SEQ ID NO 1
<211> LENGTH: 466
<212> TYPE: PRT
<213> ORGANISM: Artificial Sequence
<220> FEATURE:
<223> OTHER INFORMATION: depicts amino acid sequence for Vimentin

<400> SEQUENCE: 1

Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
        50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
            115                 120                 125

Lys Ile Leu Leu Ala Glu Leu Glu Gln Leu Lys Gly Gln Gly Lys Ser
        130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175
```

```
Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465

<210> SEQ ID NO 2
<211> LENGTH: 1338
<212> TYPE: PRT
<213> ORGANISM: Artificial Sequence
<220> FEATURE:
<223> OTHER INFORMATION: depicts amino acid sequence for Vascular
      endothelial growth factor receptor 1

<400> SEQUENCE: 2

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45
```

```
Leu His Leu Gln Cys Arg Gly Glu Ala Ala His Lys Trp Ser Leu Pro
 50                  55                  60
Glu Met Val Ser Lys Glu Ser Glu Arg Leu Ser Ile Thr Lys Ser Ala
 65                  70                  75                  80
Cys Gly Arg Asn Gly Lys Gln Phe Cys Ser Thr Leu Thr Leu Asn Thr
                     85                  90                  95
Ala Gln Ala Asn His Thr Gly Phe Tyr Ser Cys Lys Tyr Leu Ala Val
                    100                 105                 110
Pro Thr Ser Lys Lys Lys Glu Thr Glu Ser Ala Ile Tyr Ile Phe Ile
                115                 120                 125
Ser Asp Thr Gly Arg Pro Phe Val Glu Met Tyr Ser Glu Ile Pro Glu
    130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                    165                 170                 175
Leu Ile Pro Asp Gly Lys Arg Ile Ile Trp Asp Ser Arg Lys Gly Phe
                180                 185                 190
Ile Ile Ser Asn Ala Thr Tyr Lys Glu Ile Gly Leu Leu Thr Cys Glu
            195                 200                 205
Ala Thr Val Asn Gly His Leu Tyr Lys Thr Asn Tyr Leu Thr His Arg
    210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                    245                 250                 255
Pro Leu Asn Thr Arg Val Gln Met Thr Trp Ser Tyr Pro Asp Glu Lys
                260                 265                 270
Asn Lys Arg Ala Ser Val Arg Arg Arg Ile Asp Gln Ser Asn Ser His
            275                 280                 285
Ala Asn Ile Phe Tyr Ser Val Leu Thr Ile Asp Lys Met Gln Asn Lys
    290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                    325                 330                 335
Lys His Arg Lys Gln Gln Val Leu Glu Thr Val Ala Gly Lys Arg Ser
                340                 345                 350
Tyr Arg Leu Ser Met Lys Val Lys Ala Phe Pro Ser Pro Glu Val Val
            355                 360                 365
Trp Leu Lys Asp Gly Leu Pro Ala Thr Glu Lys Ser Ala Arg Tyr Leu
    370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                    405                 410                 415
Asn Leu Thr Ala Thr Leu Ile Val Asn Val Lys Pro Gln Ile Tyr Glu
                420                 425                 430
Lys Ala Val Ser Ser Phe Pro Asp Pro Ala Leu Tyr Pro Leu Gly Ser
            435                 440                 445
Arg Gln Ile Leu Thr Cys Thr Ala Tyr Gly Ile Pro Gln Pro Thr Ile
    450                 455                 460
```

```
Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
            485                 490                 495

Asn Met Gly Asn Arg Ile Glu Ser Ile Thr Gln Arg Met Ala Ile Ile
        500                 505                 510

Glu Gly Lys Asn Lys Met Ala Ser Thr Leu Val Val Ala Asp Ser Arg
    515                 520                 525

Ile Ser Gly Ile Tyr Ile Cys Ile Ala Ser Asn Lys Val Gly Thr Val
530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
            565                 570                 575

Cys Thr Val Asn Lys Phe Leu Tyr Arg Asp Val Thr Trp Ile Leu Leu
        580                 585                 590

Arg Thr Val Asn Asn Arg Thr Met His Tyr Ser Ile Ser Lys Gln Lys
    595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
            645                 650                 655

Asp Gln Glu Ala Pro Tyr Leu Leu Arg Asn Leu Ser Asp His Thr Val
        660                 665                 670

Ala Ile Ser Ser Ser Thr Thr Leu Asp Cys His Ala Asn Gly Val Pro
    675                 680                 685

Glu Pro Gln Ile Thr Trp Phe Lys Asn Asn His Lys Ile Gln Gln Glu
690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
            725                 730                 735

Lys Gly Ser Val Glu Ser Ser Ala Tyr Leu Thr Val Gln Gly Thr Ser
        740                 745                 750

Asp Lys Ser Asn Leu Glu Leu Ile Thr Leu Thr Cys Thr Cys Val Ala
    755                 760                 765

Ala Thr Leu Phe Trp Leu Leu Leu Thr Leu Phe Ile Arg Lys Met Lys
770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
            805                 810                 815

Ala Ser Lys Trp Glu Phe Ala Arg Glu Arg Leu Lys Leu Gly Lys Ser
        820                 825                 830

Leu Gly Arg Gly Ala Phe Gly Lys Val Val Gln Ala Ser Ala Phe Gly
    835                 840                 845

Ile Lys Lys Ser Pro Thr Cys Arg Thr Val Ala Val Lys Met Leu Lys
850                 855                 860

Glu Gly Ala Thr Ala Ser Glu Tyr Lys Ala Leu Met Thr Glu Leu Lys
865                 870                 875                 880
```

```
Ile Leu Thr His Ile Gly His His Leu Asn Val Val Asn Leu Leu Gly
            885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
            915                 920                 925

Phe Leu Asn Lys Asp Ala Ala Leu His Met Glu Pro Lys Lys Glu Lys
            930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
            965                 970                 975

Leu Ser Asp Val Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
            995                 1000                1005

Gly Met Glu Phe Leu Ser Ser Arg Lys Cys Ile His Arg Asp Leu
            1010                1015                1020

Ala Ala Arg Asn Ile Leu Leu Ser Glu Asn Asn Val Val Lys Ile
            1025                1030                1035

Cys Asp Phe Gly Leu Ala Arg Asp Ile Tyr Lys Asn Pro Asp Tyr
            1040                1045                1050

Val Arg Lys Gly Asp Thr Arg Leu Pro Leu Lys Trp Met Ala Pro
            1055                1060                1065

Glu Ser Ile Phe Asp Lys Ile Tyr Ser Thr Lys Ser Asp Val Trp
            1070                1075                1080

Ser Tyr Gly Val Leu Leu Trp Glu Ile Phe Ser Leu Gly Gly Ser
            1085                1090                1095

Pro Tyr Pro Gly Val Gln Met Asp Glu Asp Phe Cys Ser Arg Leu
            1100                1105                1110

Arg Glu Gly Met Arg Met Arg Ala Pro Glu Tyr Ser Thr Pro Glu
            1115                1120                1125

Ile Tyr Gln Ile Met Leu Asp Cys Trp His Arg Asp Pro Lys Glu
            1130                1135                1140

Arg Pro Arg Phe Ala Glu Leu Val Glu Lys Leu Gly Asp Leu Leu
            1145                1150                1155

Gln Ala Asn Val Gln Gln Asp Gly Lys Asp Tyr Ile Pro Ile Asn
            1160                1165                1170

Ala Ile Leu Thr Gly Asn Ser Gly Phe Thr Tyr Ser Thr Pro Ala
            1175                1180                1185

Phe Ser Glu Asp Phe Phe Lys Glu Ser Ile Ser Ala Pro Lys Phe
            1190                1195                1200

Asn Ser Gly Ser Ser Asp Val Arg Tyr Val Asn Ala Phe Lys
            1205                1210                1215

Phe Met Ser Leu Glu Arg Ile Lys Thr Phe Glu Glu Leu Leu Pro
            1220                1225                1230

Asn Ala Thr Ser Met Phe Asp Asp Tyr Gln Gly Asp Ser Ser Thr
            1235                1240                1245

Leu Leu Ala Ser Pro Met Leu Lys Arg Phe Thr Trp Thr Asp Ser
            1250                1255                1260

Lys Pro Lys Ala Ser Leu Lys Ile Asp Leu Arg Val Thr Ser Lys
            1265                1270                1275
```

```
Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 3
<211> LENGTH: 260
<212> TYPE: PRT
<213> ORGANISM: Artificial Sequence
<220> FEATURE:
<223> OTHER INFORMATION: depicts amino acid sequence for Glyceraldehyde-
      3-phosphate dehydrogenase

<400> SEQUENCE: 3

Met Glu Glu Met Arg Asp Pro Ser Lys Ile Lys Trp Gly Asp Ala Gly
1               5                   10                  15

Ala Glu Tyr Val Val Glu Ser Thr Gly Val Phe Thr Thr Met Glu Lys
                20                  25                  30

Ala Gly His Leu Gln Gly Gly Ala Lys Arg Val Ile Ile Ser Ala
            35                  40                  45

Pro Ser Ala Asp Ala Pro Met Phe Val Met Gly Val Asn His Glu Lys
50                  55                  60

Tyr Asp Asn Ser Leu Lys Ile Ile Ser Asn Ala Ser Cys Thr Thr Asn
65                  70                  75                  80

Cys Leu Ala Pro Leu Ala Lys Val Ile His Asp Asn Phe Gly Ile Val
                85                  90                  95

Glu Gly Leu Met Thr Thr Val His Ala Ile Thr Ala Thr Gln Lys Thr
                100                 105                 110

Val Asp Gly Pro Ser Gly Lys Leu Trp Arg Asp Gly Arg Gly Ala Leu
            115                 120                 125

Gln Asn Ile Ile Pro Ala Ser Thr Gly Ala Ala Lys Ala Val Gly Lys
130                 135                 140

Val Ile Pro Glu Leu Asn Gly Lys Leu Thr Gly Met Ala Phe Arg Val
145                 150                 155                 160

Pro Thr Ala Asn Val Ser Val Val Asp Leu Thr Cys Arg Leu Glu Lys
                165                 170                 175

Pro Ala Lys Tyr Asp Asp Ile Lys Lys Val Val Lys Gln Ala Ser Glu
            180                 185                 190

Gly Pro Leu Lys Gly Ile Leu Gly Tyr Thr Glu His Gln Val Val Ser
        195                 200                 205

Ser Asp Phe Asn Ser Asp Thr His Ser Ser Thr Phe Asp Ala Gly Ala
210                 215                 220

Gly Ile Ala Leu Asn Asp His Phe Val Lys Leu Ile Ser Trp Tyr Asp
225                 230                 235                 240

Asn Glu Phe Gly Tyr Ser Asn Arg Val Val Asp Leu Met Ala His Met
                245                 250                 255

Ala Ser Lys Glu
            260

<210> SEQ ID NO 4
<211> LENGTH: 531
<212> TYPE: PRT
<213> ORGANISM: Artificial Sequence
```

<220> FEATURE:
<223> OTHER INFORMATION: depicts amino acid sequence for Pyruvate kinase

<400> SEQUENCE: 4

```
Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
        355                 360                 365

Asp Tyr Pro Leu Glu Ala Val Arg Met Gln His Leu Ile Ala Arg Glu
    370                 375                 380

Ala Glu Ala Ala Ile Tyr His Leu Gln Leu Phe Glu Glu Leu Arg Arg
385                 390                 395                 400
```

Leu Ala Pro Ile Thr Ser Asp Pro Thr Glu Ala Thr Ala Val Gly Ala
            405                 410                 415

Val Glu Ala Ser Phe Lys Cys Cys Ser Gly Ala Ile Ile Val Leu Thr
            420                 425                 430

Lys Ser Gly Arg Ser Ala His Gln Val Ala Arg Tyr Arg Pro Arg Ala
            435                 440                 445

Pro Ile Ile Ala Val Thr Arg Asn Pro Gln Thr Ala Arg Gln Ala His
        450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
                485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
            515                 520                 525

Pro Val Pro
        530

<210> SEQ ID NO 5
<211> LENGTH: 268
<212> TYPE: PRT
<213> ORGANISM: Artificial Sequence
<220> FEATURE:
<223> OTHER INFORMATION: depicts amino acid sequence for Mesoderm
      posterior protein 1

<400> SEQUENCE: 5

Met Ala Gln Pro Leu Cys Pro Pro Leu Ser Glu Ser Trp Met Leu Ser
1               5                   10                  15

Ala Ala Trp Gly Pro Thr Arg Arg Pro Pro Ser Asp Lys Asp Cys
            20                  25                  30

Gly Arg Ser Leu Val Ser Ser Pro Asp Ser Trp Gly Ser Thr Pro Ala
            35                  40                  45

Asp Ser Pro Val Ala Ser Pro Ala Arg Pro Gly Thr Leu Arg Asp Pro
        50                  55                  60

Arg Ala Pro Ser Val Gly Arg Arg Gly Ala Arg Ser Ser Arg Leu Gly
65                  70                  75                  80

Ser Gly Gln Arg Gln Ser Ala Ser Glu Arg Glu Lys Leu Arg Met Arg
            85                  90                  95

Thr Leu Ala Arg Ala Leu His Glu Leu Arg Arg Phe Leu Pro Pro Ser
            100                 105                 110

Val Ala Pro Ala Gly Gln Ser Leu Thr Lys Ile Glu Thr Leu Arg Leu
            115                 120                 125

Ala Ile Arg Tyr Ile Gly His Leu Ser Ala Val Leu Gly Leu Ser Glu
        130                 135                 140

Glu Ser Leu Gln Arg Arg Cys Arg Gln Arg Gly Asp Ala Gly Ser Pro
145                 150                 155                 160

Arg Gly Cys Pro Leu Cys Pro Asp Asp Cys Pro Ala Gln Met Gln Thr
                165                 170                 175

Arg Thr Gln Ala Glu Gly Gln Gly Gln Gly Arg Gly Leu Gly Leu Val
            180                 185                 190

Ser Ala Val Arg Ala Gly Ala Ser Trp Gly Ser Pro Pro Ala Cys Pro
            195                 200                 205

```
Gly Ala Arg Ala Ala Pro Glu Pro Arg Asp Pro Ala Leu Phe Ala
        210                 215                 220

Glu Ala Ala Cys Pro Glu Gly Gln Ala Met Glu Pro Ser Pro Pro Ser
225                 230                 235                 240

Pro Leu Leu Pro Gly Asp Val Leu Ala Leu Leu Glu Thr Trp Met Pro
            245                 250                 255

Leu Ser Pro Leu Glu Trp Leu Pro Glu Glu Pro Lys
        260                 265
```

<210> SEQ ID NO 6
<211> LENGTH: 177
<212> TYPE: PRT
<213> ORGANISM: Artificial Sequence
<220> FEATURE:
<223> OTHER INFORMATION: depicts amino acid sequence for Isoform 3 of
      N-alpha-acetyltransferase 60

<400> SEQUENCE: 6

```
Met Ile Val Ala Glu Ile Lys Asn Arg Thr Lys Ile His Lys Glu Asp
1               5                   10                  15

Gly Asp Ile Leu Ala Ser Asn Phe Ser Val Asp Thr Gln Val Ala Tyr
            20                  25                  30

Ile Leu Ser Leu Gly Val Val Lys Glu Phe Arg Lys His Gly Ile Gly
        35                  40                  45

Ser Leu Leu Leu Glu Ser Leu Lys Asp His Ile Ser Thr Thr Ala Gln
50                  55                  60

Asp His Cys Lys Ala Ile Tyr Leu His Val Leu Thr Thr Asn Asn Thr
65                  70                  75                  80

Ala Ile Asn Phe Tyr Glu Asn Arg Asp Phe Lys Gln His His Tyr Leu
                85                  90                  95

Pro Tyr Tyr Tyr Ser Ile Arg Gly Val Leu Lys Asp Gly Phe Thr Tyr
            100                 105                 110

Val Leu Tyr Ile Asn Gly Gly His Pro Pro Trp Thr Ile Leu Asp Tyr
        115                 120                 125

Ile Gln His Leu Gly Ser Ala Leu Ala Ser Leu Ser Pro Cys Ser Ile
130                 135                 140

Pro His Arg Val Tyr Arg Gln Ala His Ser Leu Leu Cys Ser Phe Leu
145                 150                 155                 160

Pro Trp Ser Gly Ile Ser Ser Lys Ser Gly Ile Glu Tyr Ser Arg Thr
                165                 170                 175

Met
```

<210> SEQ ID NO 7
<211> LENGTH: 442
<212> TYPE: PRT
<213> ORGANISM: Artificial Sequence
<220> FEATURE:
<223> OTHER INFORMATION: depicts amino acid sequence for Isoform 3 of
      Serine/threonine-protein kinase Chk1

<400> SEQUENCE: 7

```
Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45
```

```
Pro Glu Asn Ile Lys Lys Glu Ile Cys Ile Asn Lys Met Leu Asn His
     50                  55                  60

Glu Asn Val Val Lys Phe Tyr Gly His Arg Arg Glu Gly Asn Ile Gln
 65                  70                  75                  80

Tyr Leu Phe Leu Glu Tyr Cys Ser Gly Gly Glu Leu Phe Asp Arg Ile
                 85                  90                  95

Glu Pro Asp Ile Gly Met Pro Glu Pro Asp Ala Gln Arg Phe Phe His
                100                 105                 110

Gln Leu Met Ala Gly Val Val Tyr Leu His Gly Ile Gly Ile Thr His
            115                 120                 125

Arg Asp Ile Lys Pro Glu Asn Leu Leu Leu Asp Glu Arg Asp Asn Leu
130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
                180                 185                 190

Ser Cys Gly Ile Val Leu Thr Ala Met Leu Ala Gly Glu Leu Pro Trp
            195                 200                 205

Asp Gln Pro Ser Asp Ser Cys Gln Glu Tyr Ser Asp Trp Lys Glu Lys
210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
                260                 265                 270

Ala Lys Arg Pro Arg Val Thr Ser Gly Gly Val Ser Glu Ser Pro Ser
            275                 280                 285

Gly Phe Ser Lys His Ile Gln Ser Asn Leu Asp Phe Ser Pro Val Asn
290                 295                 300

Ser Ala Ser Ser Glu Glu Asn Val Lys Tyr Ser Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
                340                 345                 350

Met Leu Leu Asn Ser Gln Leu Leu Gly Thr Pro Gly Ser Ser Gln Asn
            355                 360                 365

Pro Trp Gln Arg Leu Val Lys Arg Met Thr Arg Phe Phe Thr Lys Leu
370                 375                 380

Asp Ala Asp Lys Ser Tyr Gln Cys Leu Lys Glu Thr Cys Glu Lys Leu
385                 390                 395                 400

Gly Tyr Gln Trp Lys Lys Ser Cys Met Asn Gln Gly Asp Gly Leu Glu
                405                 410                 415

Phe Lys Arg His Phe Leu Lys Ile Lys Gly Lys Leu Ile Asp Ile Val
                420                 425                 430

Ser Ser Gln Lys Ile Trp Leu Pro Ala Thr
            435                 440

<210> SEQ ID NO 8
<211> LENGTH: 364
<212> TYPE: PRT
```

<213> ORGANISM: Artificial Sequence
<220> FEATURE:
<223> OTHER INFORMATION: depicts amino acid sequence for Fructose-
    bisphosphate aldolase A

<400> SEQUENCE: 8

```
Met Pro Tyr Gln Tyr Pro Ala Leu Thr Pro Glu Gln Lys Lys Glu Leu
1               5                   10                  15

Ser Asp Ile Ala His Arg Ile Val Ala Pro Gly Lys Gly Ile Leu Ala
            20                  25                  30

Ala Asp Glu Ser Thr Gly Ser Ile Ala Lys Arg Leu Gln Ser Ile Gly
        35                  40                  45

Thr Glu Asn Thr Glu Glu Asn Arg Arg Phe Tyr Arg Gln Leu Leu Leu
    50                  55                  60

Thr Ala Asp Asp Arg Val Asn Pro Cys Ile Gly Gly Val Ile Leu Phe
65                  70                  75                  80

His Glu Thr Leu Tyr Gln Lys Ala Asp Asp Gly Arg Pro Phe Pro Gln
                85                  90                  95

Val Ile Lys Ser Lys Gly Gly Val Val Gly Ile Lys Val Asp Lys Gly
            100                 105                 110

Val Val Pro Leu Ala Gly Thr Asn Gly Glu Thr Thr Thr Gln Gly Leu
        115                 120                 125

Asp Gly Leu Ser Glu Arg Cys Ala Gln Tyr Lys Lys Asp Gly Ala Asp
    130                 135                 140

Phe Ala Lys Trp Arg Cys Val Leu Lys Ile Gly Glu His Thr Pro Ser
145                 150                 155                 160

Ala Leu Ala Ile Met Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
            180                 185                 190

Pro Asp Gly Asp His Asp Leu Lys Arg Cys Gln Tyr Val Thr Glu Lys
        195                 200                 205

Val Leu Ala Ala Val Tyr Lys Ala Leu Ser Asp His His Ile Tyr Leu
    210                 215                 220

Glu Gly Thr Leu Leu Lys Pro Asn Met Val Thr Pro Gly His Ala Cys
225                 230                 235                 240

Thr Gln Lys Phe Ser His Glu Glu Ile Ala Met Ala Thr Val Thr Ala
                245                 250                 255

Leu Arg Arg Thr Val Pro Pro Ala Val Thr Gly Ile Thr Phe Leu Ser
            260                 265                 270

Gly Gly Gln Ser Glu Glu Glu Ala Ser Ile Asn Leu Asn Ala Ile Asn
        275                 280                 285

Lys Cys Pro Leu Leu Lys Pro Trp Ala Leu Thr Phe Ser Tyr Gly Arg
    290                 295                 300

Ala Leu Gln Ala Ser Ala Leu Lys Ala Trp Gly Gly Lys Lys Glu Asn
305                 310                 315                 320

Leu Lys Ala Ala Gln Glu Glu Tyr Val Lys Arg Ala Leu Ala Asn Ser
                325                 330                 335

Leu Ala Cys Gln Gly Lys Tyr Thr Pro Ser Gly Gln Ala Gly Ala Ala
            340                 345                 350

Ala Ser Glu Ser Leu Phe Val Ser Asn His Ala Tyr
        355                 360
```

<210> SEQ ID NO 9
<211> LENGTH: 167

<212> TYPE: PRT
<213> ORGANISM: Artificial Sequence
<220> FEATURE:
<223> OTHER INFORMATION: depicts amino acid sequence for Isoform 4 of
      Triosephosphate isomerase

<400> SEQUENCE: 9

Met Ile Lys Asp Cys Gly Ala Thr Trp Val Leu Gly His Ser Glu
1               5                   10                  15

Arg Arg His Val Phe Gly Glu Ser Asp Glu Leu Ile Gly Gln Lys Val
                20                  25                  30

Ala His Ala Leu Ala Glu Gly Leu Gly Val Ile Ala Cys Ile Gly Glu
            35                  40                  45

Lys Leu Asp Glu Arg Glu Ala Gly Ile Thr Glu Lys Val Val Phe Glu
    50                  55                  60

Gln Thr Lys Val Ile Ala Asp Asn Val Lys Asp Trp Ser Lys Val Val
65                  70                  75                  80

Leu Ala Tyr Glu Pro Val Trp Ala Ile Gly Thr Gly Lys Thr Ala Thr
                85                  90                  95

Pro Gln Gln Ala Gln Glu Val His Glu Lys Leu Arg Gly Trp Leu Lys
            100                 105                 110

Ser Asn Val Ser Asp Ala Val Ala Gln Ser Thr Arg Ile Ile Tyr Gly
        115                 120                 125

Gly Ser Val Thr Gly Ala Thr Cys Lys Glu Leu Ala Ser Gln Pro Asp
130                 135                 140

Val Asp Gly Phe Leu Val Gly Gly Ala Ser Leu Lys Pro Glu Phe Val
145                 150                 155                 160

Asp Ile Ile Asn Ala Lys Gln
                165

<210> SEQ ID NO 10
<211> LENGTH: 1690
<212> TYPE: PRT
<213> ORGANISM: Artificial Sequence
<220> FEATURE:
<223> OTHER INFORMATION: depicts amino acid sequence for Trinucleotide
      repeat-containing gene 6C protein

<400> SEQUENCE: 10

Met Ala Thr Gly Ser Ala Gln Gly Asn Phe Thr Gly His Thr Lys Lys
1               5                   10                  15

Thr Asn Gly Asn Asn Gly Thr Asn Gly Ala Leu Val Gln Ser Pro Ser
                20                  25                  30

Asn Gln Ser Ala Leu Gly Ala Gly Ala Asn Ser Asn Gly Ser Ala
            35                  40                  45

Ala Arg Val Trp Gly Val Ala Thr Gly Ser Ser Gly Leu Ala His
    50                  55                  60

Cys Ser Val Ser Gly Gly Asp Gly Lys Met Asp Thr Met Ile Gly Asp
65                  70                  75                  80

Gly Arg Ser Gln Asn Cys Trp Gly Ala Ser Ser Asn Ala Gly Ile
                85                  90                  95

Asn Leu Asn Leu Asn Pro Asn Ala Asn Pro Ala Ala Trp Pro Val Leu
            100                 105                 110

Gly His Glu Gly Thr Val Ala Thr Gly Asn Pro Ser Ser Ile Cys Ser
        115                 120                 125

Pro Val Ser Ala Ile Gly Gln Asn Met Gly Asn Gln Asn Gly Asn Pro
130                 135                 140

```
Thr Gly Thr Leu Gly Ala Trp Gly Asn Leu Leu Pro Gln Glu Ser Thr
145                 150                 155                 160

Glu Pro Gln Thr Ser Thr Ser Gln Asn Val Ser Phe Ser Ala Gln Pro
            165                 170                 175

Gln Asn Leu Asn Thr Asp Gly Pro Asn Thr Asn Pro Met Asn Ser
        180                 185                 190

Ser Pro Asn Pro Ile Asn Ala Met Gln Thr Asn Gly Leu Pro Asn Trp
        195                 200                 205

Gly Met Ala Val Gly Met Gly Ala Ile Ile Pro His Leu Gln Gly
        210                 215                 220

Leu Pro Gly Ala Asn Gly Ser Ser Val Ser Gln Val Ser Gly Gly Ser
225                 230                 235                 240

Ala Glu Gly Ile Ser Asn Ser Val Trp Gly Leu Ser Pro Gly Asn Pro
                245                 250                 255

Ala Thr Gly Asn Ser Asn Ser Gly Phe Ser Gln Gly Asn Gly Asp Thr
                260                 265                 270

Val Asn Ser Ala Leu Ser Ala Lys Gln Asn Gly Ser Ser Ala Val
        275                 280                 285

Gln Lys Glu Gly Ser Gly Gly Asn Ala Trp Asp Ser Gly Pro Pro Ala
290                 295                 300

Gly Pro Gly Ile Leu Ala Trp Gly Arg Gly Ser Gly Asn Asn Gly Val
305                 310                 315                 320

Gly Asn Ile His Ser Gly Ala Trp Gly His Pro Ser Arg Ser Thr Ser
                325                 330                 335

Asn Gly Val Asn Gly Glu Trp Gly Lys Pro Pro Asn Gln His Ser Asn
                340                 345                 350

Ser Asp Ile Asn Gly Lys Gly Ser Thr Gly Trp Glu Ser Pro Ser Val
        355                 360                 365

Thr Ser Gln Asn Pro Thr Val Gln Pro Gly Gly Glu His Met Asn Ser
        370                 375                 380

Trp Ala Lys Ala Ala Ser Ser Gly Thr Thr Ala Ser Glu Gly Ser Ser
385                 390                 395                 400

Asp Gly Ser Gly Asn His Asn Glu Gly Ser Thr Gly Arg Glu Gly Thr
                405                 410                 415

Gly Glu Gly Arg Arg Arg Asp Lys Gly Ile Ile Asp Gln Gly His Ile
                420                 425                 430

Gln Leu Pro Arg Asn Asp Leu Asp Pro Arg Val Leu Ser Asn Thr Gly
            435                 440                 445

Trp Gly Gln Thr Pro Val Lys Gln Asn Thr Ala Trp Glu Phe Glu Glu
450                 455                 460

Ser Pro Arg Ser Glu Arg Lys Asn Asp Asn Gly Thr Glu Ala Trp Gly
465                 470                 475                 480

Cys Ala Ala Thr Gln Ala Ser Asn Ser Gly Gly Lys Asn Asp Gly Ser
                485                 490                 495

Ile Met Asn Ser Thr Asn Thr Ser Ser Val Ser Gly Trp Val Asn Ala
            500                 505                 510

Pro Pro Ala Ala Val Pro Ala Asn Thr Gly Trp Gly Asp Ser Asn Asn
            515                 520                 525

Lys Ala Pro Ser Gly Pro Gly Val Trp Gly Asp Ser Ile Ser Ser Thr
        530                 535                 540

Ala Val Ser Thr Ala Ala Ala Lys Ser Gly His Ala Trp Ser Gly
545                 550                 555                 560
```

```
Ala Ala Asn Gln Glu Asp Lys Ser Pro Thr Trp Glu Pro Pro Lys
            565                 570                 575

Pro Lys Ser Gln His Trp Gly Asp Gly Gln Arg Ser Asn Pro Ala Trp
        580                 585                 590

Ser Ala Gly Gly Gly Asp Trp Ala Asp Ser Ser Val Leu Gly His
        595                 600                 605

Leu Gly Asp Gly Lys Lys Asn Gly Ser Gly Trp Asp Ala Asp Ser Asn
        610                 615                 620

Arg Ser Gly Ser Gly Trp Asn Asp Thr Thr Arg Ser Gly Asn Ser Gly
625                 630                 635                 640

Trp Gly Asn Ser Thr Asn Thr Lys Ala Asn Pro Gly Thr Asn Trp Gly
                645                 650                 655

Glu Thr Leu Lys Pro Gly Pro Gln Gln Asn Trp Ala Ser Lys Pro Gln
            660                 665                 670

Asp Asn Asn Val Ser Asn Trp Gly Ala Ala Ser Val Lys Gln Thr
            675                 680                 685

Gly Thr Gly Trp Ile Gly Gly Pro Val Pro Val Lys Gln Lys Asp Ser
        690                 695                 700

Ser Glu Ala Thr Gly Trp Glu Glu Pro Ser Pro Pro Ser Ile Arg Arg
705                 710                 715                 720

Lys Met Glu Ile Asp Asp Gly Thr Ser Ala Trp Gly Asp Pro Ser Asn
                725                 730                 735

Tyr Asn Asn Lys Thr Val Asn Met Trp Asp Arg Asn Asn Pro Val Ile
                740                 745                 750

Gln Ser Ser Thr Thr Asn Thr Thr Thr Thr Thr Thr Thr Thr
            755                 760                 765

Ser Asn Thr Thr His Arg Val Glu Thr Pro Pro His Gln Ala Gly
            770                 775                 780

Thr Gln Leu Asn Arg Ser Pro Leu Leu Gly Pro Gly Arg Lys Val Ser
785                 790                 795                 800

Ser Gly Trp Gly Glu Met Pro Asn Val His Ser Lys Thr Glu Asn Ser
            805                 810                 815

Trp Gly Glu Pro Ser Ser Pro Ser Thr Leu Val Asp Asn Gly Thr Ala
                820                 825                 830

Ala Trp Gly Lys Pro Pro Ser Ser Gly Ser Gly Trp Gly Asp His Pro
        835                 840                 845

Ala Glu Pro Pro Val Ala Phe Gly Arg Ala Gly Ala Pro Val Ala Ala
        850                 855                 860

Ser Ala Leu Cys Lys Pro Ala Ser Lys Ser Met Gln Glu Gly Trp Gly
865                 870                 875                 880

Ser Gly Gly Asp Glu Met Asn Leu Ser Thr Ser Gln Trp Glu Asp Glu
                885                 890                 895

Glu Gly Asp Val Trp Asn Asn Ala Ala Ser Gln Glu Ser Thr Ser Ser
            900                 905                 910

Cys Ser Ser Trp Gly Asn Ala Pro Lys Lys Gly Leu Gln Lys Gly Met
            915                 920                 925

Lys Thr Ser Gly Lys Gln Asp Glu Ala Trp Ile Met Ser Arg Leu Ile
930                 935                 940

Lys Gln Leu Thr Asp Met Gly Phe Pro Arg Glu Pro Ala Glu Glu Ala
945                 950                 955                 960

Leu Lys Ser Asn Asn Met Asn Leu Asp Gln Ala Met Ser Ala Leu Leu
                965                 970                 975
```

-continued

```
Glu Lys Lys Val Asp Val Asp Lys Arg Gly Leu Gly Val Thr Asp His
            980                 985                 990
Asn Gly Met Ala Ala Lys Pro Leu Gly Cys Arg Pro Pro Ile Ser Lys
            995                 1000                1005
Glu Ser Ser Val Asp Arg Pro Thr Phe Leu Asp Lys Asp Gly Gly
        1010                1015                1020
Leu Val Glu Glu Pro Thr Pro Ser Pro Phe Leu Pro Ser Pro Ser
        1025                1030                1035
Leu Lys Leu Pro Leu Ser His Ser Ala Leu Pro Ser Gln Ala Leu
        1040                1045                1050
Gly Gly Ile Ala Ser Gly Leu Gly Met Gln Asn Leu Asn Ser Ser
        1055                1060                1065
Arg Gln Ile Pro Ser Gly Asn Leu Gly Met Phe Gly Asn Ser Gly
        1070                1075                1080
Ala Ala Gln Ala Arg Thr Met Gln Gln Pro Pro Gln Pro Pro Val
        1085                1090                1095
Gln Pro Leu Asn Ser Ser Gln Pro Ser Leu Arg Ala Gln Val Pro
        1100                1105                1110
Gln Phe Leu Ser Pro Gln Val Gln Ala Gln Leu Leu Gln Phe Ala
        1115                1120                1125
Ala Lys Asn Ile Gly Leu Asn Pro Ala Leu Leu Thr Ser Pro Ile
        1130                1135                1140
Asn Pro Gln His Met Thr Met Leu Asn Gln Leu Tyr Gln Leu Gln
        1145                1150                1155
Leu Ala Tyr Gln Arg Leu Gln Ile Gln Gln Gln Met Leu Gln Ala
        1160                1165                1170
Gln Arg Asn Val Ser Gly Ser Met Arg Gln Gln Glu Gln Gln Val
        1175                1180                1185
Ala Arg Thr Ile Thr Asn Leu Gln Gln Gln Ile Gln Gln His Gln
        1190                1195                1200
Arg Gln Leu Ala Gln Ala Leu Leu Val Lys Gln Pro Pro Pro
        1205                1210                1215
Pro Pro Pro Pro His Leu Ser Leu His Pro Ser Ala Gly Lys Ser
        1220                1225                1230
Ala Met Asp Ser Phe Pro Ser His Pro Gln Thr Pro Gly Leu Pro
        1235                1240                1245
Asp Leu Gln Thr Lys Glu Gln Gln Ser Ser Pro Asn Thr Phe Ala
        1250                1255                1260
Pro Tyr Pro Leu Ala Gly Leu Asn Pro Asn Met Asn Val Asn Ser
        1265                1270                1275
Met Asp Met Thr Gly Gly Leu Ser Val Lys Asp Pro Ser Gln Ser
        1280                1285                1290
Gln Ser Arg Leu Pro Gln Trp Thr His Pro Asn Ser Met Asp Asn
        1295                1300                1305
Leu Pro Ser Ala Ala Ser Pro Leu Glu Gln Asn Pro Ser Lys His
        1310                1315                1320
Gly Ala Ile Pro Gly Gly Leu Ser Ile Gly Pro Pro Gly Lys Ser
        1325                1330                1335
Ser Ile Asp Asp Ser Tyr Gly Arg Tyr Asp Leu Ile Gln Asn Ser
        1340                1345                1350
Glu Ser Pro Ala Ser Pro Pro Val Ala Val Pro His Ser Trp Ser
        1355                1360                1365
```

-continued

```
Arg Ala Lys Ser Asp Ser Asp Lys Ile Ser Asn Gly Ser Ser Ile
    1370            1375                1380

Asn Trp Pro Pro Glu Phe His Pro Gly Val Pro Trp Lys Gly Leu
    1385            1390                1395

Gln Asn Ile Asp Pro Glu Asn Asp Pro Asp Val Thr Pro Gly Ser
    1400            1405                1410

Val Pro Thr Gly Pro Thr Ile Asn Thr Thr Ile Gln Asp Val Asn
    1415            1420                1425

Arg Tyr Leu Leu Lys Ser Gly Gly Lys Leu Ser Asp Ile Lys Ser
    1430            1435                1440

Thr Trp Ser Ser Gly Pro Thr Ser His Thr Gln Ala Ser Leu Ser
    1445            1450                1455

His Glu Leu Trp Lys Val Pro Arg Asn Ser Thr Ala Pro Thr Arg
    1460            1465                1470

Pro Pro Pro Gly Leu Thr Asn Pro Lys Pro Ser Ser Thr Trp Gly
    1475            1480                1485

Ala Ser Pro Leu Gly Trp Thr Ser Ser Tyr Ser Ser Gly Ser Ala
    1490            1495                1500

Trp Ser Thr Asp Thr Ser Gly Arg Thr Ser Ser Trp Leu Val Leu
    1505            1510                1515

Arg Asn Leu Thr Pro Gln Ile Asp Gly Ser Thr Leu Arg Thr Leu
    1520            1525                1530

Cys Leu Gln His Gly Pro Leu Ile Thr Phe His Leu Asn Leu Thr
    1535            1540                1545

Gln Gly Asn Ala Val Val Arg Tyr Ser Ser Lys Glu Glu Ala Ala
    1550            1555                1560

Lys Ala Gln Lys Ser Leu His Met Cys Val Leu Gly Asn Thr Thr
    1565            1570                1575

Ile Leu Ala Glu Phe Ala Gly Glu Glu Glu Val Asn Arg Phe Leu
    1580            1585                1590

Ala Gln Gly Gln Ala Leu Pro Pro Thr Ser Ser Trp Gln Ser Ser
    1595            1600                1605

Ser Ala Ser Ser Gln Pro Arg Leu Ser Ala Ala Gly Ser Ser His
    1610            1615                1620

Gly Leu Val Arg Ser Asp Ala Gly His Trp Asn Ala Pro Cys Leu
    1625            1630                1635

Gly Gly Lys Gly Ser Ser Glu Leu Leu Trp Gly Gly Val Pro Gln
    1640            1645                1650

Tyr Ser Ser Ser Leu Trp Gly Pro Pro Ser Ala Asp Asp Ser Arg
    1655            1660                1665

Val Ile Gly Ser Pro Thr Pro Leu Thr Thr Leu Leu Pro Gly Asp
    1670            1675                1680

Leu Leu Ser Gly Glu Ser Leu
    1685            1690

<210> SEQ ID NO 11
<211> LENGTH: 103
<212> TYPE: PRT
<213> ORGANISM: Artificial Sequence
<220> FEATURE:
<223> OTHER INFORMATION: depicts amino acid sequence for Histone H4

<400> SEQUENCE: 11

Met Ser Gly Arg Gly Lys Gly Gly Lys Gly Leu Gly Lys Gly Gly Ala
1               5                   10                  15
```

```
Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
            35                  40                  45

Gly Leu Ile Tyr Glu Glu Thr Arg Gly Val Leu Lys Val Phe Leu Glu
 50                  55                  60

Asn Val Ile Arg Asp Ala Val Thr Tyr Thr Glu His Ala Lys Arg Lys
 65                  70                  75                  80

Thr Val Thr Ala Met Asp Val Val Tyr Ala Leu Lys Arg Gln Gly Arg
                    85                  90                  95

Thr Leu Tyr Gly Phe Gly Gly
                100

<210> SEQ ID NO 12
<211> LENGTH: 3114
<212> TYPE: PRT
<213> ORGANISM: Artificial Sequence
<220> FEATURE:
<223> OTHER INFORMATION: depicts amino acid sequence for Centromere
      protein F

<400> SEQUENCE: 12

Met Ser Trp Ala Leu Glu Glu Trp Lys Glu Gly Leu Pro Thr Arg Ala
 1               5                  10                  15

Leu Gln Lys Ile Gln Glu Leu Glu Gly Gln Leu Asp Lys Leu Lys Lys
            20                  25                  30

Glu Lys Gln Gln Arg Gln Phe Gln Leu Asp Ser Leu Glu Ala Ala Leu
            35                  40                  45

Gln Lys Gln Lys Gln Lys Val Glu Asn Glu Lys Thr Glu Gly Thr Asn
 50                  55                  60

Leu Lys Arg Glu Asn Gln Arg Leu Met Glu Ile Cys Glu Ser Leu Glu
 65                  70                  75                  80

Lys Thr Lys Gln Lys Ile Ser His Glu Leu Gln Val Lys Glu Ser Gln
                    85                  90                  95

Val Asn Phe Gln Glu Gly Gln Leu Asn Ser Gly Lys Lys Gln Ile Glu
                100                 105                 110

Lys Leu Glu Gln Glu Leu Lys Arg Cys Lys Ser Glu Leu Glu Arg Ser
            115                 120                 125

Gln Gln Ala Ala Gln Ser Ala Asp Val Ser Leu Asn Pro Cys Asn Thr
        130                 135                 140

Pro Gln Lys Ile Phe Thr Thr Pro Leu Thr Pro Ser Gln Tyr Tyr Ser
145                 150                 155                 160

Gly Ser Lys Tyr Glu Asp Leu Lys Glu Lys Tyr Asn Lys Glu Val Glu
                165                 170                 175

Glu Arg Lys Arg Leu Glu Ala Glu Val Lys Ala Leu Gln Ala Lys Lys
            180                 185                 190

Ala Ser Gln Thr Leu Pro Gln Ala Thr Met Asn His Arg Asp Ile Ala
        195                 200                 205

Arg His Gln Ala Ser Ser Val Phe Ser Trp Gln Gln Glu Lys Thr
        210                 215                 220

Pro Ser His Leu Ser Ser Asn Ser Gln Arg Thr Pro Ile Arg Arg Asp
225                 230                 235                 240

Phe Ser Ala Ser Tyr Phe Ser Gly Glu Gln Glu Val Thr Pro Ser Arg
                245                 250                 255
```

-continued

Ser Thr Leu Gln Ile Gly Lys Arg Asp Ala Asn Ser Ser Phe Phe Asp
            260                 265                 270

Asn Ser Ser Pro His Leu Asp Gln Leu Lys Ala Gln Asn Gln
            275                 280                 285

Glu Leu Arg Asn Lys Ile Asn Glu Leu Glu Leu Arg Leu Gln Gly His
            290                 295                 300

Glu Lys Glu Met Lys Gly Gln Val Asn Lys Phe Gln Glu Leu Gln Leu
305                 310                 315                 320

Gln Leu Glu Lys Ala Lys Val Glu Leu Ile Glu Lys Glu Lys Val Leu
            325                 330                 335

Asn Lys Cys Arg Asp Glu Leu Val Arg Thr Thr Ala Gln Tyr Asp Gln
            340                 345                 350

Ala Ser Thr Lys Tyr Thr Ala Leu Glu Gln Lys Leu Lys Lys Leu Thr
            355                 360                 365

Glu Asp Leu Ser Cys Gln Arg Gln Asn Ala Glu Ser Ala Arg Cys Ser
            370                 375                 380

Leu Glu Gln Lys Ile Lys Glu Lys Glu Lys Glu Phe Gln Glu Glu Leu
385                 390                 395                 400

Ser Arg Gln Gln Arg Ser Phe Gln Thr Leu Asp Gln Glu Cys Ile Gln
            405                 410                 415

Met Lys Ala Arg Leu Thr Gln Glu Leu Gln Gln Ala Lys Asn Met His
            420                 425                 430

Asn Val Leu Gln Ala Glu Leu Asp Lys Leu Thr Ser Val Lys Gln Gln
            435                 440                 445

Leu Glu Asn Asn Leu Glu Glu Phe Lys Gln Lys Leu Cys Arg Ala Glu
            450                 455                 460

Gln Ala Phe Gln Ala Ser Gln Ile Lys Glu Asn Glu Leu Arg Arg Ser
465                 470                 475                 480

Met Glu Glu Met Lys Lys Glu Asn Asn Leu Leu Lys Ser His Ser Glu
            485                 490                 495

Gln Lys Ala Arg Glu Val Cys His Leu Glu Ala Glu Leu Lys Asn Ile
            500                 505                 510

Lys Gln Cys Leu Asn Gln Ser Gln Asn Phe Ala Glu Glu Met Lys Ala
            515                 520                 525

Lys Asn Thr Ser Gln Glu Thr Met Leu Arg Asp Leu Gln Glu Lys Ile
            530                 535                 540

Asn Gln Gln Glu Asn Ser Leu Thr Leu Glu Lys Leu Lys Leu Ala Val
545                 550                 555                 560

Ala Asp Leu Glu Lys Gln Arg Asp Cys Ser Gln Asp Leu Leu Lys Lys
            565                 570                 575

Arg Glu His His Ile Glu Gln Leu Asn Asp Lys Leu Ser Lys Thr Glu
            580                 585                 590

Lys Glu Ser Lys Ala Leu Leu Ser Ala Leu Glu Leu Lys Lys Lys Glu
            595                 600                 605

Tyr Glu Glu Leu Lys Glu Glu Lys Thr Leu Phe Ser Cys Trp Lys Ser
            610                 615                 620

Glu Asn Glu Lys Leu Leu Thr Gln Met Glu Ser Glu Lys Glu Asn Leu
625                 630                 635                 640

Gln Ser Lys Ile Asn His Leu Glu Thr Cys Leu Lys Thr Gln Gln Ile
            645                 650                 655

Lys Ser His Glu Tyr Asn Glu Arg Val Arg Thr Leu Glu Met Asp Arg
            660                 665                 670

```
Glu Asn Leu Ser Val Glu Ile Arg Asn Leu His Asn Val Leu Asp Ser
            675                 680                 685

Lys Ser Val Glu Val Thr Gln Lys Leu Ala Tyr Met Glu Leu Gln
690                 695                 700

Gln Lys Ala Glu Phe Ser Asp Gln Lys His Gln Lys Glu Ile Glu Asn
705                 710                 715                 720

Met Cys Leu Lys Thr Ser Gln Leu Thr Gly Gln Val Glu Asp Leu Glu
            725                 730                 735

His Lys Leu Gln Leu Leu Ser Asn Glu Ile Met Asp Lys Asp Arg Cys
            740                 745                 750

Tyr Gln Asp Leu His Ala Glu Tyr Glu Ser Leu Arg Asp Leu Leu Lys
            755                 760                 765

Ser Lys Asp Ala Ser Leu Val Thr Asn Glu Asp His Gln Arg Ser Leu
770                 775                 780

Leu Ala Phe Asp Gln Gln Pro Ala Met His His Ser Phe Ala Asn Ile
785                 790                 795                 800

Ile Gly Glu Gln Gly Ser Met Pro Ser Glu Arg Ser Glu Cys Arg Leu
                805                 810                 815

Glu Ala Asp Gln Ser Pro Lys Asn Ser Ala Ile Leu Gln Asn Arg Val
            820                 825                 830

Asp Ser Leu Glu Phe Ser Leu Glu Ser Gln Lys Gln Met Asn Ser Asp
            835                 840                 845

Leu Gln Lys Gln Cys Glu Glu Leu Val Gln Ile Lys Gly Glu Ile Glu
            850                 855                 860

Glu Asn Leu Met Lys Ala Glu Gln Met His Gln Ser Phe Val Ala Glu
865                 870                 875                 880

Thr Ser Gln Arg Ile Ser Lys Leu Gln Glu Asp Thr Ser Ala His Gln
                885                 890                 895

Asn Val Val Ala Glu Thr Leu Ser Ala Leu Glu Asn Lys Glu Lys Glu
                900                 905                 910

Leu Gln Leu Leu Asn Asp Lys Val Glu Thr Glu Gln Ala Glu Ile Gln
            915                 920                 925

Glu Leu Lys Lys Ser Asn His Leu Leu Glu Asp Ser Leu Lys Glu Leu
930                 935                 940

Gln Leu Leu Ser Glu Thr Leu Ser Leu Glu Lys Lys Glu Met Ser Ser
945                 950                 955                 960

Ile Ile Ser Leu Asn Lys Arg Glu Ile Glu Leu Thr Gln Glu Asn
                965                 970                 975

Gly Thr Leu Lys Glu Ile Asn Ala Ser Leu Asn Gln Glu Lys Met Asn
            980                 985                 990

Leu Ile Gln Lys Ser Glu Ser Phe Ala Asn Tyr Ile Asp Glu Arg Glu
                995                1000                1005

Lys Ser Ile Ser Glu Leu Ser Asp Gln Tyr Lys Gln Glu Lys Leu
    1010                1015                1020

Ile Leu Leu Gln Arg Cys Glu Glu Thr Gly Asn Ala Tyr Glu Asp
    1025                1030                1035

Leu Ser Gln Lys Tyr Lys Ala Ala Gln Glu Lys Asn Ser Lys Leu
    1040                1045                1050

Glu Cys Leu Leu Asn Glu Cys Thr Ser Leu Cys Glu Asn Arg Lys
    1055                1060                1065

Asn Glu Leu Glu Gln Leu Lys Glu Ala Phe Ala Lys Glu His Gln
    1070                1075                1080
```

```
Glu Phe Leu Thr Lys Leu Ala Phe Ala Glu Glu Arg Asn Gln Asn
    1085                1090                1095

Leu Met Leu Glu Leu Glu Thr Val Gln Gln Ala Leu Arg Ser Glu
    1100                1105                1110

Met Thr Asp Asn Gln Asn Asn Ser Lys Ser Glu Ala Gly Gly Leu
    1115                1120                1125

Lys Gln Glu Ile Met Thr Leu Lys Glu Glu Gln Asn Lys Met Gln
    1130                1135                1140

Lys Glu Val Asn Asp Leu Leu Gln Glu Asn Glu Gln Leu Met Lys
    1145                1150                1155

Val Met Lys Thr Lys His Glu Cys Gln Asn Leu Glu Ser Glu Pro
    1160                1165                1170

Ile Arg Asn Ser Val Lys Glu Arg Glu Ser Glu Arg Asn Gln Cys
    1175                1180                1185

Asn Phe Lys Pro Gln Met Asp Leu Glu Val Lys Glu Ile Ser Leu
    1190                1195                1200

Asp Ser Tyr Asn Ala Gln Leu Val Gln Leu Glu Ala Met Leu Arg
    1205                1210                1215

Asn Lys Glu Leu Lys Leu Gln Glu Ser Glu Lys Glu Lys Glu Cys
    1220                1225                1230

Leu Gln His Glu Leu Gln Thr Ile Arg Gly Asp Leu Glu Thr Ser
    1235                1240                1245

Asn Leu Gln Asp Met Gln Ser Gln Glu Ile Ser Gly Leu Lys Asp
    1250                1255                1260

Cys Glu Ile Asp Ala Glu Glu Lys Tyr Ile Ser Gly Pro His Glu
    1265                1270                1275

Leu Ser Thr Ser Gln Asn Asp Asn Ala His Leu Gln Cys Ser Leu
    1280                1285                1290

Gln Thr Thr Met Asn Lys Leu Asn Glu Leu Glu Lys Ile Cys Glu
    1295                1300                1305

Ile Leu Gln Ala Glu Lys Tyr Glu Leu Val Thr Glu Leu Asn Asp
    1310                1315                1320

Ser Arg Ser Glu Cys Ile Thr Ala Thr Arg Lys Met Ala Glu Glu
    1325                1330                1335

Val Gly Lys Leu Leu Asn Glu Val Lys Ile Leu Asn Asp Asp Ser
    1340                1345                1350

Gly Leu Leu His Gly Glu Leu Val Glu Asp Ile Pro Gly Gly Glu
    1355                1360                1365

Phe Gly Glu Gln Pro Asn Glu Gln His Pro Val Ser Leu Ala Pro
    1370                1375                1380

Leu Asp Glu Ser Asn Ser Tyr Glu His Leu Thr Leu Ser Asp Lys
    1385                1390                1395

Glu Val Gln Met His Phe Ala Glu Leu Gln Glu Lys Phe Leu Ser
    1400                1405                1410

Leu Gln Ser Glu His Lys Ile Leu His Asp Gln His Cys Gln Met
    1415                1420                1425

Ser Ser Lys Met Ser Glu Leu Gln Thr Tyr Val Asp Ser Leu Lys
    1430                1435                1440

Ala Glu Asn Leu Val Leu Ser Thr Asn Leu Arg Asn Phe Gln Gly
    1445                1450                1455

Asp Leu Val Lys Glu Met Gln Leu Gly Leu Glu Glu Gly Leu Val
    1460                1465                1470
```

-continued

Pro Ser Leu Ser Ser Ser Cys Val Pro Asp Ser Ser Ser Leu Ser
1475                1480                1485

Ser Leu Gly Asp Ser Ser Phe Tyr Arg Ala Leu Leu Glu Gln Thr
1490                1495                1500

Gly Asp Met Ser Leu Leu Ser Asn Leu Glu Gly Ala Val Ser Ala
1505                1510                1515

Asn Gln Cys Ser Val Asp Glu Val Phe Cys Ser Ser Leu Gln Glu
1520                1525                1530

Glu Asn Leu Thr Arg Lys Glu Thr Pro Ser Ala Pro Ala Lys Gly
1535                1540                1545

Val Glu Glu Leu Glu Ser Leu Cys Glu Val Tyr Arg Gln Ser Leu
1550                1555                1560

Glu Lys Leu Glu Glu Lys Met Glu Ser Gln Gly Ile Met Lys Asn
1565                1570                1575

Lys Glu Ile Gln Glu Leu Glu Gln Leu Leu Ser Ser Glu Arg Gln
1580                1585                1590

Glu Leu Asp Cys Leu Arg Lys Gln Tyr Leu Ser Glu Asn Glu Gln
1595                1600                1605

Trp Gln Gln Lys Leu Thr Ser Val Thr Leu Glu Met Glu Ser Lys
1610                1615                1620

Leu Ala Ala Glu Lys Lys Gln Thr Glu Gln Leu Ser Leu Glu Leu
1625                1630                1635

Glu Val Ala Arg Leu Gln Leu Gln Gly Leu Asp Leu Ser Ser Arg
1640                1645                1650

Ser Leu Leu Gly Ile Asp Thr Glu Asp Ala Ile Gln Gly Arg Asn
1655                1660                1665

Glu Ser Cys Asp Ile Ser Lys Glu His Thr Ser Glu Thr Thr Glu
1670                1675                1680

Arg Thr Pro Lys His Asp Val His Gln Ile Cys Asp Lys Asp Ala
1685                1690                1695

Gln Gln Asp Leu Asn Leu Asp Ile Glu Lys Ile Thr Glu Thr Gly
1700                1705                1710

Ala Val Lys Pro Thr Gly Glu Cys Ser Gly Glu Gln Ser Pro Asp
1715                1720                1725

Thr Asn Tyr Glu Pro Pro Gly Glu Asp Lys Thr Gln Gly Ser Ser
1730                1735                1740

Glu Cys Ile Ser Glu Leu Ser Phe Ser Gly Pro Asn Ala Leu Val
1745                1750                1755

Pro Met Asp Phe Leu Gly Asn Gln Glu Asp Ile His Asn Leu Gln
1760                1765                1770

Leu Arg Val Lys Glu Thr Ser Asn Glu Asn Leu Arg Leu Leu His
1775                1780                1785

Val Ile Glu Asp Arg Asp Arg Lys Val Glu Ser Leu Leu Asn Glu
1790                1795                1800

Met Lys Glu Leu Asp Ser Lys Leu His Leu Gln Glu Val Gln Leu
1805                1810                1815

Met Thr Lys Ile Glu Ala Cys Ile Glu Leu Glu Lys Ile Val Gly
1820                1825                1830

Glu Leu Lys Lys Glu Asn Ser Asp Leu Ser Glu Lys Leu Glu Tyr
1835                1840                1845

Phe Ser Cys Asp His Gln Glu Leu Leu Gln Arg Val Glu Thr Ser
1850                1855                1860

-continued

```
Glu Gly Leu Asn Ser Asp Leu Glu Met His Ala Asp Lys Ser Ser
    1865                1870                1875

Arg Glu Asp Ile Gly Asp Asn Val Ala Lys Val Asn Asp Ser Trp
    1880                1885                1890

Lys Glu Arg Phe Leu Asp Val Glu Asn Glu Leu Ser Arg Ile Arg
    1895                1900                1905

Ser Glu Lys Ala Ser Ile Glu His Glu Ala Leu Tyr Leu Glu Ala
    1910                1915                1920

Asp Leu Glu Val Val Gln Thr Glu Lys Leu Cys Leu Glu Lys Asp
    1925                1930                1935

Asn Glu Asn Lys Gln Lys Val Ile Val Cys Leu Glu Glu Leu
    1940                1945                1950

Ser Val Val Thr Ser Glu Arg Asn Gln Leu Arg Gly Glu Leu Asp
    1955                1960                1965

Thr Met Ser Lys Lys Thr Thr Ala Leu Asp Gln Leu Ser Glu Lys
    1970                1975                1980

Met Lys Glu Lys Thr Gln Glu Leu Glu Ser His Gln Ser Glu Cys
    1985                1990                1995

Leu His Cys Ile Gln Val Ala Glu Ala Glu Val Lys Glu Lys Thr
    2000                2005                2010

Glu Leu Leu Gln Thr Leu Ser Ser Asp Val Ser Glu Leu Leu Lys
    2015                2020                2025

Asp Lys Thr His Leu Gln Glu Lys Leu Gln Ser Leu Glu Lys Asp
    2030                2035                2040

Ser Gln Ala Leu Ser Leu Thr Lys Cys Glu Leu Glu Asn Gln Ile
    2045                2050                2055

Ala Gln Leu Asn Lys Glu Lys Glu Leu Leu Val Lys Glu Ser Glu
    2060                2065                2070

Ser Leu Gln Ala Arg Leu Ser Glu Ser Asp Tyr Glu Lys Leu Asn
    2075                2080                2085

Val Ser Lys Ala Leu Glu Ala Ala Leu Val Glu Lys Gly Glu Phe
    2090                2095                2100

Ala Leu Arg Leu Ser Ser Thr Gln Glu Glu Val His Gln Leu Arg
    2105                2110                2115

Arg Gly Ile Glu Lys Leu Arg Val Arg Ile Glu Ala Asp Glu Lys
    2120                2125                2130

Lys Gln Leu His Ile Ala Glu Lys Leu Lys Glu Arg Glu Arg Glu
    2135                2140                2145

Asn Asp Ser Leu Lys Asp Lys Val Glu Asn Leu Glu Arg Glu Leu
    2150                2155                2160

Gln Met Ser Glu Glu Asn Gln Glu Leu Val Ile Leu Asp Ala Glu
    2165                2170                2175

Asn Ser Lys Ala Glu Val Glu Thr Leu Lys Thr Gln Ile Glu Glu
    2180                2185                2190

Met Ala Arg Ser Leu Lys Val Phe Glu Leu Asp Leu Val Thr Leu
    2195                2200                2205

Arg Ser Glu Lys Glu Asn Leu Thr Lys Gln Ile Gln Glu Lys Gln
    2210                2215                2220

Gly Gln Leu Ser Glu Leu Asp Lys Leu Leu Ser Ser Phe Lys Ser
    2225                2230                2235

Leu Leu Glu Glu Lys Glu Gln Ala Glu Ile Gln Ile Lys Glu Glu
    2240                2245                2250
```

```
Ser Lys Thr Ala Val Glu Met Leu Gln Asn Gln Leu Lys Glu Leu
2255                2260                2265

Asn Glu Ala Val Ala Ala Leu Cys Gly Asp Gln Glu Ile Met Lys
2270                2275                2280

Ala Thr Glu Gln Ser Leu Asp Pro Pro Ile Glu Glu His Gln
2285                2290                2295

Leu Arg Asn Ser Ile Glu Lys Leu Arg Ala Arg Leu Glu Ala Asp
2300                2305                2310

Glu Lys Lys Gln Leu Cys Val Leu Gln Gln Leu Lys Glu Ser Glu
2315                2320                2325

His His Ala Asp Leu Leu Lys Gly Arg Val Glu Asn Leu Glu Arg
2330                2335                2340

Glu Leu Glu Ile Ala Arg Thr Asn Gln Glu His Ala Ala Leu Glu
2345                2350                2355

Ala Glu Asn Ser Lys Gly Glu Val Glu Thr Leu Lys Ala Lys Ile
2360                2365                2370

Glu Gly Met Thr Gln Ser Leu Arg Gly Leu Glu Leu Asp Val Val
2375                2380                2385

Thr Ile Arg Ser Glu Lys Glu Asn Leu Thr Asn Glu Leu Gln Lys
2390                2395                2400

Glu Gln Glu Arg Ile Ser Glu Leu Glu Ile Ile Asn Ser Ser Phe
2405                2410                2415

Glu Asn Ile Leu Gln Glu Lys Glu Gln Glu Lys Val Gln Met Lys
2420                2425                2430

Glu Lys Ser Ser Thr Ala Met Glu Met Leu Gln Thr Gln Leu Lys
2435                2440                2445

Glu Leu Asn Glu Arg Val Ala Ala Leu His Asn Asp Gln Glu Ala
2450                2455                2460

Cys Lys Ala Lys Glu Gln Asn Leu Ser Ser Gln Val Glu Cys Leu
2465                2470                2475

Glu Leu Glu Lys Ala Gln Leu Leu Gln Gly Leu Asp Glu Ala Lys
2480                2485                2490

Asn Asn Tyr Ile Val Leu Gln Ser Ser Val Asn Gly Leu Ile Gln
2495                2500                2505

Glu Val Glu Asp Gly Lys Gln Lys Leu Glu Lys Lys Asp Glu Glu
2510                2515                2520

Ile Ser Arg Leu Lys Asn Gln Ile Gln Asp Gln Glu Gln Leu Val
2525                2530                2535

Ser Lys Leu Ser Gln Val Glu Gly Glu His Gln Leu Trp Lys Glu
2540                2545                2550

Gln Asn Leu Glu Leu Arg Asn Leu Thr Val Glu Leu Glu Gln Lys
2555                2560                2565

Ile Gln Val Leu Gln Ser Lys Asn Ala Ser Leu Gln Asp Thr Leu
2570                2575                2580

Glu Val Leu Gln Ser Ser Tyr Lys Asn Leu Glu Asn Glu Leu Glu
2585                2590                2595

Leu Thr Lys Met Asp Lys Met Ser Phe Val Glu Lys Val Asn Lys
2600                2605                2610

Met Thr Ala Lys Glu Thr Glu Leu Gln Arg Glu Met His Glu Met
2615                2620                2625

Ala Gln Lys Thr Ala Glu Leu Gln Glu Glu Leu Ser Gly Glu Lys
2630                2635                2640
```

```
Asn Arg Leu Ala Gly Glu Leu Gln Leu Leu Glu Glu Ile Lys
        2645                2650                2655

Ser Ser Lys Asp Gln Leu Lys Glu Leu Thr Leu Glu Asn Ser Glu
        2660                2665                2670

Leu Lys Lys Ser Leu Asp Cys Met His Lys Asp Gln Val Glu Lys
        2675                2680                2685

Glu Gly Lys Val Arg Glu Glu Ile Ala Glu Tyr Gln Leu Arg Leu
        2690                2695                2700

His Glu Ala Glu Lys Lys His Gln Ala Leu Leu Leu Asp Thr Asn
        2705                2710                2715

Lys Gln Tyr Glu Val Glu Ile Gln Thr Tyr Arg Glu Lys Leu Thr
        2720                2725                2730

Ser Lys Glu Glu Cys Leu Ser Ser Gln Lys Leu Glu Ile Asp Leu
        2735                2740                2745

Leu Lys Ser Ser Lys Glu Glu Leu Asn Asn Ser Leu Lys Ala Thr
        2750                2755                2760

Thr Gln Ile Leu Glu Glu Leu Lys Lys Thr Lys Met Asp Asn Leu
        2765                2770                2775

Lys Tyr Val Asn Gln Leu Lys Lys Glu Asn Glu Arg Ala Gln Gly
        2780                2785                2790

Lys Met Lys Leu Leu Ile Lys Ser Cys Lys Gln Leu Glu Glu Glu
        2795                2800                2805

Lys Glu Ile Leu Gln Lys Glu Leu Ser Gln Leu Gln Ala Ala Gln
        2810                2815                2820

Glu Lys Gln Lys Thr Gly Thr Val Met Asp Thr Lys Val Asp Glu
        2825                2830                2835

Leu Thr Thr Glu Ile Lys Glu Leu Lys Glu Thr Leu Glu Glu Lys
        2840                2845                2850

Thr Lys Glu Ala Asp Glu Tyr Leu Asp Lys Tyr Cys Ser Leu Leu
        2855                2860                2865

Ile Ser His Glu Lys Leu Glu Lys Ala Lys Glu Met Leu Glu Thr
        2870                2875                2880

Gln Val Ala His Leu Cys Ser Gln Gln Ser Lys Gln Asp Ser Arg
        2885                2890                2895

Gly Ser Pro Leu Leu Gly Pro Val Val Pro Gly Pro Ser Pro Ile
        2900                2905                2910

Pro Ser Val Thr Glu Lys Arg Leu Ser Ser Gly Gln Asn Lys Ala
        2915                2920                2925

Ser Gly Lys Arg Gln Arg Ser Ser Gly Ile Trp Glu Asn Gly Arg
        2930                2935                2940

Gly Pro Thr Pro Ala Thr Pro Glu Ser Phe Ser Lys Lys Ser Lys
        2945                2950                2955

Lys Ala Val Met Ser Gly Ile His Pro Ala Glu Asp Thr Glu Gly
        2960                2965                2970

Thr Glu Phe Glu Pro Glu Gly Leu Pro Glu Val Val Lys Lys Gly
        2975                2980                2985

Phe Ala Asp Ile Pro Thr Gly Lys Thr Ser Pro Tyr Ile Leu Arg
        2990                2995                3000

Arg Thr Thr Met Ala Thr Arg Thr Ser Pro Arg Leu Ala Ala Gln
        3005                3010                3015

Lys Leu Ala Leu Ser Pro Leu Ser Leu Gly Lys Glu Asn Leu Ala
        3020                3025                3030
```

```
Glu  Ser  Ser  Lys  Pro  Thr  Ala  Gly  Gly  Ser  Arg  Ser  Gln  Lys  Val
     3035                3040                3045

Lys  Val  Ala  Gln  Arg  Ser  Pro  Val  Asp  Ser  Gly  Thr  Ile  Leu  Arg
     3050                3055                3060

Glu  Pro  Thr  Thr  Lys  Ser  Val  Pro  Val  Asn  Asn  Leu  Pro  Glu  Arg
     3065                3070                3075

Ser  Pro  Thr  Asp  Ser  Pro  Arg  Glu  Gly  Leu  Arg  Val  Lys  Arg  Gly
     3080                3085                3090

Arg  Leu  Val  Pro  Ser  Pro  Lys  Ala  Gly  Leu  Glu  Ser  Asn  Gly  Ser
     3095                3100                3105

Glu  Asn  Cys  Lys  Val  Gln
     3110
```

<210> SEQ ID NO 13
<211> LENGTH: 94
<212> TYPE: PRT
<213> ORGANISM: Artificial Sequence
<220> FEATURE:
<223> OTHER INFORMATION: depicts amino acid sequence for Neutrophil
      defensin 1

<400> SEQUENCE: 13

```
Met  Arg  Thr  Leu  Ala  Ile  Leu  Ala  Ala  Ile  Leu  Leu  Val  Ala  Leu  Gln
1                    5                   10                      15

Ala  Gln  Ala  Glu  Pro  Leu  Gln  Ala  Arg  Ala  Asp  Glu  Val  Ala  Ala
                20                  25                  30

Pro  Glu  Gln  Ile  Ala  Ala  Asp  Ile  Pro  Glu  Val  Val  Val  Ser  Leu  Ala
             35                  40                  45

Trp  Asp  Glu  Ser  Leu  Ala  Pro  Lys  His  Pro  Gly  Ser  Arg  Lys  Asn  Met
50                       55                  60

Ala  Cys  Tyr  Cys  Arg  Ile  Pro  Ala  Cys  Ile  Ala  Gly  Glu  Arg  Arg  Tyr
65                       70                      75                      80

Gly  Thr  Cys  Ile  Tyr  Gln  Gly  Arg  Leu  Trp  Ala  Phe  Cys  Cys
                 85                      90
```

<210> SEQ ID NO 14
<211> LENGTH: 646
<212> TYPE: PRT
<213> ORGANISM: Artificial Sequence
<220> FEATURE:
<223> OTHER INFORMATION: depicts amino acid sequence for Isoform 2 of
      Heat shock cognate 71 kDa protein or HSP7C

<400> SEQUENCE: 14

```
Met  Ser  Lys  Gly  Pro  Ala  Val  Gly  Ile  Asp  Leu  Gly  Thr  Thr  Tyr  Ser
1                    5                   10                      15

Cys  Val  Gly  Val  Phe  Gln  His  Gly  Lys  Val  Glu  Ile  Ile  Ala  Asn  Asp
                20                  25                  30

Gln  Gly  Asn  Arg  Thr  Thr  Pro  Ser  Tyr  Val  Ala  Phe  Thr  Asp  Thr  Glu
             35                  40                  45

Arg  Leu  Ile  Gly  Asp  Ala  Ala  Lys  Asn  Gln  Val  Ala  Met  Asn  Pro  Thr
50                       55                  60

Asn  Thr  Val  Phe  Asp  Ala  Lys  Arg  Leu  Ile  Gly  Arg  Arg  Phe  Asp  Asp
65                       70                      75                      80

Ala  Val  Val  Gln  Ser  Asp  Met  Lys  His  Trp  Pro  Phe  Met  Val  Val  Asn
                 85                      90                      95

Asp  Ala  Gly  Arg  Pro  Lys  Val  Gln  Val  Glu  Tyr  Lys  Gly  Glu  Thr  Lys
                100                     105                     110
```

```
Ser Phe Tyr Pro Glu Val Ser Met Val Leu Thr Lys Met Lys
    115                 120                 125

Glu Ile Ala Glu Ala Tyr Leu Gly Lys Thr Val Thr Asn Ala Val Val
130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ala Ile Ala Tyr Gly Leu Asp Lys Lys Val Gly Ala Glu
                180                 185                 190

Arg Asn Val Leu Ile Phe Asp Leu Gly Gly Gly Thr Phe Asp Val Ser
                195                 200                 205

Ile Leu Thr Ile Glu Asp Gly Ile Phe Glu Val Lys Ser Thr Ala Gly
                210                 215                 220

Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Ile Glu Ile Asp Ser Leu Tyr
                275                 280                 285

Glu Gly Ile Asp Phe Tyr Thr Ser Ile Thr Arg Ala Arg Phe Glu Glu
                290                 295                 300

Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
                325                 330                 335

Val Gly Gly Ser Thr Arg Ile Pro Lys Ile Gln Lys Leu Leu Gln Asp
                340                 345                 350

Phe Phe Asn Gly Lys Glu Leu Asn Lys Ser Ile Asn Pro Asp Glu Ala
                355                 360                 365

Val Ala Tyr Gly Ala Ala Val Gln Ala Ala Ile Leu Ser Gly Asp Lys
                370                 375                 380

Ser Glu Asn Val Gln Asp Leu Leu Leu Leu Asp Val Thr Pro Leu Ser
385                 390                 395                 400

Leu Gly Ile Glu Thr Ala Gly Gly Val Met Thr Val Leu Ile Lys Arg
                405                 410                 415

Asn Thr Thr Ile Pro Thr Lys Gln Thr Gln Thr Phe Thr Thr Tyr Ser
                420                 425                 430

Asp Asn Gln Pro Gly Val Leu Ile Gln Val Tyr Glu Gly Glu Arg Ala
                435                 440                 445

Met Thr Lys Asp Asn Asn Leu Leu Gly Lys Phe Glu Leu Thr Gly Ile
                450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Ser Ala Val Asp Lys Ser Thr Gly
                485                 490                 495

Lys Glu Asn Lys Ile Thr Ile Thr Asn Asp Lys Gly Arg Leu Ser Lys
                500                 505                 510

Glu Asp Ile Glu Arg Met Val Gln Glu Ala Glu Lys Tyr Lys Ala Glu
                515                 520                 525
```

```
Asp Glu Lys Gln Arg Asp Lys Val Ser Ser Lys Asn Ser Leu Glu Ser
            530                 535                 540

Tyr Ala Phe Asn Met Lys Ala Thr Val Glu Asp Glu Lys Leu Gln Gly
545                 550                 555                 560

Lys Ile Asn Asp Glu Asp Lys Gln Lys Ile Leu Asp Lys Cys Asn Glu
                565                 570                 575

Ile Ile Asn Trp Leu Asp Lys Asn Gln Thr Ala Glu Lys Glu Glu Phe
                580                 585                 590

Glu His Gln Gln Lys Glu Leu Glu Lys Val Cys Asn Pro Ile Ile Thr
            595                 600                 605

Lys Leu Tyr Gln Ser Ala Gly Gly Met Pro Gly Gly Met Pro Gly Gly
            610                 615                 620

Phe Pro Gly Gly Gly Ala Pro Pro Ser Gly Gly Ala Ser Ser Gly Pro
625                 630                 635                 640

Thr Ile Glu Glu Val Asp
                645

<210> SEQ ID NO 15
<211> LENGTH: 248
<212> TYPE: PRT
<213> ORGANISM: Artificial Sequence
<220> FEATURE:
<223> OTHER INFORMATION: depicts amino acid sequence for Mannose-binding
      protein C

<400> SEQUENCE: 15

Met Ser Leu Phe Pro Ser Leu Pro Leu Leu Leu Leu Ser Met Val Ala
1               5                   10                  15

Ala Ser Tyr Ser Glu Thr Val Thr Cys Glu Asp Ala Gln Lys Thr Cys
                20                  25                  30

Pro Ala Val Ile Ala Cys Ser Ser Pro Gly Ile Asn Gly Phe Pro Gly
            35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
            115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
            195                 200                 205

Asn Glu Gly Glu Pro Asn Asn Ala Gly Ser Asp Glu Asp Cys Val Leu
    210                 215                 220
```

```
Leu Leu Lys Asn Gly Gln Trp Asn Asp Val Pro Cys Ser Thr Ser His
225                 230                 235                 240

Leu Ala Val Cys Glu Phe Pro Ile
            245
```

<210> SEQ ID NO 16
<211> LENGTH: 93
<212> TYPE: PRT
<213> ORGANISM: Artificial Sequence
<220> FEATURE:
<223> OTHER INFORMATION: depicts amino acid sequence for Protein S100-A8

<400> SEQUENCE: 16

```
Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
            85                  90
```

<210> SEQ ID NO 17
<211> LENGTH: 414
<212> TYPE: PRT
<213> ORGANISM: Artificial Sequence
<220> FEATURE:
<223> OTHER INFORMATION: depicts amino acid sequence for Serpin A12

<400> SEQUENCE: 17

```
Met Asn Pro Thr Leu Gly Leu Ala Ile Phe Leu Ala Val Leu Leu Thr
1               5                   10                  15

Val Lys Gly Leu Leu Lys Pro Ser Phe Ser Pro Arg Asn Tyr Lys Ala
            20                  25                  30

Leu Ser Glu Val Gln Gly Trp Lys Gln Arg Met Ala Ala Lys Glu Leu
        35                  40                  45

Ala Arg Gln Asn Met Asp Leu Gly Phe Lys Leu Leu Lys Lys Leu Ala
    50                  55                  60

Phe Tyr Asn Pro Gly Arg Asn Ile Phe Leu Ser Pro Leu Ser Ile Ser
65                  70                  75                  80

Thr Ala Phe Ser Met Leu Cys Leu Gly Ala Gln Asp Ser Thr Leu Asp
            85                  90                  95

Glu Ile Lys Gln Gly Phe Asn Phe Arg Lys Met Pro Glu Lys Asp Leu
        100                 105                 110

His Glu Gly Phe His Tyr Ile Ile His Glu Leu Thr Gln Lys Thr Gln
        115                 120                 125

Asp Leu Lys Leu Ser Ile Gly Asn Thr Leu Phe Ile Asp Gln Arg Leu
    130                 135                 140

Gln Pro Gln Arg Lys Phe Leu Glu Asp Ala Lys Asn Phe Tyr Ser Ala
145                 150                 155                 160

Glu Thr Ile Leu Thr Asn Phe Gln Asn Leu Glu Met Ala Gln Lys Gln
            165                 170                 175
```

Ile Asn Asp Phe Ile Ser Gln Lys Thr His Gly Lys Ile Asn Asn Leu
            180                 185                 190

Ile Glu Asn Ile Asp Pro Gly Thr Val Met Leu Leu Ala Asn Tyr Ile
            195                 200                 205

Phe Phe Arg Ala Arg Trp Lys His Glu Phe Asp Pro Asn Val Thr Lys
210                 215                 220

Glu Glu Asp Phe Phe Leu Glu Lys Asn Ser Ser Val Lys Val Pro Met
225                 230                 235                 240

Met Phe Arg Ser Gly Ile Tyr Gln Val Gly Tyr Asp Asp Lys Leu Ser
            245                 250                 255

Cys Thr Ile Leu Glu Ile Pro Tyr Gln Lys Asn Ile Thr Ala Ile Phe
            260                 265                 270

Ile Leu Pro Asp Glu Gly Lys Leu Lys His Leu Glu Lys Gly Leu Gln
            275                 280                 285

Val Asp Thr Phe Ser Arg Trp Lys Thr Leu Leu Ser Arg Arg Val Val
            290                 295                 300

Asp Val Ser Val Pro Arg Leu His Met Thr Gly Thr Phe Asp Leu Lys
305                 310                 315                 320

Lys Thr Leu Ser Tyr Ile Gly Val Ser Lys Ile Phe Glu Glu His Gly
            325                 330                 335

Asp Leu Thr Lys Ile Ala Pro His Arg Ser Leu Lys Val Gly Glu Ala
            340                 345                 350

Val His Lys Ala Glu Leu Lys Met Asp Glu Arg Gly Thr Glu Gly Ala
            355                 360                 365

Ala Gly Thr Gly Ala Gln Thr Leu Pro Met Glu Thr Pro Leu Val Val
            370                 375                 380

Lys Ile Asp Lys Pro Tyr Leu Leu Leu Ile Tyr Ser Glu Lys Ile Pro
385                 390                 395                 400

Ser Val Leu Phe Leu Gly Lys Ile Val Asn Pro Ile Gly Lys
            405                 410

<210> SEQ ID NO 18
<211> LENGTH: 426
<212> TYPE: PRT
<213> ORGANISM: Artificial Sequence
<220> FEATURE:
<223> OTHER INFORMATION: depicts amino acid sequence for Synaptotagmin-13

<400> SEQUENCE: 18

Met Val Leu Ser Val Pro Val Ile Ala Leu Gly Ala Thr Leu Gly Thr
1               5                   10                  15

Ala Thr Ser Ile Leu Ala Leu Cys Gly Val Thr Cys Leu Cys Arg His
            20                  25                  30

Met His Pro Lys Lys Gly Leu Leu Pro Arg Asp Gln Asp Pro Asp Leu
            35                  40                  45

Glu Lys Ala Lys Pro Ser Leu Leu Gly Ser Ala Gln Gln Phe Asn Val
        50                  55                  60

Lys Lys Ser Thr Glu Pro Val Gln Pro Arg Ala Leu Leu Lys Phe Pro
65                  70                  75                  80

Asp Ile Tyr Gly Pro Arg Pro Ala Val Thr Ala Pro Glu Val Ile Asn
            85                  90                  95

Tyr Ala Asp Tyr Ser Leu Arg Ser Thr Glu Glu Pro Thr Ala Pro Ala
            100                 105                 110

Ser Pro Gln Pro Pro Asn Asp Ser Arg Leu Lys Arg Gln Val Thr Glu
            115                 120                 125

Glu Leu Phe Ile Leu Pro Gln Asn Gly Val Val Glu Asp Val Cys Val
            130                 135                 140

Met Glu Thr Trp Asn Pro Glu Lys Ala Ala Ser Trp Asn Gln Ala Pro
145                 150                 155                 160

Lys Leu His Tyr Cys Leu Asp Tyr Asp Cys Gln Lys Ala Glu Leu Phe
            165                 170                 175

Val Thr Arg Leu Glu Ala Val Thr Ser Asn His Asp Gly Gly Cys Asp
            180                 185                 190

Cys Tyr Val Gln Gly Ser Val Ala Asn Arg Thr Gly Ser Val Glu Ala
            195                 200                 205

Gln Thr Ala Leu Lys Lys Arg Gln Leu His Thr Thr Trp Glu Glu Gly
            210                 215                 220

Leu Val Leu Pro Leu Ala Glu Glu Leu Pro Thr Ala Thr Leu Thr
225                 230                 235                 240

Leu Thr Leu Arg Thr Cys Asp Arg Phe Ser Arg His Ser Val Ala Gly
            245                 250                 255

Glu Leu Arg Leu Gly Leu Asp Gly Thr Ser Val Pro Leu Gly Ala Ala
            260                 265                 270

Gln Trp Gly Glu Leu Lys Thr Ser Ala Lys Glu Pro Ser Ala Gly Ala
            275                 280                 285

Gly Glu Val Leu Leu Ser Ile Ser Tyr Leu Pro Ala Ala Asn Arg Leu
            290                 295                 300

Leu Val Val Leu Ile Lys Ala Lys Asn Leu His Ser Asn Gln Ser Lys
305                 310                 315                 320

Glu Leu Leu Gly Lys Asp Val Ser Val Lys Val Thr Leu Lys His Gln
            325                 330                 335

Ala Arg Lys Leu Lys Lys Lys Gln Thr Lys Arg Ala Lys His Lys Ile
            340                 345                 350

Asn Pro Val Trp Asn Glu Met Ile Met Phe Glu Leu Pro Asp Asp Leu
            355                 360                 365

Leu Gln Ala Ser Ser Val Glu Leu Glu Val Leu Gly Gln Asp Asp Ser
            370                 375                 380

Gly Gln Ser Cys Ala Leu Gly His Cys Ser Leu Gly Leu His Thr Ser
385                 390                 395                 400

Gly Ser Glu Arg Ser His Trp Glu Glu Met Leu Lys Asn Pro Arg Arg
            405                 410                 415

Gln Ile Ala Met Trp His Gln Leu His Leu
            420                 425

<210> SEQ ID NO 19
<211> LENGTH: 335
<212> TYPE: PRT
<213> ORGANISM: Artificial Sequence
<220> FEATURE:
<223> OTHER INFORMATION: depicts amino acid sequence for Isoform 2 of
      Tubulin alpha-1B chain

<400> SEQUENCE: 19

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

```
Asp Gly Gln Met Pro Ser Asp Lys Thr Ile Gly Gly Asp Asp Ser
            35                  40                  45

Phe Asn Thr Phe Phe Ser Glu Thr Gly Ala Gly Lys His Val Pro Arg
     50                  55                  60

Ala Val Phe Val Asp Leu Glu Pro Thr Val Ile Asp Glu Val Arg Thr
 65                  70                  75                  80

Gly Thr Tyr Arg Gln Leu Phe His Pro Glu Gln Leu Ile Thr Gly Lys
                 85                  90                  95

Glu Asp Ala Ala Asn Asn Tyr Ala Arg Gly His Tyr Thr Asn Leu Asn
                100                 105                 110

Arg Leu Ile Ser Gln Ile Val Ser Ser Ile Thr Ala Ser Leu Arg Phe
            115                 120                 125

Asp Gly Ala Leu Asn Val Asp Leu Thr Glu Phe Gln Thr Asn Leu Val
        130                 135                 140

Pro Tyr Pro Arg Ile His Phe Pro Leu Ala Thr Tyr Ala Pro Val Ile
145                 150                 155                 160

Ser Ala Glu Lys Ala Tyr His Glu Gln Leu Ser Val Ala Glu Ile Thr
                165                 170                 175

Asn Ala Cys Phe Glu Pro Ala Asn Gln Met Val Lys Cys Asp Pro Arg
            180                 185                 190

His Gly Lys Tyr Met Ala Cys Cys Leu Leu Tyr Arg Gly Asp Val Val
        195                 200                 205

Pro Lys Asp Val Asn Ala Ala Ile Ala Thr Ile Lys Thr Lys Arg Ser
210                 215                 220

Ile Gln Phe Val Asp Trp Cys Pro Thr Gly Phe Lys Val Gly Ile Asn
225                 230                 235                 240

Tyr Gln Pro Pro Thr Val Val Pro Gly Gly Asp Leu Ala Lys Val Gln
                245                 250                 255

Arg Ala Val Cys Met Leu Ser Asn Thr Thr Ala Ile Ala Glu Ala Trp
            260                 265                 270

Ala Arg Leu Asp His Lys Phe Asp Leu Met Tyr Ala Lys Arg Ala Phe
        275                 280                 285

Val His Trp Tyr Val Gly Glu Gly Met Glu Glu Gly Glu Phe Ser Glu
    290                 295                 300

Ala Arg Glu Asp Met Ala Ala Leu Glu Lys Asp Tyr Glu Glu Val Gly
305                 310                 315                 320

Val Asp Ser Val Glu Gly Glu Gly Glu Glu Gly Glu Glu Tyr
                325                 330                 335

<210> SEQ ID NO 20
<211> LENGTH: 140
<212> TYPE: PRT
<213> ORGANISM: Artificial Sequence
<220> FEATURE:
<223> OTHER INFORMATION: depicts amino acid sequence for Profilin-1

<400> SEQUENCE: 20

Met Ala Gly Trp Asn Ala Tyr Ile Asp Asn Leu Met Ala Asp Gly Thr
 1               5                  10                  15

Cys Gln Asp Ala Ala Ile Val Gly Tyr Lys Asp Ser Pro Ser Val Trp
            20                  25                  30

Ala Ala Val Pro Gly Lys Thr Phe Val Asn Ile Thr Pro Ala Glu Val
        35                  40                  45

Gly Val Leu Val Gly Lys Asp Arg Ser Ser Phe Tyr Val Asn Gly Leu
    50                  55                  60
```

```
Thr Leu Gly Gly Gln Lys Cys Ser Val Ile Arg Asp Ser Leu Leu Gln
 65                  70                  75                  80

Asp Gly Glu Phe Ser Met Asp Leu Arg Thr Lys Ser Thr Gly Gly Ala
                 85                  90                  95

Pro Thr Phe Asn Val Thr Val Thr Lys Thr Asp Lys Thr Leu Val Leu
            100                 105                 110

Leu Met Gly Lys Glu Gly Val His Gly Gly Leu Ile Asn Lys Lys Cys
        115                 120                 125

Tyr Glu Met Ala Ser His Leu Arg Arg Ser Gln Tyr
    130                 135                 140

<210> SEQ ID NO 21
<211> LENGTH: 433
<212> TYPE: PRT
<213> ORGANISM: Artificial Sequence
<220> FEATURE:
<223> OTHER INFORMATION: depicts amino acid sequence for Adenylyl
      cyclase-associated protein

<400> SEQUENCE: 21

Met Ala Asp Met Gln Asn Leu Val Glu Arg Leu Glu Arg Ala Glu Tyr
 1               5                  10                  15

Leu Lys Ile Ser Lys Glu Ile Gly Gly Asp Val Gln Lys His Ala Glu
             20                  25                  30

Met Val His Thr Gly Leu Lys Leu Glu Arg Ala Leu Leu Val Thr Ala
         35                  40                  45

Ser Gln Cys Gln Gln Pro Ala Glu Asn Lys Leu Ser Asp Leu Leu Ala
 50                  55                  60

Pro Ile Ser Glu Gln Ile Lys Glu Val Ile Thr Phe Arg Glu Lys Asn
 65                  70                  75                  80

Arg Gly Ser Lys Leu Phe Asn His Leu Ser Ala Val Ser Glu Ser Ile
                 85                  90                  95

Gln Ala Leu Gly Trp Val Ala Met Ala Pro Lys Pro Gly Pro Tyr Val
            100                 105                 110

Lys Glu Met Asn Asp Ala Ala Met Phe Tyr Thr Asn Arg Val Leu Lys
        115                 120                 125

Glu Tyr Lys Asp Val Asp Lys Lys His Val Asp Trp Val Lys Ala Tyr
    130                 135                 140

Leu Ser Ile Trp Thr Glu Leu Gln Ala Tyr Ile Lys Glu Phe His Thr
145                 150                 155                 160

Thr Gly Leu Ala Trp Ser Lys Thr Gly Pro Val Ala Lys Glu Leu Ser
                165                 170                 175

Gly Leu Pro Ser Gly Pro Ser Ala Gly Ser Gly Pro Pro Pro Pro Pro
            180                 185                 190

Pro Gly Pro Pro Pro Pro Val Ser Thr Ser Ser Gly Ser Asp Glu
        195                 200                 205

Ser Ala Ser Arg Ser Ala Leu Phe Ala Gln Ile Asn Gln Gly Glu Ser
    210                 215                 220

Ile Thr His Ala Leu Lys His Val Ser Asp Asp Met Lys Thr His Lys
225                 230                 235                 240

Asn Pro Ala Leu Lys Ala Gln Ser Gly Pro Val Arg Ser Gly Pro Lys
                245                 250                 255

Pro Phe Ser Ala Pro Lys Pro Gln Thr Ser Pro Ser Pro Lys Arg Ala
            260                 265                 270
```

```
Thr Lys Lys Glu Pro Ala Val Leu Glu Leu Glu Gly Lys Lys Trp Arg
        275                 280                 285

Val Glu Asn Gln Glu Asn Val Ser Asn Leu Val Ile Glu Asp Thr Glu
290                 295                 300

Leu Lys Gln Val Ala Tyr Ile Tyr Lys Cys Val Asn Thr Thr Leu Gln
305                 310                 315                 320

Ile Lys Gly Lys Ile Asn Ser Ile Thr Val Asp Asn Cys Lys Lys Leu
                325                 330                 335

Gly Leu Val Phe Asp Asp Val Val Gly Ile Val Glu Ile Ile Asn Ser
                340                 345                 350

Lys Asp Val Lys Val Gln Val Met Gly Lys Val Pro Thr Ile Ser Ile
                355                 360                 365

Asn Lys Thr Asp Gly Cys His Ala Tyr Leu Ser Lys Asn Ser Leu Asp
        370                 375                 380

Cys Glu Ile Val Ser Ala Lys Ser Ser Glu Met Asn Val Leu Ile Pro
385                 390                 395                 400

Thr Glu Gly Gly Asp Phe Asn Glu Phe Pro Val Pro Glu Gln Phe Lys
                405                 410                 415

Thr Leu Trp Asn Gly Gln Lys Leu Val Thr Thr Val Thr Glu Ile Ala
                420                 425                 430

Gly
```

<210> SEQ ID NO 22
<211> LENGTH: 338
<212> TYPE: PRT
<213> ORGANISM: Artificial Sequence
<220> FEATURE:
<223> OTHER INFORMATION: depicts amino acid sequence for C-myc promoter-
      binding protein 1

<400> SEQUENCE: 22

```
Met Asp Gly Thr Glu Asn Lys Ser Lys Phe Gly Ala Asn Ala Ile Leu
1               5                   10                  15

Gly Val Ser Leu Ala Val Cys Lys Ala Gly Ala Val Glu Lys Gly Val
                20                  25                  30

Pro Leu Tyr Arg His Ile Ala Asp Leu Ala Gly Asn Ser Glu Val Ile
            35                  40                  45

Leu Pro Val Pro Ala Phe Asn Val Ile Asn Gly Gly Ser His Ala Gly
        50                  55                  60

Asn Lys Leu Ala Met Gln Glu Phe Met Ile Leu Pro Val Gly Ala Ala
65                  70                  75                  80

Asn Phe Arg Glu Ala Met Arg Ile Gly Ala Glu Val Tyr His Asn Leu
                85                  90                  95

Lys Asn Val Ile Lys Glu Lys Tyr Gly Lys Asp Ala Thr Asn Val Gly
                100                 105                 110

Asp Glu Gly Gly Phe Ala Pro Asn Ile Leu Glu Asn Lys Glu Gly Leu
            115                 120                 125

Glu Leu Leu Lys Thr Ala Ile Gly Lys Ala Gly Tyr Thr Asp Lys Val
130                 135                 140

Val Ile Gly Met Asp Val Ala Ala Ser Glu Phe Phe Arg Ser Gly Lys
145                 150                 155                 160

Tyr Asp Leu Asp Phe Lys Ser Pro Asp Pro Ser Arg Tyr Ile Ser
                165                 170                 175

Pro Asp Gln Leu Ala Asp Leu Tyr Lys Ser Phe Ile Lys Asp Tyr Pro
            180                 185                 190
```

```
Val Val Ser Ile Glu Asp Pro Phe Asp Gln Asp Asp Trp Gly Ala Trp
        195                 200                 205

Gln Lys Phe Thr Ala Ser Ala Gly Ile Gln Val Val Gly Asp Asp Leu
        210                 215                 220

Thr Val Thr Asn Pro Lys Arg Ile Ala Lys Ala Val Asn Glu Lys Ser
225                 230                 235                 240

Cys Asn Cys Leu Leu Leu Lys Val Asn Gln Ile Gly Ser Val Thr Glu
                245                 250                 255

Ser Leu Gln Ala Cys Lys Leu Ala Gln Ala Asn Gly Trp Gly Val Met
        260                 265                 270

Val Ser His Arg Ser Gly Glu Thr Glu Asp Thr Phe Ile Ala Asp Leu
        275                 280                 285

Val Val Gly Leu Cys Thr Gly Gln Ile Lys Thr Gly Ala Pro Cys Arg
        290                 295                 300

Ser Glu Arg Leu Ala Lys Tyr Asn Gln Leu Leu Arg Ile Glu Glu Glu
305                 310                 315                 320

Leu Gly Ser Lys Ala Lys Phe Ala Gly Arg Asn Phe Arg Asn Pro Leu
                325                 330                 335

Ala Lys

<210> SEQ ID NO 23
<211> LENGTH: 569
<212> TYPE: PRT
<213> ORGANISM: Artificial Sequence
<220> FEATURE:
<223> OTHER INFORMATION: depicts amino acid sequence for Mitochondrial
      heat shock 60kD protein 1 variant 1

<400> SEQUENCE: 23

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
        100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
        130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
        180                 185                 190

Val Gly Arg Lys Gly Val Ile Thr Val Lys Asp Gly Lys Thr Leu Asn
        195                 200                 205
```

Asp Glu Leu Glu Ile Ile Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
            245                 250                 255

Ile Val Pro Ala Leu Glu Ile Ala Asn Ala His Arg Lys Pro Leu Val
        260                 265                 270

Ile Ile Ala Glu Asp Val Asp Gly Glu Ala Leu Ser Thr Leu Val Leu
    275                 280                 285

Asn Arg Leu Lys Val Gly Leu Gln Val Val Ala Val Lys Ala Pro Gly
290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
            325                 330                 335

Val Gln Pro His Asp Leu Gly Lys Val Gly Glu Val Ile Val Thr Lys
        340                 345                 350

Asp Asp Ala Met Leu Leu Lys Gly Lys Gly Asp Lys Ala Gln Ile Glu
    355                 360                 365

Lys Arg Ile Gln Glu Ile Ile Glu Gln Leu Asp Val Thr Thr Ser Glu
370                 375                 380

Tyr Glu Lys Gly Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
            405                 410                 415

Lys Lys Asp Arg Val Thr Asp Ala Leu Asn Ala Thr Arg Ala Ala Val
        420                 425                 430

Glu Glu Gly Ile Val Leu Gly Gly Gly Cys Ala Leu Leu Arg Cys Ile
    435                 440                 445

Pro Ala Leu Asp Ser Leu Thr Pro Ala Asn Glu Asp Gln Lys Ile Gly
450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
            485                 490                 495

Ser Ser Ser Glu Val Gly Tyr Asp Ala Met Ala Gly Asp Phe Val Asn
        500                 505                 510

Met Val Glu Lys Gly Ile Ile Asp Pro Thr Lys Val Val Arg Thr Ala
    515                 520                 525

Leu Leu Asp Ala Ala Gly Val Ala Ser Leu Leu Thr Thr Ala Glu Val
530                 535                 540

Val Val Thr Glu Ile Pro Lys Glu Glu Lys Asp Pro Gly Met Gly Ala
545                 550                 555                 560

Met Gly Gly Met Gly Gly Gly Met Phe
            565

<210> SEQ ID NO 24
<211> LENGTH: 114
<212> TYPE: PRT
<213> ORGANISM: Artificial Sequence
<220> FEATURE:
<223> OTHER INFORMATION: depicts amino acid sequence for Protein S100

<400> SEQUENCE: 24

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Val His Glu
            85                  90                  95

Gly Asp Glu Gly Pro Gly His His His Lys Pro Gly Leu Gly Glu Gly
            100                 105                 110

Thr Pro

<210> SEQ ID NO 25
<211> LENGTH: 284
<212> TYPE: PRT
<213> ORGANISM: Artificial Sequence
<220> FEATURE:
<223> OTHER INFORMATION: depicts amino acid sequence for Beta
      tropomyosin isoform

<400> SEQUENCE: 25

Met Asp Ala Ile Lys Lys Lys Met Gln Met Leu Lys Leu Asp Lys Glu
1               5                   10                  15

Asn Ala Ile Asp Arg Ala Glu Gln Ala Glu Ala Asp Lys Lys Gln Ala
            20                  25                  30

Glu Asp Arg Cys Lys Gln Leu Glu Glu Glu Gln Gln Ala Leu Gln Lys
        35                  40                  45

Lys Leu Lys Gly Thr Glu Asp Glu Val Glu Lys Tyr Ser Glu Ser Val
50                  55                  60

Lys Glu Ala Gln Glu Lys Leu Glu Gln Ala Glu Lys Lys Ala Thr Asp
65                  70                  75                  80

Ala Glu Ala Asp Val Ala Ser Leu Asn Arg Arg Ile Gln Leu Val Glu
            85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Asn Arg Ala Met Lys Asp Glu Glu Lys Met Glu Leu Gln
130                 135                 140

Glu Met Gln Leu Lys Glu Ala Lys His Ile Ala Glu Asp Ser Asp Arg
145                 150                 155                 160

Lys Tyr Glu Glu Val Ala Arg Lys Leu Val Ile Leu Glu Gly Glu Leu
            165                 170                 175

Glu Arg Ser Glu Glu Arg Ala Glu Val Ala Glu Ser Arg Ala Arg Gln
            180                 185                 190

Leu Glu Glu Glu Leu Arg Thr Met Asp Gln Ala Leu Lys Ser Leu Met
        195                 200                 205

Ala Ser Glu Glu Glu Tyr Ser Thr Lys Glu Asp Lys Tyr Glu Glu Glu
210                 215                 220

```
Ile Lys Leu Leu Glu Glu Lys Leu Lys Glu Ala Glu Thr Arg Ala Glu
225                 230                 235                 240

Phe Ala Glu Arg Ser Val Ala Lys Leu Glu Lys Thr Ile Asp Asp Leu
                245                 250                 255

Glu Asp Glu Val Tyr Ala Gln Lys Met Lys Tyr Lys Ala Ile Ser Glu
                260                 265                 270

Glu Leu Asp Asn Ala Leu Asn Asp Ile Thr Ser Leu
            275                 280

<210> SEQ ID NO 26
<211> LENGTH: 97
<212> TYPE: PRT
<213> ORGANISM: Artificial Sequence
<220> FEATURE:
<223> OTHER INFORMATION: depicts amino acid sequence for Peroxiredoxin-1

<400> SEQUENCE: 26

Met Ser Ser Gly Asn Ala Lys Ile Gly His Pro Ala Pro Asn Phe Lys
1               5                   10                  15

Ala Thr Ala Asp Glu Gly Ile Ser Phe Arg Gly Leu Phe Ile Ile Asp
                20                  25                  30

Asp Lys Gly Ile Leu Arg Gln Ile Thr Val Asn Asp Leu Pro Val Gly
            35                  40                  45

Arg Ser Val Asp Glu Thr Leu Arg Leu Val Gln Ala Phe Gln Phe Thr
        50                  55                  60

Asp Lys His Gly Glu Val Cys Pro Ala Gly Trp Lys Pro Gly Ser Asp
65                  70                  75                  80

Thr Ile Lys Pro Asp Val Gln Lys Ser Lys Glu Tyr Phe Ser Lys Gln
                85                  90                  95

Lys
```

PLATELET LYSATE, AND METHOD OF PREPARATION THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is SEQUENCE_LISTING_790161_402USPC. The text file is 115 KB, was created on Aug. 4, 2021, and is being submitted electronically via EFS-Web.

FIELD OF INVENTION

The present disclosure relates to cell culture media and cell culture media supplements, which are non-human-animal-product free. More particularly, the present disclosure relates to platelet lysate obtained from a mixture of umbilical cord blood (UCB) and maternal blood (MB) platelet-rich plasma. Further, the present disclosure relates to a method of preparing said platelet lysate.

BACKGROUND OF INVENTION

Cell and tissue culture media are typically composed of mineral salts, amino acids and vitamins to aid cultivation and propagation of cells under ex-vivo conditions. Generally, these media are supplemented with non-human, animal-derived additives such as non-human animal-derived Fetal Bovine Serum (FBS). An alternative means of supplementing cell culture media is by means of feeder layer cells.

However, the use of FBS is marred with challenges that include: (a) a cocktail of undefined qualitative and quantitative composition; (b) a considerable ethical concern; (c) global supply and availability of FBS can be highly fluctuating; and (d) batch-to-batch variation of FBS. Further, use of FBS in therapeutic applications is a major and undesirable risk for patients in clinical settings and discouraged by regulatory authorities to limit the risk of zoonoses and xenogeneic immune reactions in the transplanted host.

Thus, there is a need to find an appropriate replacement, with the required efficacy and efficiency for culturing cells such as stem cells and cells for therapeutic applications. One such growth supplement may be platelet-derived products, e.g., platelet lysates.

Platelet-based biomaterials such as platelet gel, platelet glue and platelet rich plasma have been reported to be used in the treatment of chronic ulcers and are a potential source in orthopaedics to facilitate healing and enhancing bone-grafting following implantation (refer Shaheen A et al., *Austin J Dermatolog*, 2018, 5(1):1085-1094, Wellington K Hsu et al., *J Am Acad Orthop Surg* 2013; 21:739-748, and Mlynarek R A et al. *Am J Orthop.* 2016; 45(4):290-294, 326).

The methods for isolation and enrichment of platelet fraction from blood and further preparation of platelet lysates have relied upon centrifugation as a means to segregate platelet-rich plasma fraction from a blood sample, such as peripheral blood from a human subject from the cell pellet and platelet-poor plasma fraction, for example.

CN106236779 discloses a method for preparing platelet-rich plasma (PRP) from cord blood.

Bernardi et al. (*Journal of translational medicine*, 2017; vol. 15, 1 90.1, doi:10.1186/s12967-017-1185-9), discloses that the production method used to release platelet factors significantly affects the enrichment in growth factors and overall product performance.

EP2757879A1 discloses a method for producing a platelet lysate with a maximum level of safety by subjecting platelets to a pathogen inactivation.

US9700583B2 discloses a method of autologous mesenchymal stem cells (MSCs) isolation from a patient, expansion in presence of platelet rich paste obtained by centrifugation and subsequent implantation into said patient.

Shirzad et al. (*Cell journal*, 2017; 19(3):403-414), discloses culture supplements devoid of animal-derived products and provides umbilical cord blood-platelet lysate (UCB-PL) as a standard substitute for FBS and human peripheral blood-PL (PB-PL).

Kwok et al. (*Br J Haematol.* 2007; 137(5):468-74), discloses that the presence of maternal plasma/human serum albumin (HSA) in the efficient purification and culture of $CD34^+$ cells derived from human umbilical cord blood.

US20110123503A1 discloses platelet fractions which can be obtained from placental blood.

The above described methods for preparation of platelet fractions, including platelet lysates have drawbacks and problems in terms of loss of logistics, costs and amount of cellular (platelet) damage due to the use of centrifugation/apheresis manufacturing procedures on blood products. Further, the loss of discarded umbilical cord blood (UCB) or discarded maternal blood (MB) isolated for testing or otherwise, which potentially comprises a plethora of growth factors and differentiation factors that may be exploited for therapeutic applications in cell and tissue cultures meant for implantation into patients and beyond has potential economic benefits.

Gifford et al. (*PLoS ONE*, 2018; 13(1): e0190827), discloses the logistical complications and potential cellular damage associated with centrifugation/apheresis manufacturing of blood products.

Hence, there remains a problem of finding an appropriate method for platelet fraction isolation, providing a viable and economical source for isolation.

All publications mentioned in this document are incorporated fully by reference.

SUMMARY OF THE INVENTION

In an aspect of the present invention, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to at least one sedimentation to obtain an umbilical cord blood (UCB) derived platelet-rich plasma; (d) obtaining a maternal blood (MB) sample, and subjecting the maternal blood (MB) sample to at least one sedimentation to collect maternal blood (MB) derived platelet-rich plasma; (e) mixing the umbilical cord blood (UCB) derived platelet-rich plasma of step (c) and the maternal blood (MB) derived platelet-rich plasma of step (d) to obtain an umbilical cord blood and maternal blood (UCB+MB) platelet-rich plasma mixture; (f) storing the umbilical cord blood and maternal blood (UCB+MB) platelet-rich plasma mixture to obtain a frozen umbilical cord blood and maternal blood (UCB+MB) platelet-rich plasma mixture; and (g) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets.

In another aspect of the present invention, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to a first and a second sedimentation to obtain plasma comprising umbilical cord blood (UCB) derived platelets; (d) subjecting the plasma of step (c) to a third sedimentation to obtain an umbilical cord blood (UCB) derived platelet-rich plasma; (e) obtaining a maternal blood (MB) sample, and subjecting the maternal blood (MB) sample to sedimentation to collect maternal blood (MB) derived platelet-rich plasma; (f) mixing the umbilical cord blood (UCB) derived platelet-rich plasma of step (d) and the maternal blood (MB) derived platelet-rich plasma of step (e) to obtain an umbilical cord blood and maternal blood (UCB+MB) platelet-rich plasma mixture; (g) storing the UCB+MB platelet-rich plasma mixture at a temperature in a range of −70° C. to −86° C. for a time in a range of 24 hours to 96 hours to obtain a frozen UCB+MB platelet-rich plasma mixture; and (h) subjecting the frozen UCB+MB platelet-rich plasma mixture to freeze-thaw cycles to obtain a lysate from a combination of umbilical cord blood derived platelets and maternal blood derived platelets.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

DETAILED DESCRIPTION OF THE INVENTION

Figure 1:
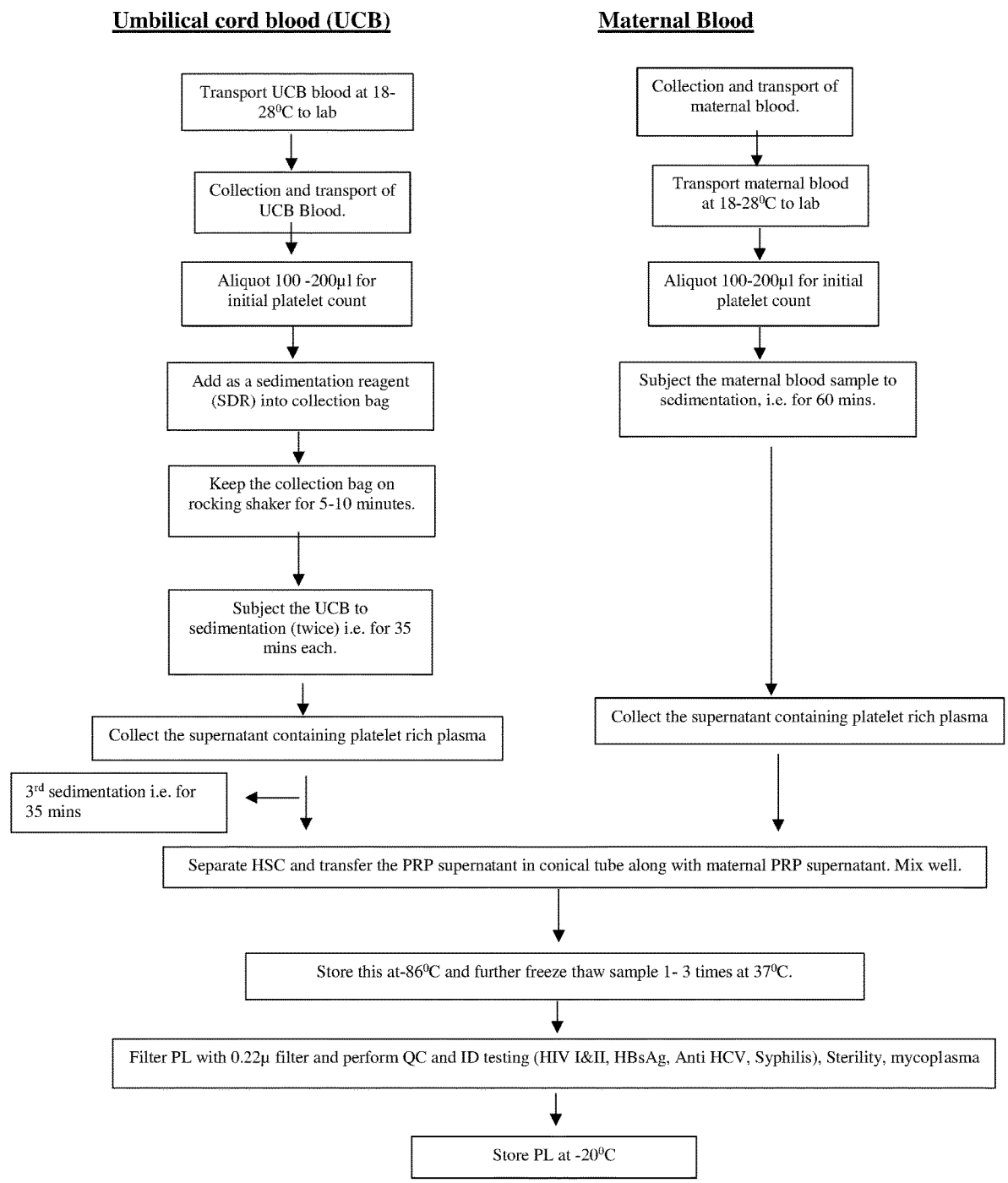
FIG. 1 illustrates a flow-chart of the process summary of obtaining the unique umbilical cord blood and maternal blood (UCB+MB) platelet lysate (PL), in accordance with an embodiment of the present disclosure.

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" as used herein means "including but not limited to". "Including" and "including but not limited to" are used interchangeably.

The term "at least" as used herein means not less than the following amount.

The term "lysate" as used herein includes cellular lysates, platelet lysates, plasma and combinations thereof that are procured following cellular lysis. Cellular lysis may be brought on by freeze/thaw cycles, osmotic changes, other physical and chemical means known in the field.

The term "platelet-rich plasma" (PRP) as used herein means the less light plasma portion of the blood that comprises platelets in a concentration above one million per microliter.

The term "platelet lysate" as used herein means cell lysates produced from regular platelet transfusion units by lysis.

The term "platelet" as used herein refers to cells which are small a-nucleated structures of hematopoietic origin which contribute to homeostasis and wound healing by secreting growth factors and cytokines. They are produced by the fragmentation of megakaryocytes and released into the bloodstream, where they circulate for 7-10 days before being replaced.

The term "subject" as used herein refers to any vertebrate animal and does not merely cover human. Human subjects have been used to exemplify the invention but, said exemplification should not be considered in any way limiting to the scope of the subject matter as covered under the term subject.

The term "umbilical cord blood" (UCB) as used herein means the blood that remains in the placenta and in the attached umbilical cord after childbirth. Cord blood is collected because it contains stem cells, which can be used to treat hematopoietic and genetic disorders. Generally, a lot of this rich biological resource is discarded. The preferred source is human. The term "in-vitro assays" depict the assays which can be done in in-vitro. The application of such assays can range from therapeutics, diagnostics to predictive studies for development.

The process for umbilical cord blood (UCB) collection entails: (a) confirming the identity of a subject, (b) cleaning the segment of the umbilical cord with 10% povidone Iodine and 70% alcohol (Ethyl Alcohol/Isopropyl Alcohol) thrice alternately, swabbing away from the collection area, before collection, (c) after spirit evaporates, removing outer gloves to prevent contamination, (d) holding cord blood collection bag with sterile inner gloves, (e) inserting one end of a needle in the umbilical cord vein near the cord clamp and the other end into a blood collection bag, (f) gently and properly mixing the cord blood flowing into the collection bag with an anticoagulant, (g) once umbilical cord appears empty and whitish and all blood has been removed, stopping the blood link through the needle, checking for leakage, if any, and cleaning the blood collection bag with the collected umbilical cord blood (UCB) with sterile gauze. The preferred source is human.

The term "maternal blood" (MB) as used herein means the blood collected from a mother pre- and post-delivery. The maternal blood (MB) collection may take place at a time immediately before/after cord blood collection, at the time of admission for delivery (after initiation of labour) or before transfusion/infusion of any intravenous fluid (colloids/crystalloids/blood products). The preferred source is human.

The term "umbilical cord blood and maternal blood" (UCB+MB) as used herein means any combination of an umbilical cord blood and maternal blood. Said combination may come from autologous and/or allogenic sources. The preferred source is human.

The term "sedimentation" as used herein refers to the tendency for heavier particles in suspension to settle out of the fluid in which they are entrained and come to rest against a barrier like bottom of a container. Such a motion through the fluid may be in response to the forces acting on them, which may include, gravity, centrifugal acceleration, or electromagnetism.

The term "at least one sedimentation" as used herein refers to a minimum of one sedimentation.

The term "at least two sedimentations" as used herein refers to a minimum of two sedimentations.

The term "sedimentation mixture" as used herein means any mix of substances that leads to and/or aids a sedimentation process, where heavier components of the mixture settle on the bottom, due to gravity, leaving the lighter components amenable for separation such as by decantation or pipetting.

The term "sedimentation reagent" as used herein means any substance that aids coagulation or aggregation of particles or components in suspension to form heavier particles that then come to rest against a barrier like bottom of a container due to the forces acting on them such as gravity.

As used herein, a sedimentation reagent such as Ficoll-Hipaque, Hespan®, Pentastarch, and combinations thereof.

The term "frozen umbilical cord blood and maternal blood (UCB+MB) platelet-rich plasma mixture" as used herein means the mixture obtained by freezing said mixture at a temperature in a range of −70° C. to −86° C. for a time in a range of 24 hours to 96 hours.

The term "freeze-thaw cycle" as used herein refers to a process of rapid freeze (bringing to low temperature) and slow thaw (bringing to high temperature) that results in cell death and/or cell lysis. Often repeated a set number of times according to the size and nature of cells being treated. As used herein the freeze-thaw cycles may range from 1 to 5, and the temperature for freezing ranges from −70° C. to −86° C. and the temperature for thawing ranges from 30° C. to 40° C.

The term "platelets/ml" as used herein refers to the number of platelets per milliliter of a fluid. Preferably said fluid is plasma.

The term "a combination of umbilical cord blood derived platelets and maternal blood derived platelets" as used herein refers to mixing or combination of platelets derived from processing umbilical cord blood and maternal blood, whether allogenous or autogenous by origin, and mixed in a ratio in a range of 10:1 to 30:1, and preferably, 10:1 to 26:1.

The term "infectious diseases" as used herein refers to diseases caused by pathogens such as microbes including HIV I and II, HBs, HCV, Syphilis, Mycoplasma etc.

The term "enriched" as used herein refers to enhancement in concentration of an amount of a component per volume containing said component following processing steps. For platelet-rich plasma as used herein, to obtain umbilical cord blood and maternal blood (UCB+MB) 'enriched' platelet lysate, the platelets in platelet-rich plasma obtained by combination of umbilical cord blood and maternal blood (UCB+MB) are in a range of $0.3 \times 10^9$ to $1.5 \times 10^9$ platelets/ml.

The term "culturing" as used herein refers to maintaining (tissues, cells, bacteria, etc.) in conditions suitable for growth, propagation, expansion, differentiation and the like, in a specially prepared nutrient medium under supervised conditions.

The term "cells" as used herein refers to any type of stem cells, progenitor cells and differentiated cells. Preferably, the cells are selected from a group consisting of progenitor cells, osteoblasts, chondrocytes, buccal epithelial cells, dermal culture, cord tissue-derived mesenchymal stem cells, bone marrow-derived mesenchymal stem cells, and cardiomyocytes. The cells are preferably human by origin.

The term "therapeutic applications" means applications including, but not limited to, mesenchymal stem cells derived from human umbilical cord tissue, osteoblasts differentiated from bone marrow derived mesenchymal stem cells, cardiomyocytes differentiated from human umbilical cord tissue derived mesenchymal stem cells, islets cells of pancreas differentiated from human umbilical cord tissue derived mesenchymal stem cells, chondrocytes from human cartilage biopsy and buccal biopsy derived dermal fibroblasts. The therapeutic applications are further incorporated with but not limiting to, certain biomaterials or cell-gel techniques or methods thereof.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

To address the problems encountered with use of FBS, the present disclosure provides an optimized non-animal origin cell and tissue culture supplement in the form of an umbilical cord blood and maternal blood (UCB+MB) enriched platelet lysate. Further, the present disclosure provides a method for preparing a lysate, wherein the lysate is the umbilical cord blood and maternal blood (UCB+MB) enriched platelet lysate.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to at least one sedimentation to obtain an umbilical cord blood (UCB) derived platelet-rich plasma; (d) obtaining a maternal blood (MB) sample, and subjecting the maternal blood (MB) sample to at least one sedimentation to collect maternal blood (MB) derived platelet-rich plasma; (e) mixing the umbilical cord blood (UCB) derived platelet-rich plasma of step (c) and the maternal blood (MB) derived platelet-rich plasma of step (d) to obtain an umbilical cord blood and maternal blood (UCB+MB) platelet-rich plasma mixture; (f) storing the umbilical cord blood and maternal blood (UCB+MB) platelet-rich plasma mixture to obtain a frozen umbilical cord blood and maternal blood (UCB×MB) platelet-rich plasma mixture; and (g) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets. In another embodiment of the present disclosure, the umbilical cord blood (UCB) sedimentation mixture is subjected to at least two sedimentations. In yet another embodiment of the present disclosure, the storing is done at a temperature in a range of −70° C. to −86° C. to obtain the frozen umbilical cord blood and maternal blood (UCB+MB) platelet-rich plasma mixture. In a further embodiment of the present disclosure, the storing is done for a time in a range of 24 hours to 96 hours. In a supplementary embodiment of the present disclosure, the lysate is selected from a group consisting of cell lysate, platelet lysate, plasma and combinations thereof. In an alternate embodiment of the present disclosure, the lysate is a platelet lysate.

In an embodiment of the present disclosure, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to a first and a second sedimentation to obtain plasma comprising umbilical cord blood (UCB) derived platelets; (d) subjecting the plasma of step (c) to a third sedimentation to obtain an umbilical cord blood (UCB) derived platelet-rich plasma; (e) obtaining a maternal blood (MB) sample, and subjecting the maternal blood (MB) sample to sedimentation to collect maternal blood (MB) derived platelet-rich plasma; (f) mixing the umbilical cord blood (UCB) derived platelet-rich plasma of step (d) and the maternal blood (MB) derived platelet-rich plasma of step (e) to obtain an umbilical cord blood and maternal blood (UCB+MB) platelet-rich plasma mixture; (g) storing the umbilical cord blood and maternal blood (UCB+MB) platelet-rich plasma mixture at a temperature in a range of −70° C. to −86° C. for a time in a range of 24 hours to 96 hours to obtain a frozen umbilical cord blood and maternal blood (UCB+MB) platelet-rich plasma mixture; and (h) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets. In another embodiment of the present disclosure, lysate is selected from a group consisting of cell lysate, platelet lysate, plasma and combinations thereof. In an alternate embodiment of the present disclosure, the lysate is a platelet lysate.

In an embodiment of the present disclosure, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to at least one sedimentation to obtain an umbilical cord blood (UCB) derived platelet-rich plasma; (d) obtaining a maternal blood (MB) sample, and subjecting the maternal blood (MB) sample to at least one sedimentation to collect maternal blood (MB) derived platelet-rich plasma; (e) mixing the umbilical cord blood (UCB) derived platelet-rich plasma of step (c) and the maternal blood (MB) derived platelet-rich plasma of step (d) to obtain an umbilical cord blood and maternal blood (UCB+MB) platelet-rich plasma mixture; (f) storing the umbilical cord blood and maternal blood (UCB+MB) platelet-rich plasma mixture to obtain a frozen umbilical cord blood and maternal blood (UCB−MB) platelet-rich plasma mixture; and (g) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets, wherein the lysate is a platelet lysate, wherein the umbilical cord blood (UCB) sedimentation mixture comprises the umbilical cord blood (UCB) sample and the at least one sedimentation reagent is in a volume ratio of 3:1 to 9:1, or in a volume ratio of 4:1 to 8:1, or a volume ratio of 4.5:1 to 6:1, or in a volume ratio of 5:1. In another embodiment of the present disclosure, the lysate is selected from a group consisting of cell lysate, platelet lysate, plasma and combinations thereof. In an alternate embodiment of the present disclosure, the lysate is a platelet lysate. In another embodiment of the present disclosure, the at least one sedimentation is carried out at a temperature in a range of −70° C. to −86° C. for a time in a range of 24 hours to 96 hours. In a supplementary embodiment of the present disclosure, the umbilical cord blood (UCB) sample and maternal blood (MB) sample are independently subjected to an initial platelet count by withdrawing aliquot of 100-200 µl.

In an embodiment of the present disclosure, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to a first and a second sedimentation to obtain plasma comprising umbilical cord blood (UCB) derived platelets; (d) subjecting the plasma of step (c) to a third sedimentation to obtain an umbilical cord blood (UCB) derived platelet-rich plasma; (e) obtaining a maternal blood (MB) sample, and subjecting the maternal blood (MB) sample to sedimentation to collect maternal blood (MB) derived platelet-rich plasma; (f) mixing the umbilical cord blood (UCB) derived platelet-rich plasma of step (d) and the maternal blood (MB) derived platelet-rich plasma of step (e) to obtain an umbilical cord blood and maternal blood (UCB+MB) platelet-rich plasma mixture; (g) storing the umbilical cord blood and maternal blood (UCB+MB) platelet-rich plasma mixture at a temperature in a range of −70° C. to −86° C. for a time in a range of 24 hours to 96 hours to obtain a frozen umbilical cord blood and maternal blood (UCB+MB) platelet-rich plasma mixture; and (h) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets, wherein the first, the second and the third sedimentation are carried out for 25-55 minutes, or for 32-42 minutes, or for 35 minutes. In another embodiment of the present disclosure described herein, the storing of the umbilical cord blood and maternal blood (UCB+MB) platelet-rich plasma mixture is at a temperature of −86° C. for a time of 48 hours. In an auxiliary embodiment of the present disclosure described herein, the cord blood (UCB) sample and maternal blood (MB) sample are independently subjected to an initial platelet count by withdrawing aliquot of 100-200 µl. In an additional embodiment of the present disclosure as described herein, the lysate is selected from a group consisting of cell lysate, platelet lysate, plasma and combinations thereof.

In an embodiment of the present disclosure, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to a first and a second sedimentation to obtain plasma comprising umbilical cord blood (UCB) derived platelets; (d) subjecting the plasma of step (c) to a third sedimentation to obtain an umbilical cord blood (UCB) derived platelet-rich plasma; (e) obtaining a maternal blood (MB) sample, and subjecting the maternal blood (MB) sample to sedimentation to collect maternal blood (MB) derived platelet-rich plasma; (f) mixing the umbilical cord blood (UCB) derived platelet-rich plasma of step (d) and the maternal blood (MB) derived platelet-rich plasma of step (e) to obtain an umbilical cord blood and maternal blood (UCB+MB) platelet-rich plasma mixture; (g) storing the umbilical cord blood and maternal blood (UCB+MB) platelet-rich plasma mixture at a temperature in a range of −70° C. to −86° C. for a time in a range of 24 hours to 96 hours to obtain a frozen umbilical cord blood and maternal blood (UCB+MB) platelet-rich plasma mixture; and (h) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets, wherein the umbilical cord blood (UCB) sample is at least 100 ml and the maternal blood (MB) sample is in a range of 15 ml to 20 ml, or in a range of 80 ml to 120 ml and the maternal blood (MB) sample is in a range of 15 ml to 20 ml. In an auxiliary embodiment of the present disclosure, the storing of the umbilical cord blood and maternal blood (UCB+MB) platelet-rich plasma mixture is at a temperature of −86° C. for a time of 48 hours. In a supplementary embodiment of the present disclosure, the umbilical cord blood (UCB) sample and maternal blood (MB) sample are independently subjected to an initial platelet count by withdrawing aliquot of 100-200 µl. In an ancillary embodiment of the present disclosure, lysate is selected from a group consisting of cell lysate, platelet lysate, plasma and combinations thereof.

In an embodiment of the present disclosure, therein is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to a first and a second sedimentation to obtain plasma comprising umbilical cord blood (UCB) derived platelets; (d) subjecting the plasma of step (c) to a third sedimentation to obtain an umbilical cord blood (UCB) derived platelet-rich plasma; (e) obtaining a maternal blood (MB) sample, and subjecting the maternal blood (MB) sample to sedimentation to collect maternal blood (MB) derived platelet-rich plasma; (f) mixing the umbilical cord blood (UCB) derived platelet-rich plasma of step (d) and the maternal blood (MB) derived platelet-rich plasma of step (e) to obtain an umbilical cord blood and maternal blood (UCB+MB) platelet-rich plasma mixture; (g) storing the umbilical cord blood and maternal blood (UCB+MB) platelet-rich plasma mixture at a temperature of −86° C. for a time of 48 hours to obtain a frozen umbilical cord blood and maternal blood (UCB+MB) platelet-rich plasma mixture; and (h) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets, wherein the human umbilical cord blood (UCB) and maternal blood (MB) platelets are obtained from plasma which is considered as a bio-waste obtained after processing the cord blood. In an ancillary embodiment of the present disclosure, lysate is selected from a group consisting of cell lysate, platelet lysate, plasma and combinations thereof. Said bio-waste are discarded after delivery and tests. Further, said umbilical cord blood (UCB) and maternal blood (MB) are checked by infectious disease testing and only the samples free of contaminations and free from infectious diseases are selected for the preparation of platelet lysate.

In an embodiment of the present disclosure, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to a first and a second sedimentation to obtain plasma comprising umbilical cord blood (UCB) derived platelets; (d) subjecting the plasma of step (c) to a third sedimentation to obtain an umbilical cord blood (UCB) derived platelet-rich plasma; (e) obtaining a maternal blood (MB) sample, and subjecting the maternal blood (MB) sample to sedimentation to collect maternal blood (MB) derived platelet-rich plasma; (f) mixing the umbilical cord blood (UCB) derived platelet-rich plasma of step (d) and the maternal blood (MB) derived platelet-rich plasma of step (e) to obtain an umbilical cord blood and maternal blood (UCB+MB) platelet-rich plasma mixture; (g) storing the umbilical cord blood and maternal blood (UCB+MB) platelet-rich plasma mixture at a temperature in a range of −70° C. to −86° C. for a time in a range of 24 hours to 96 hours to obtain a frozen umbilical cord blood and maternal blood (UCB+MB) platelet-rich plasma mixture; and (h) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets, wherein the umbilical cord blood and maternal blood (UCB+MB) platelet-rich plasma mixture comprises platelets in a range of $0.3 \times 10^9$ to $1.5 \times 10^9$ platelets/ml, or $0.3 \times 10^9$ to $0.7 \times 10^9$ platelets/ml, or $0.3 \times 10^9$ to $0.5 \times 10^9$ platelets/ml.

In an embodiment of the present disclosure, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to a first and a second sedimentation to obtain plasma comprising umbilical cord blood (UCB) derived platelets; (d) subjecting the plasma of step (c) to a third sedimentation to obtain an umbilical cord blood (UCB) derived platelet-rich plasma; (e) obtaining a maternal blood (MB) sample, and subjecting the maternal blood (MB) sample to sedimentation to collect maternal blood (MB) derived platelet-rich plasma; (f) mixing the umbilical cord blood (UCB) derived platelet-rich plasma of step (d) and the maternal blood (MB) derived platelet-rich plasma of step (e) to obtain an umbilical cord blood and maternal blood (UCB+MB) platelet-rich plasma mixture; (g) storing the umbilical cord blood and maternal blood (UCB+MB) platelet-rich plasma mixture at a temperature in a range of −70° C. to −86° C. for a time in a range of 24 hours to 96 hours to obtain a frozen umbilical cord blood and maternal blood (UCB+MB) platelet-rich plasma mixture; and (h) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets, wherein the mixing of umbilical cord blood (UCB) derived platelet-rich plasma of step (d) and the maternal blood (MB) derived platelet-rich plasma of step (e) is done in a volume ratio having a range of 10:1 to 30:1, or 20:1 to 30:1.

In an embodiment of the present disclosure, there is provided a method for preparing a lysate as described herein, wherein the freeze-thaw cycles range from 1-5 or from 2-3.

In an embodiment of the present disclosure, there is provided a method for preparing a platelet lysate as described herein, wherein the freeze-thaw cycles range from 1-5 or from 2-3.

In an embodiment of the present disclosure, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to a first and a second sedimentation to obtain plasma comprising umbilical cord blood (UCB) derived platelets; (d) subjecting the plasma of step (c) to a third sedimentation to obtain an umbilical cord blood (UCB) derived platelet-rich plasma; (e) obtaining a maternal blood (MB) sample, and subjecting the maternal blood (MB) sample to sedimentation to collect maternal blood (MB) derived platelet-rich plasma; (f) mixing the umbilical cord blood (UCB) derived platelet-rich plasma of step (d) and the maternal blood (MB) derived platelet-rich plasma of step (e) to obtain an umbilical cord blood and maternal blood (UCB+MB) platelet-rich plasma mixture; (g) storing the umbilical cord blood and maternal blood (UCB+MB) platelet-rich plasma mixture at a temperature in a range of −70° C. to −86° C. for a time in a range of 24 hours to 96 hours to obtain a frozen umbilical cord blood and maternal blood (UCB+MB) platelet-rich plasma mixture; and (h) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets, wherein the at least one sedimentation reagent is selected from a group consisting of Ficoll-Hipaque, Hespan®, Pentastarch, and combinations thereof.

In an embodiment of the present disclosure, there is provided a method for preparing a lysate, said method comprising: (a) obtaining an umbilical cord blood (UCB) sample; (b) contacting the umbilical cord blood (UCB) sample with at least one sedimentation reagent to obtain an umbilical cord blood (UCB) sedimentation mixture; (c) subjecting the umbilical cord blood (UCB) sedimentation mixture to a first and a second sedimentation to obtain plasma comprising umbilical cord blood (UCB) derived platelets; (d) subjecting the plasma of step (c) to a third sedimentation to obtain an umbilical cord blood (UCB) derived platelet-rich plasma; (e) obtaining a maternal blood (MB) sample, and subjecting the maternal blood (MB) sample to sedimentation to collect maternal blood (MB) derived platelet-rich plasma; (f) mixing the umbilical cord blood (UCB) derived platelet-rich plasma of step (d) and the maternal blood (MB) derived platelet-rich plasma of step (e) to obtain an umbilical cord blood and maternal blood (UCB+MB) platelet-rich plasma mixture; (g) storing the umbilical cord blood and maternal blood (UCB+MB) platelet-rich plasma mixture at a temperature in a range of −70° C. to −86° C. for a time in a range of 24 hours to 96 hours to obtain a frozen umbilical cord blood and maternal blood (UCB+MB) platelet-rich plasma mixture; and (h) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets, and wherein subjecting the umbilical cord blood (UCB) sedimentation mixture to a first, a second, and a third sedimentation is done for at least 30 minutes, or for a time period in a range of 30-45 minutes. In a complementary embodiment of the present disclosure, subjecting the maternal blood sample (MB) sample to sedimentation is done for a time in a range of 50-70 minutes.

In an embodiment of the present disclosure, there is provided a method for preparing a lysate as described herein, wherein the lysate obtained is a platelet lysate, and wherein the platelet lysate is filtered using a 0.22μ filter.

In an embodiment of the present disclosure, there is provided a method for preparing a lysate as described herein, wherein the lysate obtained is subjected to screening for presence of infectious diseases (ID). In an auxiliary embodiment of the present disclosure, the screening involves testing for microbial testing, mycoplasma testing, and infectious diseases (ID) viz., HIV I and II antibodies, HBs Ag (surface antigen), HCV antibodies and Syphilis antibodies.

In an embodiment of the present disclosure, there is provided an umbilical cord blood and maternal blood (UCB+MB) enriched platelet lysate comprising: (a) a platelet lysate obtained from umbilical cord blood (UCB) derived platelet-rich plasma; and (b) a platelet lysate obtained from maternal blood (MB) derived platelet-rich plasma, wherein the umbilical cord blood derived platelets and the maternal blood derived platelets have a combined platelet count in a range of $0.3 \times 10^9$ to $1.5 \times 10^9$ platelets/ml, for use in culturing cells. In an auxiliary embodiment of the present disclosure, the culturing cells are selected from a group consisting of progenitor cells, osteoblasts, chondrocytes, buccal epithelial cells, dermal culture, cord tissue-derived mesenchymal stem cells, bone marrow-derived mesenchymal stem cells, and cardiomyocytes.

In an embodiment of the present disclosure, there is provided an umbilical cord blood and maternal blood (UCB+MB) enriched platelet lysate comprising: (a) a platelet lysate obtained from umbilical cord blood (UCB) derived platelet-rich plasma; and (b) a platelet lysate obtained from maternal blood (MB) derived platelet-rich plasma, wherein the umbilical cord blood derived platelets and the maternal blood derived platelets have a combined platelet count in a range of $0.3 \times 10^9$ to $1.5 \times 10^9$ platelets/ml, for use in therapeutic applications.

In an embodiment of the present disclosure, there is provided an umbilical cord blood and maternal blood (UCB+MB) enriched platelet lysate comprising: (a) a platelet lysate obtained from umbilical cord blood (UCB) derived platelet-rich plasma; and (b) a platelet lysate obtained from maternal blood (MB) derived platelet-rich plasma, wherein the umbilical cord blood derived platelets and the maternal blood derived platelets have a combined platelet count in a range of $0.3 \times 10^9$ to $1.5 \times 10^9$ platelets/ml, wherein said umbilical cord blood and maternal blood (UCB+MB) enriched platelet lysate is cryopreserved for a time in a range of 1 day to 12 months at a temperature in a range of $-70°$ C. to $-86°$ C. for use in culturing cells. In a further embodiment of the present disclosure, said umbilical cord blood and maternal blood (UCB+MB) enriched platelet lysate is cryopreserved for a time of 6 months at a temperature in a range of $-86°$ C. for use in culturing cells, or for a time of 12 months at a temperature in a range of $-86°$ C. for use in culturing cells. In an accompanying embodiment of the present disclosure, the umbilical cord blood and maternal blood (UCB+MB) enriched platelet lysate is for use in culturing cells, and wherein the cells are selected from a group consisting of progenitor cells, osteoblasts, chondrocytes, buccal epithelial cells, dermal culture, cord tissue-derived mesenchymal stem cells, bone marrow-derived mesenchymal stem cells, and cardiomyocytes.

In an embodiment of the present disclosure, there is provided an umbilical cord blood and maternal blood (UCB+MB) enriched platelet lysate comprising: (a) a platelet lysate obtained from umbilical cord blood (UCB) derived platelet-rich plasma; and (b) a platelet lysate obtained from maternal blood (MB) derived platelet-rich plasma, wherein the umbilical cord blood derived platelets and the maternal blood derived platelets have a combined platelet count in a range of $0.3 \times 10^9$ to $1.5 \times 10^9$ platelets/ml, wherein said umbilical cord blood and maternal blood (UCB+MB) enriched platelet lysate is cryopreserved for a time in a range of 1 day to 12 months at a temperature in a range of $-70°$ C. to $-86°$ C. for use in therapeutic applications.

In an embodiment of the present disclosure, there is provided an umbilical cord blood and maternal blood (UCB+MB) enriched platelet lysate comprising: (a) a platelet lysate obtained from umbilical cord blood (UCB) derived platelet-rich plasma; and (b) a platelet lysate obtained from maternal blood (MB) derived platelet-rich plasma, wherein the umbilical cord blood derived platelets and the maternal blood derived platelets have a combined platelet count in a range of $0.3 \times 10^9$ to $1.5 \times 10^9$ platelets/ml, wherein, the enriched platelet lysate is obtained by a method comprising: (i) obtaining an umbilical cord blood (UCB) sample; (ii) contacting the umbilical cord blood (UCB) sample with at least one sedimentation reagent to obtain an umbilical cord blood (UCB) sedimentation mixture; (iii) subjecting the umbilical cord blood (UCB) sedimentation mixture to a first and a second sedimentation to obtain plasma comprising umbilical cord blood (UCB) derived platelets; (iv) subjecting the plasma of step (iii) to a third sedimentation to obtain an umbilical cord blood (UCB) derived platelet-rich plasma; (v) obtaining a maternal blood (MB) sample, and subjecting the maternal blood (MB) sample to sedimentation to collect maternal blood (MB) derived platelet-rich plasma; (vi) mixing the umbilical cord blood (UCB) derived platelet-rich plasma of step (iv) and the maternal blood (MB) derived platelet-rich plasma of step (v) to obtain an umbilical cord blood and maternal blood (UCB+MB) platelet-rich plasma mixture; (vii) storing the umbilical cord blood and maternal blood (UCB+MB) platelet-rich plasma mixture at a temperature in a range of $-70°$ C. to $-86°$ C. for a time in a range of 24 hours to 96 hours to obtain a frozen umbilical cord blood and maternal blood (UCB+MB) platelet-rich plasma mixture; and (viii) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets, wherein the umbilical cord blood (UCB) sedimentation mixture comprises the umbilical cord blood (UCB) sample and the at least one sedimentation reagent is in a volume ratio of 3:1 to 9:1, or 4:1 to 8:1, or 4.5:1 to 6:1, or 5:1.

Although the subject matter has been described in considerable detail with reference to certain examples and implementations thereof, other implementations are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

The examples as presented herein describe the best working process of the present disclosure.

Example 1

Umbilical Cord Blood Collection

Umbilical cord blood (UCB) was collected from an identified subject. Before collection, the segment of the umbilical cord of said subject was cleaned with 10% povidone Iodine and 70% alcohol (Ethyl Alcohol/Isopropyl Alcohol) thrice alternately, swabbing away from the collection area. After the spirit evaporated, the outer gloves were removed to prevent contamination. Then the umbilical cord blood (UCB) collection bag was held with sterile inner gloves and a sterile needle was inserted into the umbilical cord vein near the cord clamp and said needle was connected to the umbilical cord blood (UCB) collection bag that held a sterile anticoagulant such as citrate-phosphate-dextrose solution. The flowing cord blood through the needle into the umbilical cord blood (UCB) collection bag was gently and properly mixed with the anticoagulant in the umbilical cord blood (UCB) collection bag. After the collection of maximal amounts of cord blood, till the umbilical cord ran empty and appeared whitish, multiple knots were tied at the opening end of the umbilical cord blood (UCB) collection bag after cutting the input from the needle with care and the collection bag was checked for leakage. The umbilical cord blood (UCB) collection bag was finally cleaned with sterile gauze pieces and used for transport to a cell processing centre. The collected umbilical cord blood (UCB) was transported to the cell processing centre at 18° C. to 28° C. within a period of less than 72 hours post-collection. After receiving the sample, umbilical cord blood (UCB) bag was cleaned with 70% IPA and then it was sealed and labelled.

Example 2

Maternal Blood Collection

The accuracy and identity of the subject mother was confirmed. Maternal blood (MB) sample was collected in a sterile vacutainer tube with a sterile anticoagulant such as EDTA. The collection of maternal blood (MB) sample was carried out at the time of admission for delivery (after initiation of labour) or before transfusion/infusion of any intravenous fluid (colloids/crystalloids/blood products) and immediately before/after cord blood collection. The collected maternal blood (MB) was transported to the cell processing centre at 18° C. to 28° C. within a period of less than 72 hours post-collection. After receiving the sample, maternal blood (MB) vacutainer tube was cleaned with 70% IPA and then it was sealed and labelled.

Example 3

Process for Preparation of Platelet Lysate

Steps for preparation of platelet lysate from umbilical cord blood (UCB) and maternal blood (MB) samples is represented in a flow-chart (refer FIG. 1). To begin, at the cell processing centre, an aliquot of 100-200 µl were withdrawn for initial platelet count from the labelled umbilical cord blood (UCB) bag and maternal blood (MB) vacutainer tube.

For processing the umbilical cord blood (UCB) bag, a calculated volume of sedimentation reagent, such as Ficoll-Hipaque, Hespan®, Pentastarch, etc., was withdrawn under sterile conditions and injected into the umbilical cord blood (UCB) collection bag and kept on a rocking shaker for 5-10 minutes. A processing bag was labelled and attached to the said umbilical cord blood (UCB) collection bag. The said umbilical cord blood (UCB) collection bag was subjected to a first and then a second sedimentation for 35 minutes each so as to allow Rouleax formation of the red blood cells (RBCs) for better separation of the RBCs from the plasma. After said sedimentations, with the use of auto volume expresser, umbilical cord blood (UCB) platelet-rich plasma was collected in the umbilical cord blood (UCB) processing bag. Further, the umbilical cord blood (UCB) platelet-rich plasma in the umbilical cord blood (UCB) processing bag was subjected to a third sedimentation for another 35 minutes to separate out hematopoietic stem cells (HSCs) from the plasma with the use of auto volume expresser and the final umbilical cord blood (UCB) derived platelet-rich plasma was collected in a 50 ml conical tube.

At the same time as the processing of umbilical cord blood (UCB), the maternal blood (MB) sample was kept for sedimentation for 60 minutes and then, the supernatant was collected to procure maternal blood (MB) derived platelet-rich plasma into a 50 ml conical tube.

The isolated umbilical cord blood (UCB) derived platelet-rich plasma and maternal blood (MB) derived platelet-rich plasma were mixed together and stored at −86° C. for 48 hours and further this mixture of platelet-rich plasma was taken through multiple cycles of freeze-thaw cycles ranging from 1-3 times to get to good quality platelet lysate (PL) called umbilical cord blood (UCB) plus maternal blood (MB) platelet lysate or UCB+MB platelet lysate. Said UCB+MB platelet lysate was filtered using a 0.22µ filter and tested for microbial sterility, mycoplasma and infectious diseases viz., HIV I and II antibodies, HBs Ag (surface antigen), HCV antibodies and Syphilis antibodies.

Using this method, from around 100 ml of umbilical cord blood (UCB), approximately 40 ml to 60 ml of umbilical cord blood (UCB) derived platelet lysate may be obtained and from around 15 ml to 20 ml of maternal blood, approximately 10 ml of maternal blood (MB) derived platelet lysate may be obtained.

Example 4

Validation of Sedimentation Time for Isolation of Platelets from Umbilical Cord Blood Example 4 analyzed three different time points used for isolation of platelets from human umbilical cord blood (UCB) samples, namely, 20 minutes, 35 minutes and 60 minutes. Sample size for the experiment was 5 umbilical cord blood (UCB) samples. Samples 1 to 5 refer to the UCB obtained from five subjects.

Table 1 presents umbilical cord blood (UCB) samples initial and final platelet counts (platelets/ml) recovered with different time periods of sedimentation with a sedimentation reagent (Hespan® which is 6% hetastarch in 0.9% sodium chloride solution). A total of 5 sample data have been represented in triplicates in said table. Herein, quantification having average and standard deviation were calculated of platelet counts of UCB.

TABLE 1

Results of Platelet count derived from UCB through Sedimentation process

| S. no | Sample no | Volume of cord Blood | Before Sedimentation Initial Count (Platelets/ml) | After Sedimentation Final Count (Platelets/ml) | | | | | | | | |
|---|---|---|---|---|---|---|---|---|---|---|---|---|
| | | | | 20 mins | | | 35 mins | | | 60 mins | | |
| | | | | Platelet | Recovery | Impurity# | Platelet | Recovery | Impurity# | Platelet | Recovery | Impurity# |
| 1 | Sample 1 | 98. ml | $0.19 \times 10^9$ | $0.19 \times 10^9$ | 100% | + | $0.18 \times 10^9$ | 94.73% | − | $0.15 \times 10^9$ | 78% | − |
| 2 | Sample 2 | 115 ml | $0.22 \times 10^9$ | $0.22 \times 10^9$ | 100% | + | $0.20 \times 10^9$ | 90.90% | − | $0.17 \times 10^9$ | 77% | − |
| 3 | Sample 3 | 86 ml | $0.17 \times 10^9$ | $0.16 \times 10^9$ | 94.11% | + | $0.16 \times 10^9$ | 94.11% | − | $0.14 \times 10^9$ | 82% | − |
| 4 | Sample 4 | 121 ml | $0.26 \times 10^9$ | $0.25 \times 10^9$ | 96.15% | + | $0.24 \times 10^9$ | 92.30% | − | $0.19 \times 10^9$ | 73% | − |
| 5 | Sample 5 | 92 ml | $0.20 \times 10^9$ | $0.20 \times 10^9$ | 100% | + | $0.20 \times 10^9$ | 100% | − | $0.16 \times 10^9$ | 80% | − | impurity refers to contamination of other cells in the platelets (+ Present; − absent)

*Inference: At different time points Platelet recovery was carried out.

From the table above, one can deduce that at 35 minutes of sedimentation platelet recovery was more than 90%, while at 20 mins recovery was high but mixed population along with platelets and RBC, WBCs and at 60 mins platelet recovery was very less (less than 85%). Also, there was no impurity after the sedimentation process.

Example 5

Validation for Volume of Sedimentation Reagent Used for Isolation of Platelets from Umbilical Cord Blood Example 5 analyzed volume ratio of cord blood along with sedimentation reagent used for isolation of platelets from human umbilical cord blood samples 2.5 ml UCB: 1 ml Sedimentation reagent(SDR)-Ratio-1; 5 ml UCB: 1 ml Sedimentation reagent (SDR)-Ratio-2; and 10 ml UCB: 1 ml Sedimentation reagent (SDR)-Ratio-3. Sample size for the experiment was 5 umbilical cord blood (UCB) samples. Each sample was divided into three parts.

Table 2 presents umbilical cord blood (UCB) samples initial and final platelet counts (platelets/ml) recovered with sedimentation using different volume ratios of UCB (ml) to sedimentation reagent (Hespan® which is 6% hetastarch in 0.9% sodium chloride solution). A total of 5 sample data have been represented in triplicates in said table. Herein, quantification having average and standard deviation were calculated of platelet counts of UCB.

TABLE 2

Results of Platelet count derived from UCB through Sedimentation process

| S.no | Sample no | Before Sedimentation Initial Count (Platelets/ml) | After Sedimentation Final Count (Platelets/ml) | | | | | |
|---|---|---|---|---|---|---|---|---|
| | | | Ratio-1 | Recovery | Ratio-2 | Recovery | Ratio-3 | Recovery |
| 1 | Sample 1 | $0.50 \times 10^8$ | $0.28 \times 10^8$ | 56% | $0.45 \times 10^8$ | 90.00% | $0.20 \times 10^8$ | 40.00% |
| 2 | Sample 2 | $0.40 \times 10^8$ | $0.30 \times 10^8$ | 60% | $0.38 \times 10^8$ | 95.00% | $0.20 \times 10^8$ | 50.00% |
| 3 | Sample 3 | $0.70 \times 10^8$ | $0.40 \times 10^8$ | 57% | $0.65 \times 10^8$ | 92.85% | $0.32 \times 10^8$ | 45.71% |
| 4 | Sample 4 | $0.50 \times 10^8$ | $0.20 \times 10^8$ | 40% | $0.48 \times 10^8$ | 96.00% | $0.21 \times 10^8$ | 42.00% |
| 5 | Sample 5 | $0.80 \times 10^8$ | $0.50 \times 10^8$ | 62% | $0.78 \times 10^8$ | 97.50% | $0.45 \times 10^8$ | 56.25% |

*Inference: At different volume ratios Platelet recovery was carried out.

From the table above, one can deduce that at 5:1 ratio of UCB: sedimentation reagent, platelet recovery was more than 90%, while at 2.5:1 and 10:1 ratios, the recovery was less than 60%. Therefore, the ratio of UCB to sedimentation reagent plays a critical role in platelet recovery. The present Example highlights the experimental efforts to arrive at a specific ratio.

Table 3 below shows the recovery percentage of platelets through sedimentation process from maternal blood (MB)

| S.no | Sample no | Volume of cord Blood maternal blood | Before Sedimentation Initial Count (Platelets/ml) | 60 mins (After sedimentation) Platelet count | Recovery | Impurity # |
|---|---|---|---|---|---|---|
| 1 | Sample 1 | 10 | $0.19 \times 10^9$ | $0.15 \times 10^9$ | 78% | — |
| 2 | Sample 2 | 115 ml | $0.22 \times 10^9$ | $0.17 \times 10^9$ | 77% | — |
| 3 | Sample 3 | 86 ml | $0.17 \times 10^9$ | $0.14 \times 10^9$ | 82% | — |
| 4 | Sample 4 | 121 ml | $0.26 \times 10^9$ | $0.19 \times 10^9$ | 73% | — |
| 5 | Sample 5 | 92 ml | $0.20 \times 10^9$ | $0.16 \times 10^9$ | 80% | — |

It can be observed from the Table above that the recovery of samples from the sedimentation process was above 75% in case of maternal blood.

Example 6

Comparison of Processing of Umbilical Cord Blood (UCB) and Maternal Blood (MB)
Blood Sample Collection:

Umbilical cord blood (UCB, about 150 ml) was drawn from the umbilical cord tissue of the five healthy subjects into the collection bag containing citrate-phosphate-dextrose as an anticoagulant. The umbilical cord blood (UCB) collection bag was then transported to the cell processing centre (CPC) at 18-28° C. along with 10 ml of maternal blood in (MB) vacutainer tube.
Isolation of Platelet Lysate from UCB and MB Using Sedimentation:

The method described in Example 3 was employed for isolation of platelets from UCB and MB to obtain UCB, MB and UCB+MB platelet lysates.

Isolation of Platelet Lysate from UCB Using Centrifugation:

The procedure followed has been taken from Shaheen A et al., Wellington K Hsu et al., and Mlynarek R A et al. (refer Shaheen A "Platelet Rich Plasma (PRP) for Treatment Non-Healing Ulcers: A Review Study," Austin J Dermatolog, 2018, 5(1):1085-1094, Wellington K Hsu et al. "Platelet-rich Plasma in Orthopaedic Applications: Evidence-based Recommendations for Treatment," J Am Acad Orthop Surg 2013; 21:739-748, and Mlynarek R A et al. "Platelet-Rich Plasma (PRP) in Orthopedic Sports Medicine," Am J Orthop. 2016 May; 45(4):290-294, 326).

The aliquots from platelet-rich plasma from UCB and MB before and after sedimentation process showed that the average platelet count remained almost the same, even with the decrease in plasma volume.

Table 4 presents (a) the umbilical cord blood (UCB) derived platelet count before and after sedimentation; and (b) the maternal blood (MB) derived platelet count before and after sedimentation. A total of 5 sample data have been represented in triplicates in said table. Herein, quantification having average and standard deviation were calculated of platelet counts of UCB and MB respectively.

TABLE 4

Results of Platelet count derived from UCB and maternal Blood through (MB) Sedimentation process

| Sample Number | Triplets | UCB derived Platelet | | | | | Maternal Blood derived Platelet | | | | | Total platelets received (UCB + MB) |
|---|---|---|---|---|---|---|---|---|---|---|---|---|
| | | Before Sedimentation | | After Sedimentation | | | Before Sedimentation | | After Sedimentation | | | |
| | | Initial Volume (ml) | Initial Count (Platelets/ml) | Final Volume (ml) | Final Count (Platelets/ml) | Recovery (%) | Initial Volume (ml) | Initial Count (Platelets/ml) | Final Volume (ml) | Final Count (Platelets/ml) | Recovery (%) | |
| Sample 1 | S.1.1 | 87.7 | $0.16 \times 10^9$ | 50 | $0.19 \times 10^9$ | | 10 | $0.60 \times 10^9$ | 5 | $0.61 \times 10^9$ | | |
| | S.1.2 | | $0.18 \times 10^9$ | | $0.14 \times 10^9$ | | | $0.64 \times 10^9$ | | $0.63 \times 10^9$ | | |
| | S.1.3 | | $0.17 \times 10^9$ | | $0.18 \times 10^9$ | | | $0.65 \times 10^9$ | | $0.62 \times 10^9$ | | |
| Average | | | $0.17 \times 10^9$ | | $0.17 \times 10^9$ | 100% | | $0.63 \times 10^9$ | | $0.62 \times 10^9$ | 98% | $0.21 \times 10^9$ |
| STDEV | | | ±0.01 | | ±0.02 | | | ±0.02 | | ±0.01 | | |
| Sample 2 | S.2.1 | 143 | $0.26 \times 10^9$ | 80 | $0.24 \times 10^9$ | | 10 | $0.18 \times 10^9$ | 5 | $0.20 \times 10^9$ | | Mixing of 80 ml UCB PL with 5 ml |
| | S.2.2 | | $0.29 \times 10^9$ | | $0.28 \times 10^9$ | | | $0.14 \times 10^9$ | | $0.12 \times 10^9$ | | |
| | S.2.3 | | $0.26 \times 10^9$ | | $0.26 \times 10^9$ | | | $0.16 \times 10^9$ | | $0.13 \times 10^9$ | | |

TABLE 4-continued

Results of Platelet count derived from UCB and maternal Blood through (MB) Sedimentation process

| | | UCB derived Platelet | | | | | Maternal Blood derived Platelet | | | | | |
|---|---|---|---|---|---|---|---|---|---|---|---|---|
| | | Before Sedimentation | | After Sedimentation | | | Before Sedimentation | | After Sedimentation | | | Total |
| Sample Number | Triplets | Initial Volume (ml) | Initial Count (Platelets/ml) | Final Volume (ml) | Final Count (Platelets/ml) | Recovery (%) | Initial Volume (ml) | Initial Count (Platelets/ml) | Final Volume (ml) | Final Count (Platelets/ml) | Recovery (%) | platelets received (UCB + MB) |
| Average STDEV | | | $0.27 \times 10^9$ ±0.01 | | $0.26 \times 10^9$ ±0.02 | 96% | | $0.16 \times 10^9$ ±0.02 | | $0.15 \times 10^9$ ±0.04 | 94% | of MB PL Ratio is 16:1 $0.25 \times 10^9$ |
| Sample 3 | S.3.1 S.3.2 S.3.3 | 138.6 | $0.36 \times 10^9$ $0.33 \times 10^9$ $0.30 \times 10^9$ | 80 | $0.34 \times 10^9$ $0.29 \times 10^9$ $0.33 \times 10^9$ | | 6 | $0.24 \times 10^9$ $0.26 \times 10^9$ $0.22 \times 10^9$ | 3 | $0.26 \times 10^9$ $0.22 \times 10^9$ $0.24 \times 10^9$ | | Mixing of 80 ml UCB PL with 3 ml of MB PL Ratio is ~27:1 |
| Average STDEV | | | $0.33 \times 10^9$ ±0.03 | | $0.32 \times 10^9$ ±0.02 | 97% | | $0.24 \times 10^9$ ±0.02 | | $0.24 \times 10^9$ ±0.02 | 100% | $0.32 \times 10^9$ |
| Sample 4 | S.4.1 S.4.2 S.4.3 | 138 | $0.25 \times 10^9$ $0.28 \times 10^9$ $0.25 \times 10^9$ | 82 | $0.23 \times 10^9$ $0.28 \times 10^9$ $0.27 \times 10^9$ | | 10 | $0.08 \times 10^9$ $0.10 \times 10^9$ $0.09 \times 10^9$ | 5 | $0.10 \times 10^9$ $0.07 \times 10^9$ $0.10 \times 10^9$ | | Mixing of 82 ml UCB PL with 5 ml MB PL Ratio is ~16:1 |
| Average STDEV | | | $0.26 \times 10^9$ ±0.01 | | $0.26 \times 10^9$ ±0.02 | 100% | | $0.09 \times 10^9$ ±0.01 | | $0.09 \times 10^9$ ±0.01 | 94% | $0.24 \times 10^9$ |
| Sample 5 | S.5.1 S.5.2 S.5.3 | 88 | $0.18 \times 10^9$ $0.22 \times 10^9$ $0.2 \times 10^9$ | 60 | $0.19 \times 10^9$ $0.22 \times 10^9$ $0.18 \times 10^9$ | | 8 | $0.22 \times 10^9$ $0.14 \times 10^9$ $0.15 \times 10^9$ | 4 | $0.15 \times 10^9$ $0.18 \times 10^9$ $0.15 \times 10^9$ | | Mixing of 80 ml UCB PL with 5 ml of MB PL Ratio is 15:1 |
| Average STDEV | | | $0.20 \times 10^9$ ±0.02 | | $0.20 \times 10^9$ ±0.02 | 100% | | $0.17 \times 10^9$ ±0.04 | | $0.16 \times 10^9$ ±0.01 | 97% | $0.20 \times 10^9$ |

The average platelet counts and platelet recovery before and after sedimentation was calculated and presented in Table 4. From Table 4, one can infer that the average recovery of platelets from UCB and maternal blood by sedimentation method ranges from 94%-100%. It can be appreciated from the Table 4 that most platelets were recovered during the sedimentation process without major loss. Also, the average recovery of the platelets from UCB of the samples 1-5 is 99% and the average recovery of the platelets from MB is 97%.

The platelet counts obtained from UCB through the centrifugation process was measured for comparison with the sedimentation process.

Table 5 shows the UCB derived platelet counts and MB derived platelet counts before and after centrifugation. A total of 5 sample data have been represented in triplicates. Quantification having average and standard deviation were calculated of Platelet counts of UCB.

TABLE 5

Results of Platelet count derived from UCB and MB through Centrifugation process

| | | UCB derived Platelet | | | | MB derived Platelet | | | | |
|---|---|---|---|---|---|---|---|---|---|---|
| | | Before Centrifugation | | After Centrifugation | | Before Centrifugation | | After Centrifugation | | Mixed |
| Sample Number | Triplets | Initial Volume (ml) | Initial Count (Platelets/ml) | Final Volume (ml) | Final Count (Platelets/ml) | Initial Volume (ml) | Initial Count (Platelets/ml) | Final Volume (ml) | Final Count (Platelets/ml) | platelet of UCB + MB |
| Sample 1 | S.1.1 S.1.2 S.1.3 | 96.43 | $0.16 \times 10^9$ $0.18 \times 10^9$ $0.17 \times 10^9$ | 45 | $0.08 \times 10^9$ $0.09 \times 10^9$ $0.08 \times 10^9$ | 10 | $0.16 \times 10^9$ $0.18 \times 10^9$ $0.15 \times 10^9$ | 5 | $0.11 \times 10^9$ $0.12 \times 10^9$ $0.09 \times 10^9$ | Mixing of 45 ml UCB PL |

TABLE 5-continued

Results of Platelet count derived from UCB and MB through Centrifugation process

| Sample Number | Triplets | UCB derived Platelet | | | | MB derived Platelet | | | | Mixed platelet of UCB + MB |
|---|---|---|---|---|---|---|---|---|---|---|
| | | Before Centrifugation | | After Centrifugation | | Before Centrifugation | | After Centrifugation | | |
| | | Initial Volume (ml) | Initial Count (Platelets/ml) | Final Volume (ml) | Final Count (Platelets/ml) | Initial Volume (ml) | Initial Count (Platelets/ml) | Final Volume (ml) | Final Count (Platelets/ml) | |
| Average STDEV | | | $0.17 \times 10^9$ ±0.01 | | $0.08 \times 10^9$ ±0.005 Recovery-47% | | $0.16 \times 10^9$ ±0.015 | | $0.10 \times 10^9$ ±0.015 | $0.08 \times 10^9$ with 5 ml of MB PL Ratio is 9:1 |
| Sample 2 | S.2.1 S.2.2 S.2.3 | 91.54 | $0.19 \times 10^9$ $0.19 \times 10^9$ $0.20 \times 10^9$ | 35 | $0.11 \times 10^9$ $0.11 \times 10^9$ $0.11 \times 10^9$ | 9 | $0.15 \times 10^9$ $0.14 \times 10^9$ $0.16 \times 10^9$ | 4.5 | $0.11 \times 10^9$ $0.08 \times 10^9$ $0.11 \times 10^9$ | Mixing of 35 ml UCB PL with 4.5 ml of MB PL Ratio is ~8:1 |
| Average STDEV | | | $0.19 \times 10^9$ ±0.005 | | $0.11 \times 10^9$ 0 Recovery-58% | | $0.15 \times 10^9$ ±0.01 | | $0.10 \times 10^9$ ±0.017 | $0.11 \times 10^9$ |
| Sample 3 | S.3.1 S.3.2 S.3.3 | 90.08 | $0.24 \times 10^9$ $0.23 \times 10^9$ $0.23 \times 10^9$ | 38 | $0.16 \times 10^9$ $0.16 \times 10^9$ $0.16 \times 10^9$ | 12 | $0.18 \times 10^9$ $0.15 \times 10^9$ $0.16 \times 10^9$ | 6 | $0.12 \times 10^9$ $0.09 \times 10^9$ $0.11 \times 10^9$ | Mixing of 38 ml UCB PL with 6 ml of MB PL Ratio is ~6:1 |
| Average STDEV | | | $0.23 \times 10^9$ 0 | | $0.16 \times 10^9$ 0 Recovery-70% | | $0.16 \times 10^9$ ±0.015 | | $0.10 \times 10^9$ ±0.015 | $0.15 \times 10^9$ |
| Sample 4 | S.4.1 S.4.2 S.4.3 | 109.72 | $0.25 \times 10^9$ $0.24 \times 10^9$ $0.24 \times 10^9$ | 42 | $0.15 \times 10^9$ $0.15 \times 10^9$ $0.15 \times 10^9$ | 8 | $0.11 \times 10^9$ $0.13 \times 10^9$ $0.12 \times 10^9$ | 4 | $0.08 \times 10^9$ $0.09 \times 10^9$ $0.11 \times 10^9$ | Mixing of 35 ml UCB PL with 4.5 ml of MB PL Ratio is ~10.5:1 |
| Average STDEV | | | $0.24 \times 10^9$ ±0.005 | | $0.15 \times 10^9$ 0 Recovery-63% | | $0.12 \times 10^9$ ±0.01 | | $0.09 \times 10^9$ ±0.015 | $0.14 \times 10^9$ |
| Sample 5 | S.5.1 S.5.2 S.5.3 | 99.56 | $0.21 \times 10^9$ $0.21 \times 10^9$ $0.21 \times 10^9$ | 40 | $0.14 \times 10^9$ $0.15 \times 10^9$ $0.15 \times 10^9$ | 10 | $0.15 \times 10^9$ $0.17 \times 10^9$ $0.18 \times 10^9$ | 5 | $0.11 \times 10^9$ | Mixing of 35 ml UCB PL with 4.5 ml of MB PL Ratio is 8:1 |
| Average STDEV | | | $0.21 \times 10^9$ 0 | | $0.14 \times 10^9$ ±0.005 Recovery-67% | | $0.16 \times 10^9$ ±0.015 | | $0.12 \times 10^9$ ±0.01 | $0.14 \times 10^9$ |

Average platelet counts and platelet recovery before and after centrifugation of umbilical cord blood (UCB) samples were calculated and have been shown in Table 5. From Table 5, one can infer that the average recovery of platelets from UCB by centrifugation method ranges from 47%-70%. Similarly, the recovery of MB derived platelets is also on a lower range. This states that most platelets were not recovered during the standard centrifugation process.

Table 6 provides a comparison of sedimentation versus centrifugation method of (UCB+MB) derived platelets and UCB derived platelets respectively.

TABLE 6

Comparison of platelets of UCB and MB through method of sedimentation and centrifugation method

|  | SEDIMENTATION | CENTRIFUGATION |
|---|---|---|
| STEPS | Multiple sedimentation (thrice) | spin@180gX10MINS* |
| REAGENTS NEEDED | Ficoll-Hypaque (a mixture of Ficoll (polysucrose) and Hypaque (sodium diatrizoate)), Hespan ® which is 6% hetastarch in 0.9% sodium chloride solution), and Pentastarch (artificial colloid (hydroxyethyl starch derivative)-Sedimentation reagent | NIL |
| Avg PLATELET YIELD | ~0.24 × 10$^9$ platelets/ml of UCB+MB sample | 0.13 × 10$^9$ platelets/ml for 1 sample |
| Avg RECOVERY | 94-100 (%) | 47-70 (%) |
| FREEZE THAW | 1-3 times | 1-3 times |
| TESTING | HIV I & II, HBsAg, Anti HCV, Syphilis, MYCOPLASMA, STERILITY | HIV I & II, HBsAg, Anti HCV, Syphilis, MYCOPLASMA, STERILITY |

*Julia Etulain et al., 2018; scientific reports

It can be appreciated that the present process as disclosed herein provides significantly higher recovery than centrifugation method.

Figure 3:
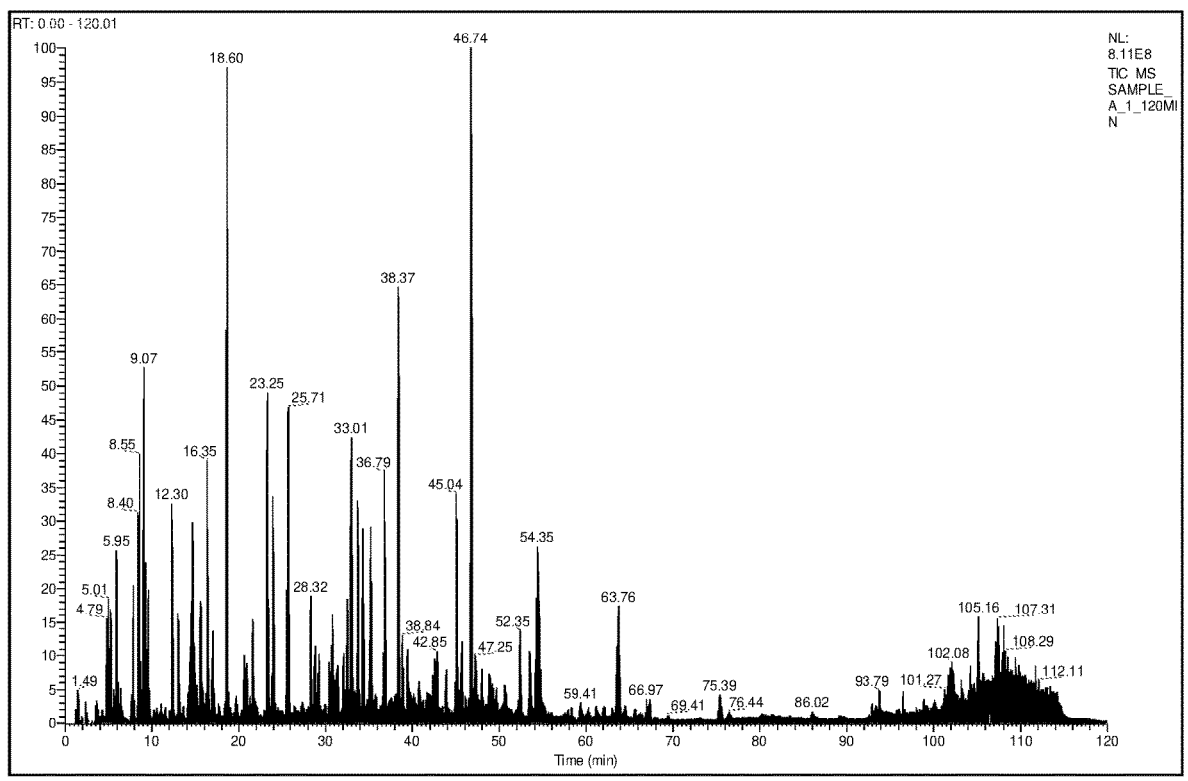
FIG. 3 illustrates a Chromatogram for UCB+MB PL, in accordance with an embodiment of the present disclosure.
Figure 4:
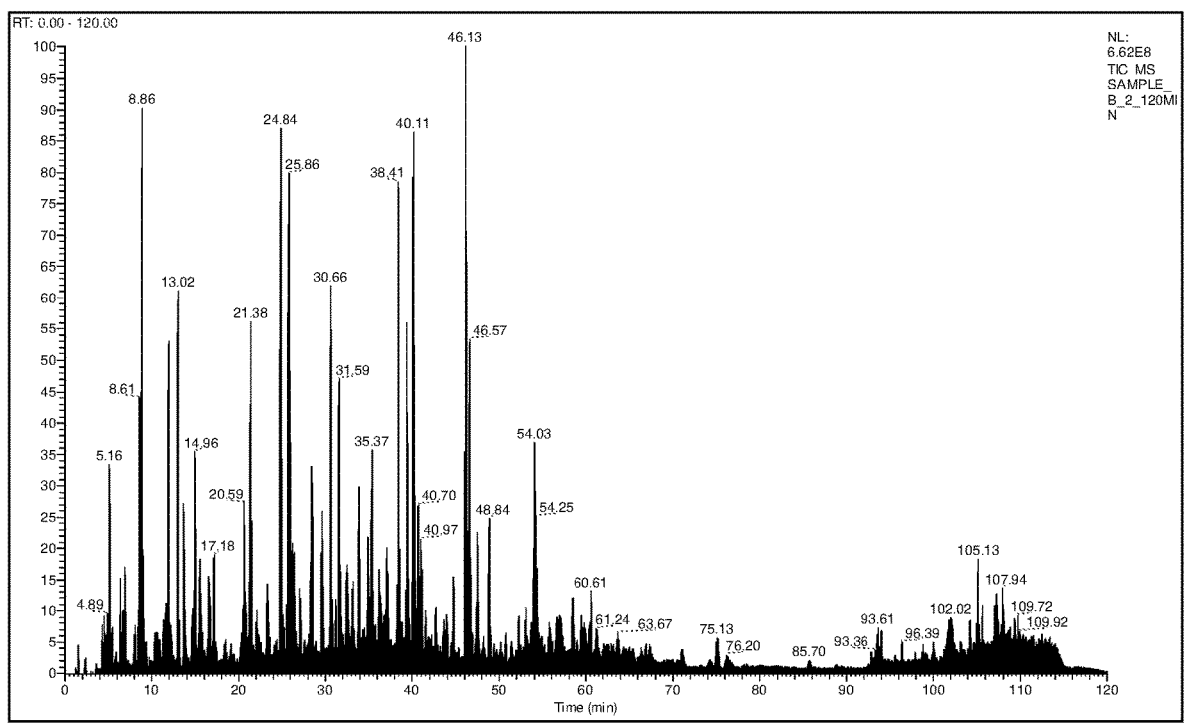
FIG. 4 illustrates a Chromatogram for FBS, in accordance with an embodiment of the present disclosure.
Figure 5:
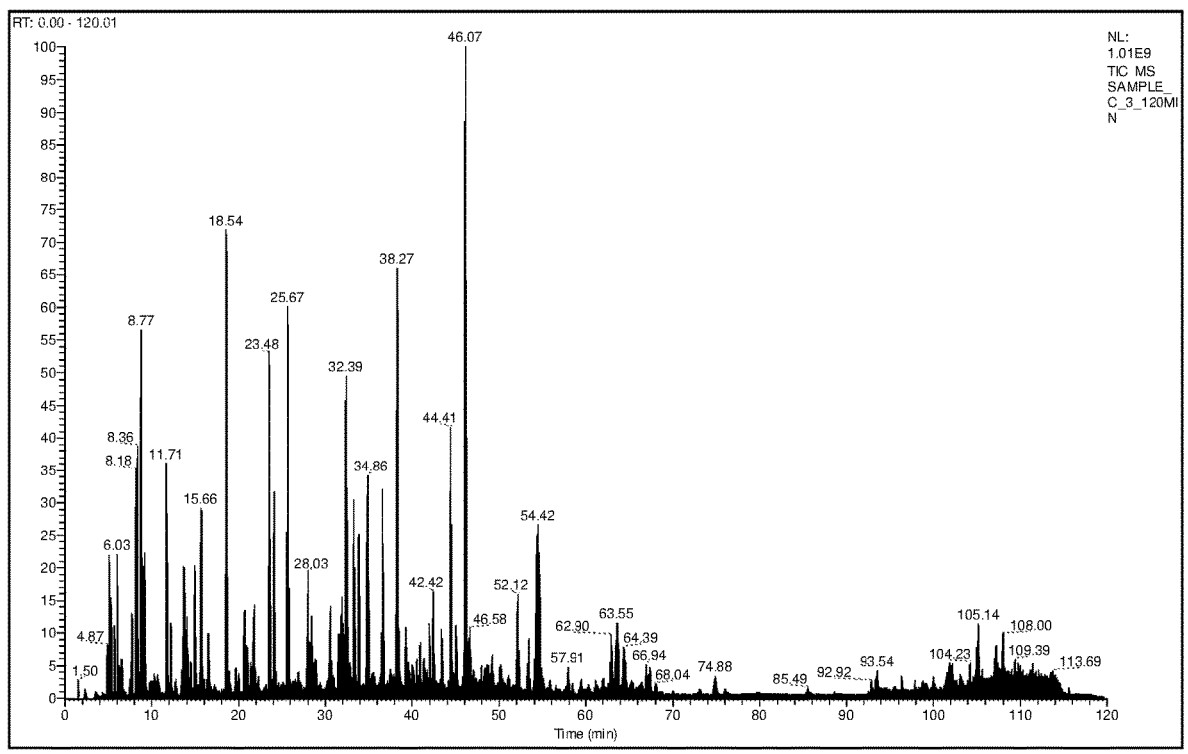
FIG. 5 illustrates a Chromatogram for UCB PL, in accordance with an embodiment of the present disclosure.
Figure 6:
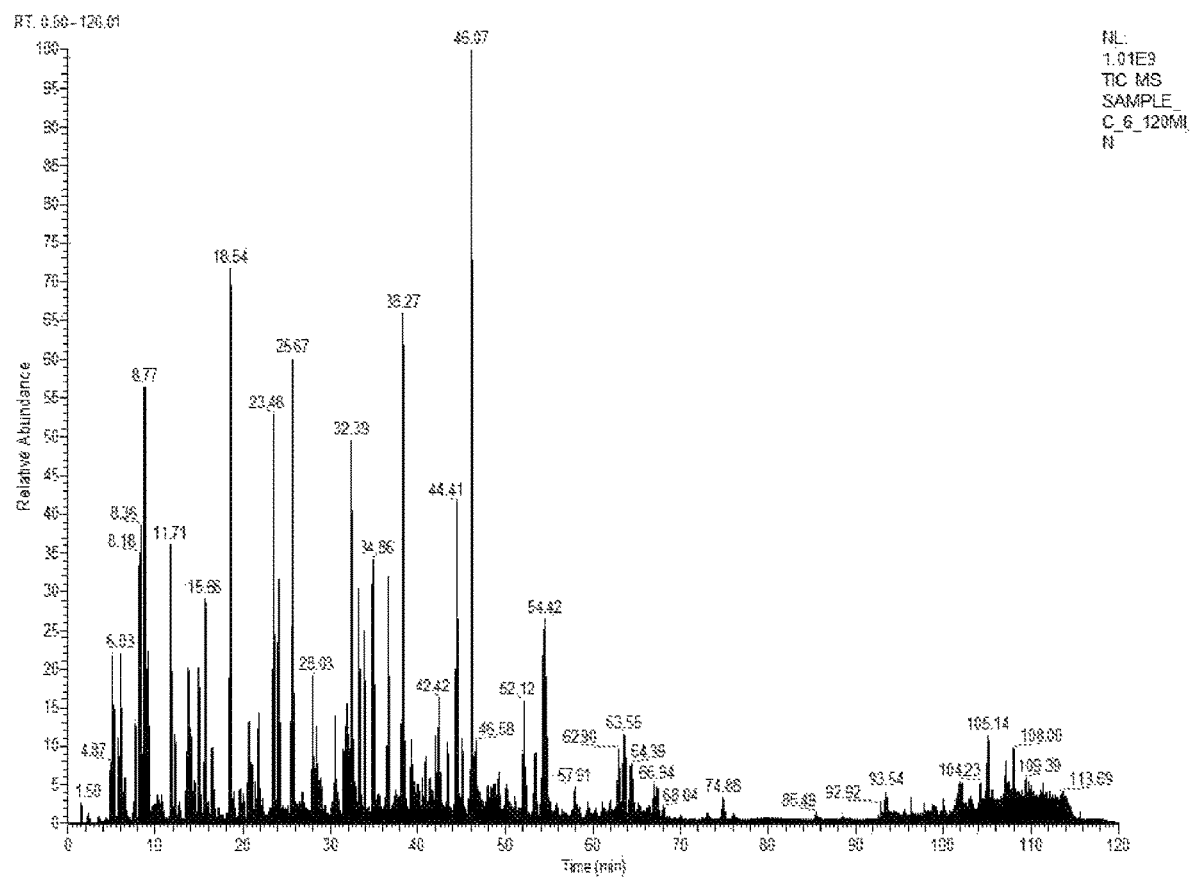
FIG. 6 illustrates a Chromatogram for 1-year data for the profile of UCB+MB PL, in accordance with an embodiment of the present disclosure.

Further the collected platelets of UCB and MB through the process of sedimentation was further enriched by the process of centrifugation for 10 minutes to provide higher and concentrated yield of platelet which could have potential use for therapeutic purpose. The FIGS. 3, 4, and 5 depicts the chromatogram of UCB+MB PL (obtained as per the sedimentation method), FBS, and UCB PL (obtained as per the sedimentation method).

Table 7 provides the data of the enrichment of the UCB and MB derived platelets.

As can be observed the average platelet count reached up to 1.46×10$^9$/ml.

| Sample | Initial volume of UCB + MB Platelet | Initial Platelet count (×10$^9$/ml) | Final PRP volume | platelet count (×10$^9$/ml) | Loss of platelet (%) | Platelet recovery (%) |
|---|---|---|---|---|---|---|
| Sample 1 | 10 ml | 0.166 | 1.0 ml | 1.48 | 10.84 | 89.16 |
| Sample 2 |  | 0.152 |  | 1.38 | 09.21 | 90.79 |
| Sample 3 |  | 0.173 |  | 1.52 | 12.14 | 87.86 |
| AVG |  | 0.164 |  | 1.46 | 10.73 | 89.27 |

Example 7

ID Testing: HIV I and II, HBsAg, Anti HBc, Anti HCV, CMV IgM, CMV IgG Anti HTLV I and II and Syphilis ID Testing for HIV:

HIV I/II ELISA was employed herein, which involved an immunosorbent enzyme assay which consists of recombinant protein for gp120, gp41 of HIV-I and gp36 of HIV-II bound to wells of microplate. During the course of assay, diluted controls and diluted specimens were added to the wells and incubated. HIV specific antibody (Ab), if present, binds to the antigens. After a thorough washing of the wells to remove unbound Ab and other serum components, standardized preparation of horse radish peroxidase—conjugate was added to each well. The conjugate preparation was then allowed to react with antibodies which bind to the assay wells on the basis of the specificity for antigenic determinants present within HIV antigens. After second thorough washing of the wells to remove unbound horseradish peroxidase-conjugated Ab, a substrate solution containing hydrogen peroxide and TMB was added to each well. A blue colour developed in proportion to the amount of HIV specific antibodies present, if any, in serum or plasma samples tested. This enzyme-substrate reaction was terminated by addition of sulfuric acid. The colour changes to yellow that have occurred in each well were then measured spectrophotometrically at a wavelength of 450 nm/630 nm. The sample was considered negative when OD value of the sample is less than the value of positive control.

ID Testing for HCV:

An indirect antibody EIA assay for HCV ELISA was performed for detection of antibodies to HCV in human serum and plasma. It employed an immunosorbent enzyme assay which consists of recombinant protein for core and Ns3 protein and synthetic peptides corresponding to highly antigenic segments, Ns4 and Ns5 regions of the hepatitis C virus bound to wells of a microplate. During the course of the assay, diluted controls and diluted specimens were added to the wells and incubated. HCV specific Ab, if present, binds to the antigens. After a thorough washing of the wells to remove unbound Ab and other serum components, standardized preparation of horse radish peroxidase-conjugate was added to each well. The conjugate preparation was then allowed to react with antibodies which bind to the assay wells on the basis of the specificity for antigenic determinants present within HCV antigens. After second thorough washing of the wells to remove unbound horseradish peroxidase-conjugated Ab, a substrate solution containing hydrogen peroxide and TMB was added to each well. A blue colour develops in proportion to the amount of HCV specific antibodies present, if any, in serum or plasma samples tested. This enzyme-substrate reaction was terminated by addition of sulfuric acid. The colour changes to yellow was measured in each well spectrophotometrically at a wavelength of 450 nm/630 nm. The sample was considered negative when OD value of the sample was less than the value of positive control.

ID Testing for HBsAg:

A solid phase ELISA for HBsAg detection based on sandwich capture principle was performed. During the course of the assay, diluted controls and diluted specimens were added to the wells and incubated. HBs specific Ab, if present, binds to the antigens. When patient serum containing HBsAg was added, it combined with the goat anti-HBsAg attached to polystyrene surface of the microwells and simultaneously bound with the horse radish peroxidase conjugated monoclonal anti-HBsAg. Wells were washed and a colorless enzyme substrate ($H_2O_2$) and chromogen (TMB, tetramethylbenzidine) were added. The enzyme acts on substrate/chromogen and produced a blue colored end product. This enzyme-substrate reaction was terminated by addition of sulfuric acid. The color changes to yellow that have occurred in each well are then measured spectrophotometrically at a wavelength of 450 nm/630 nm. The yellow color intensity was directly related to concentration of Hepatitis B surface antigen in the patient sample. The sample was considered negative when OD value of the sample was less than the value of positive control.

ID Testing for HBc:

An indirect antibody EIA assay for HBc ELISA was performed for the simultaneous detection of antibodies of total antibodies to hepatitis B virus core in human serum or plasma. It was based upon the use of a solid phase prepared with recombinant HBc antigen. The sera to be tested and the control sera were added to the wells. If antibodies to HBc were present, they will bind to the antigen fixed on solid phase. The peroxidase-labeled antibodies to human IgG and IgM are added after a washing step. They in turn bind to the specific antibodies captures on solid phase. After removal of unbound enzymatic conjugate, the antigen-antibody complex is revealed by addition of substrate. This enzyme-substrate reaction is terminated by addition of sulfuric acid. The colour changes to yellow that have occurred in each well are then measured spectrophotometrically at a wavelength of 450 nm/630 nm. The absorbance measured for a sample allows the presence and absence of antibodies to HBc to be determined. The colour intensity is proportional to the quantity of anti HBc antibodies bound to the solid phase. The sample is considered negative when OD value of the sample is less than the value of positive control.

ID Testing for CMV IgG:

Microplates were coated with the native Cytomegalovirus antigens, highly purified by sucrose gradient centrifugation and inactivated. The solid phase was first treated with the diluted sample and IgG to Cytomegalovirus are captured, if present, by the antigens. The peroxidase-labeled conjugated polyclonal antibodies to human IgG are added after a washing step. They in turn bind to the specific antibodies captures on solid phase. The enzyme captured on solid phase, acting on substrate and chromogen mixture, generate an optical signal that is proportional to the amount of anti-Cytomegalovirus IgG antibodies present in sample at 450/630 nm. The sample was considered negative when OD value of the sample is less than the value of positive control.

ID Testing for CMV IgM:

The assay is based on the principle of IgM capture where IgM class antibodies in sample are first captured by solid phase coated with hIgM antibody. A complex composed of biotinylated CMV antigen and Streptavidin, labeled with peroxidase were added after a washing step. They in turn bind to the specific antibodies captures on solid phase. The enzyme captured on solid phase, acting on substrate and chromogen mixture, generate an optical signal that is proportional to the amount of anti-Cytomegalovirus IgM antibodies present in sample at 450/630 nm.

The sample is considered negative when OD value of the sample is less than the value of positive control.

ID Testing for HTLV I & II Ab:

Microplates were coated with the HTLV I & II specific synthetic immunodominant antigens, derived from gp46-I, gp46II and gp21-I. The solid phase was first treated with the sample and Anti HTLV I & II are captured, if present, by the antigens coated to the microplate. The peroxidase-labeled specific synthetic antigens derived from gp46-I, gp46-II and gp21 were added after a washing step. They in turn bind to the specific antibodies captures on solid phase. The enzyme captured on solid phase, acting on substrate and chromogen mixture, generate an optical signal that is proportional to the amount of anti HTLV I & II antibodies present in sample at 450/630 nm. The sample was considered negative when OD value of the sample is less than the value of positive control. All the samples for the 0 month, 6 month, and 1 year showed absence of infectious diseases.

Example 8

Albumin Levels in (UCB+MB) PL, UCB PL and FBS

A primary function of albumin is to bind and stabilize a range of small molecules and ions. In in vitro, albumin acts as a multifaceted antioxidant. Its total antioxidant activity is a composite of many individual antioxidant activities. Albumin binds fatty acids and protects them from oxidation; binds copper and keeps it from participating in oxidation reactions. Albumin leads to a consideration of the extracellular and intracellular actions of the molecule, and importantly the role of its interactions with numerous ligands or bioactive factors that influence the growth of cells in culture: these include hormones, growth factors, lipids, amino acids, metal ions, reactive oxygen and nitrogen species. The interaction of albumin with the cell in relation to these co-factors has a potential impact on metabolic and biosynthetic activity, cell proliferation and survival.

Method:

Albumin was estimated quantitatively by colorimetric based method. Albumin standards were prepared at different concentrations such as 0, 0.5, 1.0, 1.5, 2.0, 2.5, 3.0, 3.5, 4.0, 4.5, 5.0 g/dL. The samples were diluted by 2 folds for testing. 5 μl each of diluted standards and diluted samples were transferred into wells of a clear bottom plate. 200 μl of Bromocresol green (BCG) reagent were added and incubated for 5 min at room temperature. The reagent, Bromocresol green forms a colored complex with albumin when tested positive. The intensity of the color was measured at 620 nm which is directly proportional to the albumin concentration in the sample.

TABLE 8

Albumin Assay

| Sr. No | Details | Manufacturing Time(Zero) | | | Six Month | | | One Year | | |
| --- | --- | --- | --- | --- | --- | --- | --- | --- | --- | --- |
| | | Sedimentation method (UCB + MB) PL | Sedimentation UCB PL | FBS | Sedimentation method (UCB + MB) PL | Sedimentation UCB PL | FBS | Sedimentation method (UCB + MB) PL | Sedimentation UCB PL | FBS |
| B. | Albumin Assay Level | 2.4 g/dL | 2.1 g/dL | 2.17 g/dL | 2.3 g/dL | 1.95 g/dL | 2.15 g/dL | 2.25 g/dL | 1.9 g/dL | 2.15 g/dL |

Albumin was estimated by colorimetric method at initial stage, after six months and after a year. Table 8 infers that the level of albumin is higher in the UCB+MB PL when compared to standard UCB PL and FBS.

Example 9

Presence of Protein Using SDS-PAGE in (UCB+MB) PL, UCB PL and FBS

The plates were assembled for casting gel as per manufacturer's instructions.

Add 60 µl of APS (ammonium persulfate), 2.4 µl of TEMED solution and 2.4 ml of 30% Acrylamide to 3.6 ml of SDS separating gel mix and pour the gel solution between then plates till the level is 2 cm below the top edge of notched plate. Add 200 to 250 µl of water to make the surface even. After the gel are set (approximately 30-40 min), wash the top of the separating gel with distilled water and drain off the water completely. Add 40 µl of APS, 4 µl of TEMED solution and 0.67 ml of 30% Acrylamide to 3.4 ml of stacking gel mix and pour directly onto the polymerized separating gel. Insert the comb into the gel solution carefully without trapping any bubbles, about 1 cm above the separating gel. The stacking gel will set in approximately 20 min.

Take 2, 3, 4, 5 µl of provided Protein sample in 4 microfuge vials. Label them as 1, 2, 3, 4 respectively. Add 20 µl of sample loading buffer to protein samples. Place the samples in water bath for 5 min. After the stacking gel has set, carefully remove the comb and the bottom spacer. Wash the wells immediately with distil led water to remove non-polymerized acrylamide. Assemble the gel set in the Gel running apparatus as per manufacturer's instruction. Fill the top and bottom reservoir with 1× Gel running buffer. Load 20 µl protein markers in the first well and then load prepared Protein samples in well 2, 3, 4, 5. Note down the order of loading. Connect the cords to the power supply according to the convention. Set voltage at 100 V and switch on the power supply. When the dye front comes to 0.5 cm above the bottom of the gel, turn off the power. This will take approximately 1 to 1:30 hours. Remove the gel plates and gently open the plates apart using a spatula or similar tool, don't try to separate the plates at the notch as it might damage the notch.

Transfer the gel to a tray containing water; wash the gel for 1-2 minutes at room temperature. Decant water, cut the gel along lane 4. Transfer lanes 1-5, i.e. protein sample in 10 ml of blotting buffer taken in a Petri dish. Keep at room temperature for 10 minutes. Following incubation, proceed for electroblotting. To the gel piece add minimum of 20 ml water. Wash the gel by rotating gently. Decant the water; add 20 ml of Ezee Blue Stain. Stain at room temperature for 1-2 hours. For uniform staining and washing, place the tray on a rocker intermittently every 10 to 15 minutes. Decant the staining solution add minimum quantity of water to cover the gel. Cover the tray and leave it overnight at room temperature.

Figure 2:
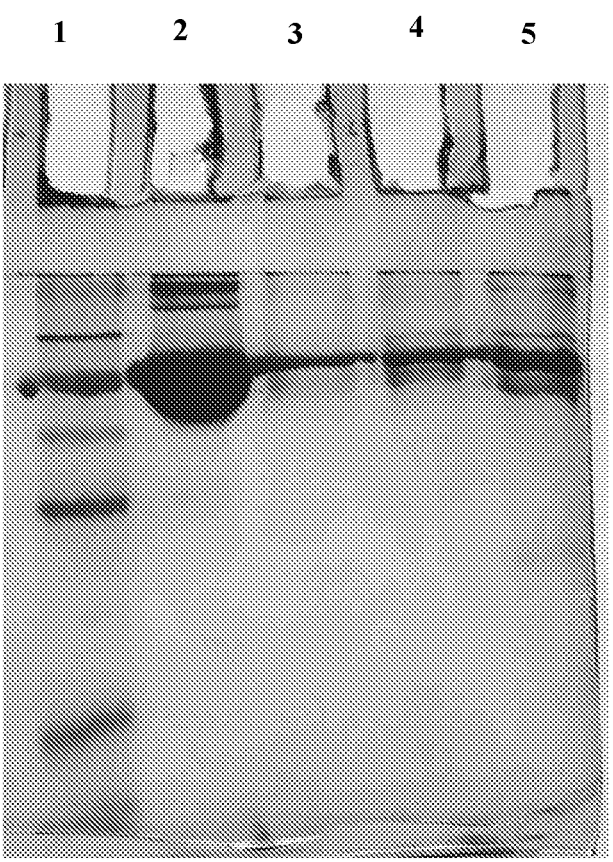
FIG. 2 illustrates SDS-PAGE results from aliquots of platelet lysates from UCB+MB, UCB, and FBS, in accordance with an embodiment of the present disclosure. Different lanes represented are: Lane 1—Marker, Lane 2—Standard Human Albumin Protein, Lane 3—FBS Protein, Lane 4—UCB PL Protein, and Lane 5—(UCB+MB) PL Protein.

FIG. 2 shows the SDS PAGE gel picture having markers and tested samples in different lanes.

In lane one, there is a ladder with marker ranging from 10 kDa to 220 kDa. These are used to determine the size of proteins in the gel. Each band in the ladder is a known molecular weight. The samples can be determined from these known weights.

In lane two there is standard Human Albumin protein of 49 kDa. Further lane 3, 4 and 5 shows the results of tested sample.

From the gel, it is determined that standard Human Albumin protein and FBS Protein, UCB PL Protein and UCB+MB PL Protein are relatively pure proteins.

It was found that a standard Human Albumin protein will have the same molecular weight regardless of the concentration of the tested sample as the albumin levels tested were in the range of 1.9-2.5 g/dL (Table 8). Further, FIG. 2 and Table 8 shows that UCB+MB PL sample has more of the albumin protein compared to FBS and UCB PL.

Example 10

Identification of Proteins Using LCMS in (UCB+MB) PL, UCB PL and FBS
Tryptic Digestion of Proteins Proteins were estimated by UV spectrophotometer using Bradford protein quantification protocol. 50 µg proteins were denatured and digested by Proteomic Grade trypsin (Sigma T6567). In brief, 50 µg of protein was dissolved in 50 mM ammonium bicarbonate buffer containing 0.1% RapiGest (Waters Corporation, MA, USA). Proteins were reduced and alkylated by treating with 100 mM dithiothreitol for 15 min at 60° C. and 200 mM iodoacetamide for 30 min at room temperature respectively. Denatured proteins were treated with trypsin (1:25) at 37° C. for 18 h and the reaction was stopped by addition of 0.1% formic acid. Digested peptides were desalted by using C18 Zip tips (Millipore, Billerica, MA) and the eluted peptides were concentrated by using vacuum concentrator. The peptides were reconstituted in 3% ACN with 0.1% formic Acid and used for mass spectrometric analysis.

LC Separation

Peptide digests (2.5 µg) were separated by using Accela 1250 UHPLC (Thermo Fisher Scientific) equipped with a Hypersil Gold C18-reverse phase column (150*2.1 mm, 1.9 µm). The sample was loaded onto the column with 98% of mobile phase A (100% water, 0.1% formic acid (FA)) and 2% of mobile phase B (100% ACN, 0.1% FA) at 350 µl/min flow rate. Peptides were eluted with a 45 min linear gradient of 2 to 40% mobile phase B. In case of plasma samples, the LC method was extended to 120 min with a linear gradient of 2 to 50% of mobile phase B. The column temperature was set to 40° C. and auto sampler at 8° C. All samples were analyzed on hybrid quadruple Q-Exactive Orbitrap MS. The instrument tune parameters were optimized for the better results as: spray voltage 4,200 V, capillary temperature 320° C., heater temperature 200° C., S-lens RF value 55, sheath and auxiliary gases pressure were 30 and 8 psi, respectively. The samples were acquired in positive ionization mode in data-dependent manner using a top-five method with scan range from 350-1,800 m/z. MS spectra were acquired at a resolution of 70,000 with maximum injection time (IT) of 120 ms and automatic gaincontrol (AGC) value of 1 e6 ions; MS/MS spectra were acquired at 17,500 resolution with maximum IT of 120 ms and AGC value of 1e5 ions. Precursor's selectivity was performed at an isolation width of 3 m/z, under fill ratio of 0.3%, and dynamic exclusion time of 15 s. The peptide fragmentation was performed in high energy collision induced dissociation (HCD) cell using normalized HCD at 30 eV.

Protein Identification:

Proteins were searched against UniProt reviewed human protein database by using Proteome Discoverer software with following parameters, 1% FDR. The precursor and fragment initial mass error tolerance was set to 0.05 and 0.1 Da, respectively. Search parameters also included carbamidomethylation of cysteine residues as fixed modifications and methionine oxidation as variable modification.

TABLE 9

Protein identification using LC-MS

| Sample ID | No. of Total Proteins identified by LC-MS | No. of common proteins with respect to sample 1 | Resemblance with sample 1 (%) |
|---|---|---|---|
| Sample 1 (UCB Platelets + maternal PL) | 206 | 206 | 100% |
| Sample 2 (Fetal Bovine serum) | 93 | 31 | 15.04% |
| Sample 3 (Umbilical Cord blood PL) | 171 | 108 | 52.42% |

Umbilical Cord blood platelets with maternal blood platelets (Sample 1) showed a total of 206 proteins whereas Umbilical Cord platelets (Sample 3) showed only a total of 171 proteins and commercially available serum supplement such as FBS (Sample 2) shows a total of 93 proteins (Table 9).

Thus, it can be observed that the mixture of UCB and MB platelets resulted in an addition of 35 proteins compared to the Standard Umbilical Cord blood platelets and an addition of 113 proteins compared to commercial FBS.

Conclusively, it can be stated that the optimized combination of UCB and MB results in higher protein identification and confirmation when compared to commercial or standard serum supplements.

Masses are graphed according to their relative abundance against time (See FIG. 3 (Graph 1: Sample-01 (UCB+MB PL) Chromatogram), 4 (Graph 2: Sample-02 (FBS) Chromatogram), 5 (Graph 3: Sample-02 (UCB PL) Chromatogram)), 6 (Graph 4: Sample-02 (MB PL) Chromatogram)). The relative abundance corresponds to the different identified proteins as mentioned in Table 10.

TABLE 10

| Sample ID | No. of Total Proteins identified by LC-MS | No. of common proteins with respect to sample 1 | Resemblance with sample 1 (%) |
|---|---|---|---|
| Sample 1 (UCB Platelets + maternal PL) | 206 | 206 | 100% |
| Sample 2 (Fetal Bovine serum) | 93 | 31 | 15.04% |
| Sample 3 (Umbilical Cord blood PL) | 171 | 108 | 52.42% |

Thus, the mixture of UCB+MB platelet lysates gives the highest amount and number of proteins.

The list of identified proteins in the optimized (UCB+MB) PL of significant value for cell culture are as follows:

Vimentin [VIME_HUMAN] (SEQ ID NO: 1) which is an intermediate filament (IF) protein that is the predominant IF in cells of mesenchymal origin such as vascular endothelium and blood cells. It facilitates cell migration and motility by recycling internalized trailing edge integrins back to the cell surface at the leading edge.

Vascular endothelial growth factor receptor 1 [VGFR1_HUMAN] (SEQ ID NO: 2) which mediates signals for differentiation. Expression of this receptor is found in vascular endothelial cells, placental trophoblast cells and peripheral blood monocytes. This protein binds to VEGFR-A, VEGFR-B and placental growth factor and plays an important role in angiogenesis and vasculogenesis. Expression of this receptor is found in vascular endothelial cells, placental trophoblast cells and peripheral blood monocytes.

Glyceraldehyde-3-phosphate dehydrogenase [E7EUT5_HUMAN] (SEQ ID NO: 3) which is an enzyme of ~37 kDa that catalyzes the sixth step of glycolysis and thus serves to break down glucose for energy and carbon molecules. GAPDH has been implicated in several non-metabolic processes, including transcription activation, initiation of apoptosis, ER to Golgi vesicle shuttling, and fast axonal, or axoplasmic transport. In sperm, a testis-Specific isoenzyme GAPDHS is expressed. GAPDH act as an oxidoreductase, acting on the aldehyde or oxo group of donors, NAD or NADP as acceptor.

Pyruvate kinase PKM [KPYM_HUMAN] (SEQ ID NO: 4) which encodes a protein involved in glycolysis. The encoded protein is a pyruvate kinase that catalyzes the transfer of a phosphoryl group from phosphoenolpyruvate to ADP, generating ATP and pyruvate. This protein has been shown to interact with thyroid hormone and may mediate cellular metabolic effects induced by thyroid hormones.

Mesoderm posterior protein 1 [MESP1_HUMAN] (SEQ ID NO: 5) which plays a role in the epithelialization of somatic mesoderm and in the development of cardiac mesoderm.

Isoform 3 of N-alpha-acetyltransferase 60 [NAA60_HUMAN] (SEQ ID NO: 6) which is a protein that was located on the Golgi apparatus and mainly catalyze the N-acetylation of transmembrane proteins. Acetylation is one of the most ubiquitous modifications that plays a vital role in many biological processes, such as transcriptional regulation1, protein-protein interaction, enzyme activity, protein stability, antibiotic resistance, biological rhythm.

Isoform 3 of Serine/threonine-protein kinase Chk1 [CHK1_HUMAN] (SEQ ID NO: 7) is encoded by this gene belongs to the Ser/Thr protein kinase family; checkpoint mediated cell cycle arrest in response to DNA damage or the presence of unreplicated DNA. DNA damage induces activation of Chk1, which then transduces the checkpoint signal and facilitates cell cycle arrest and DNA damage repair.

Fructose-bisphosphate aldolase A [ALDOA_HUMAN] (SEQ ID NO: 8) encodes a protein which is a glycolytic enzyme that catalyzes the reversible aldol cleavage of fructose-1,6-biphosphate and fructose 1-phosphate to dihydroxyacetone phosphate and either glyceraldehyde-3-phosphate or glyceraldehyde, respectively.

Isoform 4 of Triosephosphate isomerase [TPI-S_HUMAN] (SEQ ID NO: 9) enhances triose-phosphate isomerase activity and ubiquitin protein ligase binding.

Trinucleotide repeat-containing gene 6C protein [TNR6C_HUMAN] (SEQ ID NO: 10) is a gene that plays a role in RNA-mediated gene silencing by micro-RNAs (miRNAs). Required for miRNA-dependent translational repression of complementary mRNAs by argonaute family proteins.

Histone H4 [H4_HUMAN] (SEQ ID NO: 11) display a peak in transcription in early S phase and are ideal models for cell cycle-regulated gene expression.

Centromere protein F [CENPF_HUMAN] (SEQ ID NO: 12) is required for kinetochore function and chromosome segregation in mitosis. Regulates recycling of the plasma membrane by acting as a link between recycling vesicles and the microtubule network.

Neutrophil defensin 1 [DEF1_HUMAN] (SEQ ID NO: 13) is a part of defensins, which are a family of antimicrobial and cytotoxic peptides thought to be involved in host defense. The protein encoded by this gene, defensin, alpha 1, is found in the microbicidal granules of neutrophils and likely plays a role in phagocyte-mediated host defense.

Isoform 2 of Heat shock cognate 71 kDa protein [HSP7C_HUMAN] (SEQ ID NO: 14) binds to nascent polypeptides to facilitate correct protein folding. Its role in protein folding contributes to its function in signal transduction, apoptosis, protein homeostasis, and cell growth and differentiation.

Mannose-binding protein C [MBL2_HUMAN] (SEQ ID NO: 15) is a pattern recognition molecule of the innate immune system. This provides the host with a first-line of defense before the adaptive immune system becomes operative.

Protein S100-A8 [S10A8_HUMAN] (SEQ ID NO: 16) encodes a vitamin K-dependent plasma protein that functions as a cofactor for the anticoagulant protease, activated protein C (APC) to inhibit blood coagulation. It is found in plasma in both a free, functionally active form and also in an inactive form complexed with C4b-binding protein. Mutations in this gene result in autosomal dominant hereditary thrombophilia. An inactive pseudogene of this locus is located at an adjacent region on chromosome 3. Alternative splicing results in multiple transcript variants encoding different isoforms that may undergo similar processing to generate mature protein.

Serpin A12 [SPA12_HUMAN] (SEQ ID NO: 17) belongs to a family of serpins, which are a broadly distributed family of protease inhibitors that use a conformational change to inhibit target enzymes. They are central in controlling many important proteolytic cascades, including the mammalian coagulation pathways.

Synaptotagmin-13 [SYT13_HUMAN] (SEQ ID NO: 18) based on their brain/endocrine distribution and biochemical properties, in particular C2 domains of certain synaptotagmins bound to calcium. synaptotagmins were proposed to function as calcium sensors in the regulation of neurotransmitter release and hormone secretion.

Isoform 2 of Tubulin alpha-1B chain [TBA1B_HUMAN] (SEQ ID NO: 19) is part of microtubules, which are built from a basic α/β-tubulin building block, yet subpopulations of microtubules can be differentially marked by a number of post-translational modifications. Tubulin modifications play an important role in regulating microtubule properties, such as stability and structure, as well as microtubule-based functions, such as ciliary beating, cell division, and intracellular trafficking.)

Profilin-1 [PROF1_HUMAN] (SEQ ID NO: 20) encodes a member of the profilin family of small actin-binding proteins. The encoded protein plays an important role in actin dynamics by regulating actin polymerization in response to extracellular signals.

Adenylyl cyclase-associated protein [B4DNW7_HUMAN] (SEQ ID NO: 21) is a Receptor for Human Resistin and Mediates Inflammatory Actions of Human Monocytes.

C-myc promoter-binding protein 1 [E2DRY6_HUMAN] (SEQ ID NO: 22) encodes a DENN domain-containing protein that may function as a guanine nucleotide exchange factor that specifically activates Ras-related protein Rab-10. This protein also contains an interferon stimulated response element-binding domain and may be involved in regulating the v-myc avian myelocytomatosis viral (MYC) oncogene.)

Mitochondrial heat shock 60 kD protein 1 variant 1 [B3GQS7_HUMAN] (SEQ ID NO: 23) are generally responsible for preventing damage to proteins in response to high levels of heat. It may facilitate the correct folding of imported proteins and may also prevent misfolding and promote the refolding and proper assembly of unfolded polypeptides generated under stress conditions in the mitochondrial matrix.

Protein S100 [B2R4M6_HUMAN] (SEQ ID NO: 24) are a family of low-molecular-weight proteins characterized by two calcium-binding sites that have helix-loop-helix ("EF-hand type") conformation. They are also considered as Damage-associated molecular pattern molecules (DAMPs) and knockdown of AHR down regulates the expression of S100 proteins in THP-1 cell.

Beta tropomyosin isoform [A7XZE4_HUMAN] (SEQ ID NO: 25) reduction associated with transformation, regulates anoikis. Associated with establishing focal adhesions. Restores stress fibers in transformed cells.

Peroxiredoxin-1 [A0A0A0MRQ5_HUMAN] (SEQ ID NO: 26) encodes a protein that may play an antioxidant protective role in cells and may contribute to the antiviral activity of CD8(+) T-cells. This protein may have a proliferative effect and play a role in cancer development or progression.

Example 11

Final Product Sterility, Mycoplasma and Endotoxin Testing

Sterility:

The sample to be tested is inoculated into the vial which is entered into the BACTEC (BD BACTE FX 400 blood culture system) instrument for incubation and periodic reading. Each vial contains a sensor which responds to the concentration of CO2 produced by the metabolism of microorganisms or the consumption of oxygen needed for the growth of microorganisms. The sensor is monitored by the instrument every ten minutes for an increase in its fluorescence, which is proportional to the increasing amount of CO2 or the decreasing amount of O2 present in the vial. A positive reading indicates the presumptive presence of viable microorganisms in the vial.

Mycoplasma:

Mycoplasma contamination is detected using PCR technique. In this method, DNA extraction of given sample is carried out and PCR is performed on the samples, using primers specific for mycoplasma DNA along with dNTPs and another DNA synthesis enzyme. Running the PCR product on a gel shows the presence/absence of mycoplasma DNA by band(s) of distinct sizes.

Endotoxin:

Bacterial endotoxin level is determined using Endosafe PTs reader method. The test is a rapid, point-of-use handheld spectrophotometer that uses disposable cartridge for accurate convenient and realtime endotoxin testing, glucan identification and gram identification. All the tests showed no microbial growth and the endotoxin values showed <0.750 EU/ml in all the samples.

Product safety was performed by testing sterility, mycoplasma and endotoxin at manufacturing time, after six month and after a year to examine whether the product is free from any contaminations.

Example 12

Hematopoietic Stem Cells (HSC) Colony Forming Unit (CFU) Assay

Umbilical Cord blood leukocyte cell concentrate containing Hematopoietic Stem cells (HSC) that were seeded for HSC-CFU assay in one 35 mm cell culture Petri plates, were used. Leukocyte cell concentrate sample containing HSC (1.3 ml having $2 \times 10^4$ cells) were seeded in 35 mm petri plate cultured with 1.5 ml of Methocult, IMDM, growth factors and 5% FBS/5% UCB-PL/UCB-MB PL. These cultured plates were placed in 90/100 mm culture dish with one more 35 mm culture dish (without lid) containing sterile DW. These Petri plates were incubated in $CO_2$ incubator with 5% $CO_2$ at 37° C. under humidified conditions for 14 days of incubation.

Counting Colonies:

After 14 days of incubation, 35 mm culture plates were taken out from $CO_2$ incubator and observed under inverted microscope. After opening the lid of plates, plates were kept in 60 mm gridded scoring dish under the stage of an inverted microscope. Colonies were enumerated of each plate using manual blood cell counter. After counting the colonies photographs of the same were taken under 100× magnification. Both the colonies CFU-GM (Colony Forming Unit-Granulocyte Macrophage) and BFU-E (Burst Forming Unit-Erythrocyte) colonies were counted and number of colonies were recorded.

Results: HSC CFU Assay: Below table demonstrates the results of HSC CFU colonies—CFU-GM (Colony Forming Unit-Granulocyte Macrophage) and BFU-E (Burst Forming Unit-Erythrocyte) colonies observed under inverted microscope at 14 days of culture.

TABLE 11

UCB Stem cells (HSC) CFU assay with number of CFU-GM, BFU-E colonies

| Sr. No | Sample ID | Result | | No. CFU-GM colonies obtained | No. BFU-E colonies obtained | Remark |
|---|---|---|---|---|---|---|
| 1 | Sample 01 | Positive Growth of colonies | PL | 11 | 7 | CFU-GM (Colony Forming Unit-Granulocyte Macrophage) and BFU-E (Burst Forming Unit-Erythrocyte) colonies observed |
|  |  |  | FBS | 12 | 9 |  |
|  |  |  | UCB + MB PL | 13 | 11 |  |
| 2 | Sample 02 | Positive Growth of colonies | PL | 10 | 8 | CFU-GM (Colony Forming Unit-Granulocyte Macrophage) and BFU-E (Burst Forming Unit-Erythrocyte) colonies observed |
|  |  |  | FBS | 13 | 10 |  |
|  |  |  | UCB + MB PL | 14 | 11 |  |
| 3 | Sample 03 | Positive Growth of colonies | PL | 12 | 8 | CFU-GM (Colony Forming Unit-Granulocyte Macrophage) and BFU-E (Burst Forming Unit-Erythrocyte) colonies observed |
|  |  |  | FBS | 13 | 7 |  |
|  |  |  | UCB + MB PL | 15 | 9 |  |

TABLE 12

UCB leukocyte cell concentrate containing Hematopoietic Stem cells (HSC) CFU assay

| Sample | Culture supplement[#] | 0 days | | 1 year | |
|---|---|---|---|---|---|
|  |  | CFU | BFU | CFU | BFU |
| Sample 01 | PL | $2.74 \times 10^5$ | $1.99 \times 10^5$ | $2.16 \times 10^5$ | $1.51 \times 10^5$ |
|  | FBS | $3.03 \times 10^5$ | $2.53 \times 10^5$ | $2.45 \times 10^5$ | $2.03 \times 10^5$ |
|  | UCB + MB PL | $3.53 \times 10^5$ | $2.79 \times 10^5$ | $3.03 \times 10^5$ | $2.33 \times 10^5$ |
| Sample 02 | PL | $2.82 \times 10^8$ | $2 \times 10^8$ | $2.27 \times 10^8$ | $1.56 \times 10^8$ |
|  | FBS | $3.54 \times 10^8$ | $2.76 \times 10^8$ | $2.80 \times 10^5$ | $2.00 \times 10^5$ |
|  | UCB + MB PL | $3.93 \times 10^5$ | $3.10 \times 10^5$ | $3.09 \times 10^5$ | $2.69 \times 10^5$ |
| Sample 03 | PL | $2.65 \times 10^5$ | $2.18 \times 10^5$ | $2.02 \times 10^5$ | $1.99 \times 10^5$ |
|  | FBS | $3.35 \times 10^5$ | $2.51 \times 10^5$ | $3.09 \times 10^5$ | $2.37 \times 10^5$ |
|  | UCB + MB PL | $3.72 \times 10^5$ | $3.13 \times 10^5$ | $3.14 \times 10^5$ | $2.83 \times 10^5$ |

Figure 7:
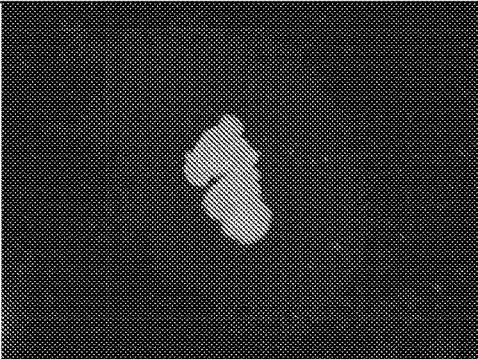
FIG. 7 illustrates UCB leukocyte cell concentrate containing Hematopoietic Stem cells (HSC) CFU assay images for CFU-G (Colony Forming Unit-Granulocyte) and BFU (Burst Forming Unit), in accordance with an embodiment of the present disclosure.

[#]Umbilical Cord blood leukocyte cell concentrate containing Hematopoietic Stem cells (HSC) cultured with 1.5 ml of Methocult, IMDM, growth factors and 5% FBS/5%UCB-PL/UCB-MB PL It can be observed from Table 11 and 12 that the UCB+MB PL provides better performance in terms of the CFU and BFU values for both UCB stem cells (HSC) and UCB leukocyte cell concentrate containing HSC. FIG. 7 depicts the images of UCB leukocyte cell concentrate containing HSC CFU assay images for CFU-G and BFU. The images of FIG. 7 correlate with the data provided in Table 12.

Example 13

Efficacy Studies Carried Out on 5 Different Cell Lines and Compared between in (UCB+MB) PL, UCB PL, MB PL, and FBS.

The Platelet lysate of all sources (UCB+MB) PL, UCB PL, MB PL, and FBS was added to culture medium at different concentrations of 5% and 20%. The best cell growth in terms of count, viability and characterization was found in UCBPL+MBPL group in the different cell lines was tested by performing various experiments such as cell purity, cell viability, cell count, cell characterization and cryopreservation which are enlisted as below:

Cell Purity:

Cell purity test is carried out using the ELISA technique wherein protein levels in the sample are detected and compared with standard human albumin. The values of the samples are recorded. Maximum allowed limit for this is 1 g/dL.

Cell Characterization (Flow Cytometry):

Cell surface antigen of specific cells can be determined by using flow cytometry. In this test cell surface antibodies of specific cells are incubated with cells followed by washing and centrifugation. Cells treated with antibodies are compared with untreated cells after acquisition of cells on flow cytometer. Based on the results, percent cell population positive for specific cell surface antigen is determined and recorded.

Cell Count and Cell Viability:

Cells were harvested and dissolved in 10 ml of growth medium. 20 µl of cell suspension were taken and mixed with 20 µl of trypan blue dye. Load 10 µl of cell suspension along with trypan blue dye on hemocytometer. Cells were counted in all four chambers and final cell count was calculated as per following formula.

Total cell count=B1+N2+N3+N4/4×2×104× dilution factor (Where N1, N2, N3, N4 are cell counts in four chambers)

The Trypan Blue dye exclusion test is used to determine the number of viable cells present in a cell suspension. It is based on the principle that live cells possess intact cell membranes that exclude the dye, whereas dead cells do not. A viable cell will have a clear cytoplasm whereas a nonviable cell will have a blue cytoplasm.

Ultra-Low Freezing:

Platelet lysate prepared using UCB+MB platelets were aliquoted in 50 ml sterile centrifuge tubes and stored at −86° C. At different intervals of 6 months and 1 year, PL aliquots were thawed at 37° C. temperature in water bath and used as a supplement for different cell culture and expansion purpose.

Cryopreservation:

Cells of different lineages were cryopreserved for a time period of six months and one year. The cryopreservation was done using cell freezing medium containing either 90% of optimized PL +10% DMSO or 90% of cord blood PL +10% DMSO and/or 90% of FBS +10% DMSO. Further these cryovials are subjected to process of controlled freezing using Control rate freezer and reduced temperature upto −50° C. with 1° C. per min freezing rate with the help of liquid nitrogen and after attaining temperature at −50° C., the cryovials are immediately transferred at a temperature below −150° C. in liquid nitrogen tank (under Vapour phase conditions).

Reprocess of Cryopreserved Samples:

Cryopreserved cells of different lineages were thawed and reprocessed at different time intervals such as 6 months and one year. In this process, cryopreserved vials were removed from Liquid nitrogen tank and immediately thawed the vials containing cells in water bath at 37° C. After thawing, the cell suspension from cryovial were transferred to growth medium (DMEM, F12 with FGF) containing 10% of optimized platelet lysate or 10% of cord blood PL or 10% FBS and centrifuged at 1200-1800 rpm for 5-10 mins. Supernatant were discarded and further suspend the cell pellet in culture medium (DMEM, F12 with FGF) containing 10% of optimized platelet lysate or 10% of cord blood PL or 10% FBS and cell count and cell viability tests were performed, and their observations were recorded in the tables below.

Mycoplasma Test:

Mycoplasma test were performed and found negative for all cell lineages.

Cell Line 1: Chondrocytes Culture with (UCB+MB) PL Vs UCB PL Vs FBS

Table 13: samples of chondrocytes were cultured with (UCB+MB) PL, UCB PL and FBS. Cell count, cell viability was performed followed by cell characterization using Flowcytometry. It was observed that the results of cell count, cell viability and cell characterization were higher in (UCB+MB)PL when compared to UCB PL and FBS.

TABLE 13

|   |   | CELL COUNT (million) | CELL VIABILITY (%) | CELL PURITY (g/dL) marker | ENDO-TOXIN (EU/ml) | Cell characterization CD44 & CD151cell surface expression (%) | KARYO-TYPING |
|---|---|---|---|---|---|---|---|
| SAMPLE 1 | 0 Month PL(UCB + MB) PL | $4.5 \times 10^6$ | 97.58 | 0.5 g/dL | <0.750 EU/ml | 99.3 | No chromosomal abnormalities |
|   | 0 Month PLUCB PL | $4.1 \times 10^6$ | 96.54 | 0.6 g/dL | <0.750 EU/ml | 99.1 | No chromosomal abnormalities |
|   | 0 Month FBS | $4.0 \times 10^6$ | 95.23 | 0.68 g/dL | <0.750 EU/ml | 99.6 | No chromosomal abnormalities |

TABLE 13-continued

|  |  | CELL COUNT (million) | CELL VIABILITY (%) | CELL PURITY (g/dL) marker | ENDO-TOXIN (EU/ml) | Cell characterization CD44 & CD151cell surface expression (%) | KARYO-TYPING |
| --- | --- | --- | --- | --- | --- | --- | --- |
|  | 6 Month PL(UCB + MB) PL | $4.1 \times 10^6$ | 97.45 | 0.52 g/dL | <0.750 EU/ml | 98.57 | No chromosomal abnormalities |
|  | 6 Month PLUCB PL | $3.9 \times 10^6$ | 96.66 | 0.62 g/dL | <0.750 EU/ml | 97.41 | No chromosomal abnormalities |
|  | 6 Month FBS | $3.8 \times 10^6$ | 96.02 | 0.69 g/dL | <0.750 EU/ml | 96.52 | No chromosomal abnormalities |
|  | 1 yr. (UCB + MB) PL | $4.0 \times 10^6$ | 96.79 | 0.56 g/dL | <0.750 EU/ml | 98.10 | No chromosomal abnormalities |
|  | 1 yr. UCB PL | $3.64 \times 10^6$ | 94.2 | 0.69 g/dL | <0.750 EU/ml | 94.24 | No chromosomal abnormalities |
|  | 1 yr FBS | $3.4 \times 10^6$ | 93.28 | 0.72 g/dL | <0.750 EU/ml | 93.51 | No chromosomal abnormalities |
| SAMPLE 2 | 0 Month PL(UCB + MB) PL | $4.6 \times 10^6$ | 98.66 | 0.59 g/dL | <0.750 EU/ml | 99.5 | No chromosomal abnormalities |
|  | 0 Month PLUCB PL | $4.2 \times 10^6$ | 97.54 | 0.68 g/dL | <0.750 EU/ml | 98.54 | No chromosomal abnormalities |
|  | 0 Month FBS | $4.1 \times 10^6$ | 93.58 | 0.72 g/dL | <0.750 EU/ml | 99.4 | No chromosomal abnormalities |
|  | 6 Month PL(UCB + MB) PL | $4.32 \times 10^6$ | 97.54 | 0.57 g/dL | <0.750 EU/ml | 98.83 | No chromosomal abnormalities |
|  | 6 Month PLUCB PL | $3.92 \times 10^6$ | 96.57 | 0.69 g/dL | <0.750 EU/ml | 97.76 | No chromosomal abnormalities |
|  | 6 Month FBS | $4.0 \times 10^6$ | 97.56 | 0.75 g/dL | <0.750 EU/ml | 97.14 | No chromosomal abnormalities |
|  | 1 yr. (UCB + MB) PL | $4.2 \times 10^6$ | 96.89 | 0.56 g/dL | <0.750 EU/ml | 98.04 | No chromosomal abnormalities |
|  | 1 yr. UCB PL | $3.74 \times 10^6$ | 95.52 | 0.71 g/dL | <0.750 EU/ml | 96.33 | No chromosomal abnormalities |
|  | 1 yr FBS | $3.66 \times 10^6$ | 94.22 | 0.79 g/dL | <0.750 EU/ml | 96.15 | No chromosomal abnormalities |
| SAMPLE 3 | 0 Month PL(UCB + MB) PL | $4.8 \times 10^6$ | 95.78 | 0.65 g/dL | <0.750 EU/ml | 99.4 | No chromosomal abnormalities |
|  | 0 Month PLUCB PL | $3.95 \times 10^6$ | 95.15 | 0.66 g/dL | <0.750 EU/ml | 98.9 | No chromosomal abnormalities |
|  | 0 Month FBS | $3.85 \times 10^6$ | 95.11 | 0.78 g/dL | <0.750 EU/ml | 99 | No chromosomal abnormalities |
|  | 6 Month PL(UCB + MB) PL | $4.26 \times 10^6$ | 95.68 | 0.67 g/dL | <0.750 EU/ml | 98.7 | No chromosomal abnormalities |
|  | 6 Month PLUCB PL | $3.89 \times 10^6$ | 94.54 | 0.69 g/dL | <0.750 EU/ml | 98.1 | No chromosomal abnormalities |
|  | 6 Month FBS | $3.76 \times 10^6$ | 94.28 | 0.79 g/dL | <0.750 EU/ml | 97.78 | No chromosomal abnormalities |
|  | 1 yr. (UCB + MB) PL | $4.18 \times 10^6$ | 94.28 | 0.65 g/dL | <0.750 EU/ml | 98.4 | No chromosomal abnormalities |

TABLE 13-continued

|  |  | CELL COUNT (million) | CELL VIABILITY (%) | CELL PURITY (g/dL) marker | ENDO-TOXIN (EU/ml) | Cell characterization CD44 & CD151cell surface expression (%) | KARYO-TYPING |
|---|---|---|---|---|---|---|---|
|  | 1 yr. UCB PL | $3.77 \times 10^6$ | 92.17 | 0.69 g/dL | <0.750 EU/ml | 96.57 | No chromosomal abnormalities |
|  | 1 yr FBS | $3.54 \times 10^6$ | 93.38 | 0.81 g/dL | <0.750 EU/ml | 96.47 | No chromosomal abnormalities |
| SAMPLE 4 | 0 Month PL(UCB + MB) PL | $4.2 \times 10^6$ | 97.48 | 0.59 g/dL | <0.750 EU/ml | 99.0 | No chromosomal abnormalities |
|  | 0 Month PLUCB PL | $4.12 \times 10^6$ | 96.59 | 0.68 g/dL | <0.750 EU/ml | 98.54 | No chromosomal abnormalities |
|  | 0 Month FBS | $4.10 \times 10^6$ | 96.68 | 0.76 g/dL | <0.750 EU/ml | 99.6 | No chromosomal abnormalities |
|  | 6 Month PL(UCB + MB) PL | $4.13 \times 10^6$ | 97.14 | 0..6 g/dL | <0.750 EU/ml | 98.57 | No chromosomal abnormalities |
|  | 6 Month PLUCB PL | $4.02 \times 10^6$ | 95.48 | 0.69 g/dL | <0.750 EU/ml | 97.77 | No chromosomal abnormalities |
|  | 6 Month FBS | $3.87 \times 10^6$ | 93.28 | 0.77 g/dL | <0.750 EU/ml | 97.87 | No chromosomal abnormalities |
|  | 1 yr. (UCB + MB) PL | $4.08 \times 10^6$ | 97.64 | 0.62 g/dL | <0.750 EU/ml | 97.86 | No chromosomal abnormalities |
|  | 1 yr. UCB PL | $3.8 \times 10^6$ | 92.28 | 0.72 g/dL | <0.750 EU/ml | 95.48 | No chromosomal abnormalities |
|  | 1 yr FBS | $3.7 \times 10^6$ | 93.05 | 0.79 g/dL | <0.750 EU/ml | 96.21 | No chromosomal abnormalities |
| SAMPLE 5 | 0 Month PL(UCB + MB) PL | $4.8 \times 10^6$ | 95.78 | 0.64 g/dL | <0.750 EU/ml | 94.89 | No chromosomal abnormalities |
|  | 0 Month PLUCB PL | $3.95 \times 10^6$ | 95.15 | 0.64 g/dL | <0.750 EU/ml | 95.76 | No chromosomal abnormalities |
|  | 0 Month FBS | $3.85 \times 10^6$ | 95.11 | 0.77 g/dL | <0.750 EU/ml | 92.57 | No chromosomal abnormalities |
|  | 6 Month PL(UCB + MB) PL | $4.26 \times 10^6$ | 95.68 | 0.65 g/dL | <0.750 EU/ml | 95.14 | No chromosomal abnormalities |
|  | 6 Month PLUCB PL | $3.89 \times 10^6$ | 94.54 | 0.68 g/dL | <0.750 EU/ml | 94.28 | No chromosomal abnormalities |
|  | 6 Month FBS | $3.76 \times 10^6$ | 94.28 | 0.79 g/dL | <0.750 EU/ml | 92.0 | No chromosomal abnormalities |
|  | 1 yr. (UCB + MB) PL | $4.2 \times 10^6$ | 95.54 | 0.65 g/dL | <0.750 EU/ml | 94.87 | No chromosomal abnormalities |
|  | 1 yr. UCB PL | $3.76 \times 10^6$ | 93.22 | 0.7 g/dL | <0.750 EU/ml | 93.69 | No chromosomal abnormalities |
|  | 1 yr FBS | $3.5 \times 10^6$ | 92.67 | 0.78 g/dL | <0.750 EU/ml | 91.87 | No chromosomal abnormalities |

It can be observed that the cell viability and the cell count of chondrocytes cultured using UCB+MB PL in case of all the five samples perform better as compared to the rest of the PL samples and also FBS sample, therefore, proving its higher efficacy.

Cell Line 2: Osteoblasts Culture with (UCB+MB) PL Vs UCB PL s FBS

Table 14: samples of osteoblasts cells were cultured with (UCB+MB) PL, UCB PL and FBS. Cell count, cell viability was performed followed by cell characterization using Flowcytometry (Table 14). It was observed that the results of cell count, cell viability and cell characterization were higher in (UCB+MB) PL when compared to UCB PL and FBS.

TABLE 14

| | | CELL COUNT (million) | CELL VIABILITY (%) | CELL PURITY (g/dL) | ENDO-TOXIN (EU/ml) | Cell characterization BALP cell surface marker expression (%) | KARYO-TYPING |
|---|---|---|---|---|---|---|---|
| SAMPLE 1 | 0 Month PL(UCB + MB) PL | $3.2 \times 10^6$ | 98.65 | 0..6 g/dL | <0.900 EU/ml | 87.4 | No chromosomal abnormalities |
| | 0 Month PLUCB PL | $3.1 \times 10^6$ | 97.58 | 0.69 g/dL | <0.900 EU/ml | 88.6 | No chromosomal abnormalities |
| | 0 Month FBS | $2.7 \times 10^6$ | 93.22 | 0.77 g/dL | <0.900 EU/ml | 85.2 | No chromosomal abnormalities |
| | 6 Month PL(UCB + MB) PL | $3.12 \times 10^6$ | 98.12 | 0.66 g/dL | <0.900 EU/ml | 88.1 | No chromosomal abnormalities |
| | 6 Month PLUCB PL | $3.0 \times 10^6$ | 97.01 | 0.7 g/dL | <0.900 EU/ml | 86.59 | No chromosomal abnormalities |
| | 6 Month FBS | $2.68 \times 10^6$ | 93.11 | 0.71 g/dL | <0.900 EU/ml | 85.14 | No chromosomal abnormalities |
| | 1 yr. (UCB + MB) PL | $3.1 \times 10^6$ | 97.85 | 0.65 g/dL | <0.900 EU/ml | 87.64 | No chromosomal abnormalities |
| | 1 yr. UCB PL | $2.82 \times 10^6$ | 96.26 | 0.71 g/dL | <0.900 EU/ml | 84.27 | No chromosomal abnormalities |
| | 1 yr FBS | $2.53 \times 10^6$ | 93.64 | 0.73 g/dL | <0.900 EU/ml | 83.69 | No chromosomal abnormalities |
| SAMPLE 2 | 0 Month PL(UCB + MB) PL | $3.1 \times 10^6$ | 97.72 | 0.64 g/dL | <0.900 EU/ml | 89.7 | No chromosomal abnormalities |
| | 0 Month PLUCB PL | $3.11 \times 10^6$ | 98.02 | 0.69 g/dL | <0.900 EU/ml | 87.58 | No chromosomal abnormalities |
| | 0 Month FBS | $2.9 \times 10^6$ | 96.31 | 0.79 g/dL | <0.900 EU/ml | 83.1 | No chromosomal abnormalities |
| | 6 Month PL(UCB + MB) PL | $3.0 \times 10^6$ | 97.08 | 0.62 g/dL | <0.900 EU/ml | 87.76 | No chromosomal abnormalities |
| | 6 Month PLUCB PL | $2.98 \times 10^6$ | 96.48 | 0.68 g/dL | <0.900 EU/ml | 86.28 | No chromosomal abnormalities |
| | 6 Month FBS | $2.87 \times 10^6$ | 95.55 | 0.79 g/dL | <0.900 EU/ml | 82.69 | No chromosomal abnormalities |
| | 1 yr. (UCB + MB) PL | $2.98 \times 10^6$ | 97.28 | 0.63 g/dL | <0.900 EU/ml | 87.11 | No chromosomal abnormalities |
| | 1 yr. UCB PL | $2.85 \times 10^6$ | 94.58 | 0.68 g/dL | <0.900 EU/ml | 95.23 | No chromosomal abnormalities |

TABLE 14-continued

|  |  | CELL COUNT (million) | CELL VIABILITY (%) | CELL PURITY (g/dL) | ENDO-TOXIN (EU/ml) | Cell characterization BALP cell surface marker expression (%) | KARYO-TYPING |
|---|---|---|---|---|---|---|---|
|  | 1 yr. FBS | $2.64 \times 10^6$ | 93.21 | 0.79 g/dL | <0.900 EU/ml | 82.16 | No chromosomal abnormalities |
| SAMPLE 3 | 0 Month PL(UCB + MB) PL | $3.0 \times 10^6$ | 96.31 | 0.7 g/dL | <0.900 EU/ml | 95.5 | No chromosomal abnormalities |
|  | 0 Month PLUCB PL | $2.95 \times 10^6$ | 95.86 | 0.69 g/dL | <0.900 EU/ml | 90.56 | No chromosomal abnormalities |
|  | 0 Month FBS | $2.94 \times 10^6$ | 92.27 | 0.82 g/dL | <0.900 EU/ml | 90 | No chromosomal abnormalities |
|  | 6 Month PL(UCB + MB) PL | $2.92 \times 10^6$ | 96.22 | 0.69 g/dL | <0.900 EU/ml | 94.59 | No chromosomal abnormalities |
|  | 6 Month PLUCB PL | $2.85 \times 10^6$ | 95.13 | 0.7 g/dL | <0.900 EU/ml | 90.24 | No chromosomal abnormalities |
|  | 6 Month FBS | $2.87 \times 10^6$ | 92.08 | 0.85 g/dL | <0.900 EU/ml | 89.69 | No chromosomal abnormalities |
|  | 1 yr. (UCB + MB) PL | $2.89 \times 10^6$ | 96.09 | 0.68 g/dL | <0.900 EU/ml | 93.97 | No chromosomal abnormalities |
|  | 1 yr. UCB PL | $2.71 \times 10^6$ | 94.06 | 0.73 g/dL | <0.900 EU/ml | 89.56 | No chromosomal abnormalities |
|  | 1 yr FBS | $2.56 \times 10^6$ | 91.56 | 0.84 g/dL | <0.900 EU/ml | 87.89 | No chromosomal abnormalities |
| SAMPLE 4 | 0 Month PL(UCB + MB) PL | $3.4 \times 10^6$ | 95.85 | 0.56 g/dL | <0.900 EU/ml | 94.7 | No chromosomal abnormalities |
|  | 0 Month PLUCB PL | $3.1 \times 10^6$ | 95.08 | 0.65 g/dL | <0.900 EU/ml | 91.69 | No chromosomal abnormalities |
|  | 0 Month FBS | $2.84 \times 10^6$ | 91.79 | 0.72 g/dL | <0.900 EU/ml | 91.3 | No chromosomal abnormalities |
|  | 6 Month PL(UCB + MB) PL | $3.28 \times 10^6$ | 94.89 | 0.59 g/dL | <0.900 EU/ml | 94.52 | No chromosomal abnormalities |
|  | 6 Month PLUCB PL | $3.0 \times 10^6$ | 93.56 | 0.67 g/dL | <0.900 EU/ml | 91.21 | No chromosomal abnormalities |
|  | 6 Month FBS | $2.8 \times 10^6$ | 91.05 | 0.8 g/dL | <0.900 EU/ml | 90.39 | No chromosomal abnormalities |
|  | 1 yr. (UCB + MB) PL | $3.22 \times 10^6$ | 95.58 | 0.63 g/dL | <0.900 EU/ml | 93.69 | No chromosomal abnormalities |
|  | 1 yr. UCB PL | $2.97 \times 10^6$ | 92.68 | 0.73 g/dL | <0.900 EU/ml | 90.45 | No chromosomal abnormalities |
|  | 1 yr FBS | $2.75 \times 10^6$ | 90.38 | 0.83 g/dL | <0.900 EU/ml | 89.73 | No chromosomal abnormalities |
| SAMPLE 5 | 0 Month PL(UCB + MB) PL | $3.3 \times 10^6$ | 95.85 | 0.52 g/dL | <0.900 EU/ml | 93.2 | No chromosomal abnormalities |
|  | 0 Month PLUCB PL | $3.2 \times 10^6$ | 93.57 | 0.68 g/dL | <0.900 EU/ml | 92.89 | No chromosomal abnormalities |
|  | 0 Month FBS | $2.75 \times 10^6$ | 91.79 | 0.74 g/dL | <0.900 EU/ml | 91.8 | No chromosomal abnormalities |
|  | 6 Month PL(UCB + MB) PL | $3.31 \times 10^6$ | 96.52 | 0.51 g/dL | <0.900 EU/ml | 93.5 | No chromosomal abnormalities |

TABLE 14-continued

|  | CELL COUNT (million) | CELL VIABILITY (%) | CELL PURITY (g/dL) | ENDO-TOXIN (EU/ml) | Cell characterization BALP cell surface marker expression (%) | KARYO-TYPING |
|---|---|---|---|---|---|---|
| 6 Month PLUCB PL | $2.98 \times 10^6$ | 92.79 | 0.624 g/dL | <0.900 EU/ml | 92.55 | No chromosomal abnormalities |
| 6 Month FBS | $2.80 \times 10^6$ | 90.86 | 0.75 g/dL | <0.900 EU/ml | 90.47 | No chromosomal abnormalities |
| 1 yr. (UCB + MB) PL | $3.29 \times 10^6$ | 96.22 | 0.53 g/dL | <0.900 EU/ml | 93.6 | No chromosomal abnormalities |
| 1 yr. UCB PL | $2.65 \times 10^6$ | 91.36 | 0.68 g/dL | <0.900 EU/ml | 90.52 | No chromosomal abnormalities |
| 1 yr FBS | $2.41 \times 10^6$ | 90.54 | 0.782 g/dL | <0.900 EU/ml | 89.67 | No chromosomal abnormalities |

It can be observed that the cell viability and the cell count of osteoblasts cultured using UCB+MB PL performs better as compared to the rest of the PL samples and also FBS sample, therefore, proving its higher efficacy.

The above tables (13 and 14) showed that the optimized combination of mixing umbilical cord blood derived platelet with maternal blood derived platelet envisages the same or adequate efficacy when compared to standard cord blood platelet or the commercial FBS as a serum supplement. The optimized formulation recorded and resulted the culturing, proliferation and expansion of plurality of cell lineages the like, mesenchymal stem cells derived from human umbilical cord tissue, osteoblasts differentiated from bone marrow derived mesenchymal stem cells, cardiomyocytes differentiated from human umbilical cord tissue derived mesenchymal stem cells, chondrocytes from human cartilage biopsy and buccal biopsy derived dermal fibroblasts.

This example determines the growth kinetics, self-renewing capacity, proliferation, differentiation, expansion, cell count, cell viability and cell characterization of the respective cell lineage, potential during extensive sub culturing and following cryopreservation. Primary cultures of each cell lines were established, an aliquot was cryopreserved and thawed and reprocessed, and then the populations were sub cultured parallelly for a time period of six months to one year. Cells derived from each lineage were assayed for their kinetics of growth and their potential in response to cell proliferation, differentiation and expansion in specific medium designed to respective area of therapeutics. The results confirmed that the resultant cell lineages, including but not limiting to, the osteogenic potential, chondrogenic potential, cardiomyocytes, dermal and/or epithelial potential was conserved throughout every passage. Furthermore, the process of cryopreserving and thawing the cells had no effect on either their growth or cellular differentiation and expansion when the said optimized combination of UCB and MB platelet lysate were incorporated.

Importantly, these studies demonstrate that replicative senescence of parent cell is not a state of terminal differentiation since these cells remain capable of progressing through their cell lineage. The use of optimized combination of mixing umbilical cord derived platelets and maternal blood derived platelets as a measure of biological age suggests that the said platelet lysate is intermediate between embryonic and adult tissues, and as such, may provide an in-situ source for progenitor cells throughout an adult's lifetime for various therapeutic purposes.

Example 14

Comparative Data for Two Cell Lines
Cell line 1: Chondrocytes Culture with (UCB+MB) PL vs UCB PL vs MB PL vs FBS Table 15 and Table 16 below showed that cell count, viability and characterization using differentiation markers are better and hence, showed greater efficacy of (UCB+MB) PL over UCB PL, MB PL and FBS. The comparison has also been done by using 5% each of (UCB+MB) PL, UCB PL, MB PL and FBS for culturing versus 20% each of (UCB+MB) PL, UCB PL, MB PL and FBS for culturing the chondrocytes (Table 15) and osteoblasts (Table 16). The data provided in Tables 14 and 15 are for the 0 month of culturing the cells.

TABLE 15

Chondrocytes culture with (UCB + MB) PL vs UCB PL vs MB PL vs FBS

|  |  | CELL COUNT (million) | CELL VIABILITY (%) | Cell characterization CD44 & CD151 cell surface marker expression (%) |
|---|---|---|---|---|
| SAMPLE 1 (5%) | PL (UCB + MB) | $3.2 \times 10^6$ | 91.58 | 88.3 |
|  | UCB PL | $2.7 \times 10^6$ | 85.70 | 85.5 |
|  | MB PL | $1.9 \times 10^6$ | 87.60 | 83.8 |
|  | FBS | $2.5 \times 10^6$ | 89.10 | 84.7 |

TABLE 15-continued

Chondrocytes culture with (UCB + MB) PL vs UCB PL vs MB PL vs FBS

|  |  | CELL COUNT (million) | CELL VIABILITY (%) | Cell characterization CD44 & CD151 cell surface marker expression (%) |
|---|---|---|---|---|
| SAMPLE 1 (20%) | PL (UCB + MB) | $4.5 \times 10^6$ | 97.58 | 99.3 |
|  | UCB PL | $4.1 \times 10^6$ | 96.54 | 99.1 |
|  | MB PL | $3.5 \times 10^6$ | 92.31 | 91.5 |
|  | FBS | $4.0 \times 10^6$ | 95.23 | 99.6 |
| SAMPLE 2 (5%) | PL (UCB + MB) | $2.8 \times 10^6$ | 92.3 | 89.2 |
|  | UCB PL | $2.2 \times 10^6$ | 87.1 | 86.1 |
|  | MB PL | $1.8 \times 10^6$ | 86.3 | 82.7 |
|  | FBS | $2.3 \times 10^6$ | 88.9 | 83.3 |
| SAMPLE 2 (20%) | PL (UCB + MB) | $4.6 \times 10^6$ | 98.66 | 99.5 |
|  | UCB PL | $4.2 \times 10^6$ | 97.54 | 98.54 |
|  | MB PL | $3.8 \times 10^6$ | 92.51 | 91.17 |
|  | FBS | $4.1 \times 10^6$ | 93.58 | 99.4 |
| SAMPLE 3 (5%) | PL (UCB + MB) | $2.9 \times 10^6$ | 91.3 | 89.8 |
|  | UCB PL | $2.6 \times 10^6$ | 87.8 | 85.9 |
|  | MB PL | $1.9 \times 10^6$ | 86.3 | 81.7 |
|  | FBS | $2.5 \times 10^6$ | 87.9 | 82.3 |
| SAMPLE 3 (20%) | PL (UCB + MB) | $4.8 \times 10^6$ | 95.78 | 99.4 |
|  | UCB PL | $3.95 \times 10^6$ | 95.15 | 98.9 |
|  | MB PL | $3.74 \times 10^6$ | 93.15 | 91.51 |
|  | FBS | $3.85 \times 10^6$ | 95.11 | 99 |
| 4SAMPLE 4 (5%) | PL (UCB + MB) | $2.8 \times 10^6$ | 92.3 | 88.8 |
|  | UCB PL | $2.3 \times 10^6$ | 88.5 | 84.9 |
|  | MB PL | $2.1 \times 10^6$ | 87.3 | 82.9 |
|  | FBS | $2.4 \times 10^6$ | 86.9 | 83.3 |
| SAMPLE 4 (20%) | PL (UCB + MB) | $4.2 \times 10^6$ | 97.48 | 99.0 |
|  | UCB PL | $4.12 \times 10^6$ | 96.59 | 98.54 |
|  | MB PL | $3.76 \times 10^6$ | 91.52 | 91.20 |
|  | FBS | $4.10 \times 10^6$ | 96.68 | 99.6 |
| SAMPLE 5 (5%) | PL (UCB + MB) | $3.2 \times 10^6$ | 90.3 | 89.8 |
|  | UCB PL | $2.8 \times 10^6$ | 87.7 | 85.4 |
|  | MB PL | $2.5 \times 10^6$ | 86.4 | 81.8 |
|  | FBS | $2.6 \times 10^6$ | 87.9 | 84.1 |
| SAMPLE 5 (20%) | PL (UCB + MB) | $4.8 \times 10^6$ | 95.78 | 94.89 |
|  | UCB PL | $3.95 \times 10^6$ | 95.15 | 95.76 |
|  | MB PL | $3.53 \times 10^6$ | 93.57 | 95.16 |
|  | FBS | $3.85 \times 10^6$ | 95.11 | 92.57 |

Cell line 2: Osteoblasts Culture with (UCB+MB) PL vs UCB PL vs MB PL vs FBS

Table 16 below showed that cell count, viability and characterization using differentiation markers are better and hence, showed greater efficacy of (UCB+MB) PL over UCB PL, MB PL and FBS.

TABLE 16

Osteoblasts culture with (UCB + MB) PL vs UCB PL vs MB PL vs FBS

|  |  | CELL COUNT (million) | CELL VIABILITY (%) | Cell characterization BALP cell surface marker expression (%) |
|---|---|---|---|---|
| SAMPLE 1 (5%) | PL (UCB + MB) | $2.1 \times 10^6$ | 97.45 | 87.98 |
|  | UCB PL | $1.7 \times 10^6$ | 96.78 | 87.22 |
|  | MB PL | $1.3 \times 10^6$ | 96.41 | 83.21 |
|  | FBS | $1.6 \times 10^6$ | 95.99 | 84.35 |
| SAMPLE 1 (20%) | PL (UCB + MB) | $3.2 \times 10^6$ | 98.65 | 87.40 |
|  | UCB PL | $3.1 \times 10^6$ | 97.58 | 88.60 |
|  | MB PL | $2.8 \times 10^6$ | 94.58 | 84.22 |
|  | FBS | $2.7 \times 10^6$ | 93.22 | 85.20 |
| SAMPLE 2 (5%) | PL (UCB + MB) | $2.0 \times 10^6$ | 97.33 | 88.34 |
|  | UCB PL | $1.8 \times 10^6$ | 97.10 | 87.52 |
|  | MB PL | $1.4 \times 10^6$ | 96.45 | 84.11 |
|  | FBS | $1.7 \times 10^6$ | 96.19 | 83.25 |
| SAMPLE 2 (20%) | PL (UCB + MB) | $3.1 \times 10^6$ | 97.72 | 89.70 |
|  | UCB PL | $3.11 \times 10^6$ | 98.02 | 87.58 |
|  | MB PL | $2.6 \times 10^6$ | 90.14 | 84.16 |
|  | FBS | $2.9 \times 10^6$ | 96.31 | 83.10 |
| SAMPLE 3 (5%) | PL (UCB + MB) | $2.2 \times 10^6$ | 96.33 | 93.34 |
|  | UCB PL | $1.9 \times 10^6$ | 95.75 | 89.42 |
|  | MB PL | $1.8 \times 10^6$ | 93.45 | 87.33 |
|  | FBS | $1.7 \times 10^6$ | 92.95 | 89.85 |
| SAMPLE 3 (20%) | PL (UCB + MB) | $3.0 \times 10^6$ | 96.31 | 95.50 |
|  | UCB PL | $2.95 \times 10^6$ | 95.86 | 90.56 |
|  | MB PL | $2.54 \times 10^6$ | 93.06 | 89.53 |
|  | FBS | $2.94 \times 10^6$ | 92.27 | 90.00 |
| SAMPLE 4 (5%) | PL (UCB + MB) | $2.1 \times 10^6$ | 96.23 | 93.24 |
|  | UCB PL | $1.8 \times 10^6$ | 95.65 | 89.12 |
|  | MB PL | $1.6 \times 10^6$ | 93.36 | 87.10 |
|  | FBS | $1.7 \times 10^6$ | 92.88 | 89.64 |

TABLE 16-continued

Osteoblasts culture with (UCB + MB) PL vs UCB PL vs MB PL vs FBS

| | | CELL COUNT (million) | CELL VIABILITY (%) | Cell characterization BALP cell surface marker expression (%) |
|---|---|---|---|---|
| SAMPLE 4 (20%) | PL (UCB + MB) | $3.4 \times 10^6$ | 95.85 | 94.70 |
| | UCB PL | $3.1 \times 10^6$ | 95.08 | 91.69 |
| | MB PL | $2.82 \times 10^6$ | 90.78 | 89.55 |
| | FBS | $2.84 \times 10^6$ | 91.79 | 91.30 |
| SAMPLES (5%) | PL (UCB + MB) | $1.9 \times 10^6$ | 96.10 | 93.11 |
| | UCB PL | $1.7 \times 10^6$ | 95.99 | 89.41 |
| | MB PL | $1.6 \times 10^6$ | 94.26 | 87.33 |
| | FBS | $1.5 \times 10^6$ | 92.98 | 89.54 |
| SAMPLE 5 (20%) | PL (UCB + MB) | $3.3 \times 10^6$ | 95.85 | 93.20 |
| | UCB PL | $3.2 \times 10^6$ | 93.57 | 92.89 |
| | MB PL | $2.77 \times 10^6$ | 90.29 | 91.52 |
| | FBS | $2.75 \times 10^6$ | 91.79 | 91.80 |

From Table 15 and 16, it can be observed that culturing of the cells is equally good even in the presence of 5% UCB+MB PL as compared to 20% UCB+MB PL. Therefore, the cells can be cultured in a lesser quantity of the UCB+MB PL, hence being economically significant.

Considering the experiments above, one can appreciate the enhanced efficacy and varied applications of UCB+MB PL over and above a simple summation of its components UCB PL and MB PL as well as over FBS.

In addition to the cell lines mentioned above, a comparative study was also performed on the three more cell lines, namely, cord tissue derived mesenchymal stem cell, bone marrow derived mesenchymal stem cell, and buccal epithelial cell. The data provided in the Tables 17-19 are with respect to culturing the cells at 20% concentration of UCB+MB PL, UCB PL, MB PL, FBS as the case may be.

TABLE 17

Cord Tissue Derived Mesenchymal Stem Cell culture with (UCB + MB) PL vs UCB PL vs MB PL vs FBS

| | | CELL COUNT (million) | CELL VIABILITY (%) | Cell characterization cell surface marker expression (%) | | | | |
|---|---|---|---|---|---|---|---|---|
| | | | | CD73 | CD90 | CD105 | CD34 | HLA-DR |
| SAMPLE 1 | PL (UCB + MB) | 5.5 | 94.23 | 98.2 | 98.6 | 98.5 | 1.2 | 1.8 |
| | UCB PL | 4.6 | 93.20 | 96.3 | 97.5 | 97.7 | 1.5 | 2.2 |
| | MB PL | 4.9 | 92.90 | 96.9 | 96.2 | 96.8 | 1.3 | 1.9 |
| | FBS | 5.2 | 93.80 | 97.4 | 97.6 | 97.9 | 1.4 | 2.8 |
| SAMPLE 2 | PL (UCB + MB) | 5.8 | 95.33 | 98.8 | 98.9 | 99.1 | 1.4 | 2.4 |
| | UCB PL | 4.7 | 94.10 | 96.9 | 96.8 | 98.2 | 2.9 | 2.8 |
| | MB PL | 4.8 | 93.11 | 97.1 | 95.4 | 96.9 | 2.3 | 2.9 |
| | FBS | 5.4 | 93.90 | 97.5 | 97.1 | 98.3 | 2.4 | 3.1 |
| SAMPLE 3 | PL (UCB + MB) | 6.2 | 96.33 | 97.9 | 96.8 | 98.6 | 2.8 | 2.7 |
| | UCB PL | 5.5 | 94.20 | 96.2 | 95.9 | 97.3 | 3.9 | 3.6 |
| | MB PL | 5.8 | 94.22 | 96.5 | 95.7 | 96.8 | 3.3 | 3.5 |
| | FBS | 5.4 | 95.23 | 97.4 | 96.1 | 97.9 | 2.7 | 3.2 |

TABLE 18

Bone Marrow Derived Mesenchymal Stem Cell culture with (UCB + MB) PL vs UCB PL vs MB PL vs FBS

| | | CELL COUNT (million) | CELL VIABILITY (%) | Cell characterization cell surface marker expression (%) | | | | |
|---|---|---|---|---|---|---|---|---|
| | | | | CD73 | CD90 | CD105 | CD34 | HLA-DR |
| SAMPLE 1 | PL (UCB + MB) | 5.9 | 97.34 | 98.1 | 97.1 | 97.9 | 2.7 | 2.9 |
| | UCB PL | 5.2 | 96.11 | 96.9 | 95.8 | 96.2 | 3.5 | 3.8 |
| | MB PL | 5.5 | 95.23 | 96.5 | 96.1 | 96.3 | 3.4 | 3.7 |
| | FBS | 5.6 | 96.13 | 97.3 | 96.6 | 97.2 | 3.2 | 3.6 |

TABLE 18-continued

Bone Marrow Derived Mesenchymal Stem Cell culture with
(UCB + MB) PL vs UCB PL vs MB PL vs FBS

|  |  | CELL COUNT (million) | CELL VIABILITY (%) | Cell characterization cell surface marker expression (%) | | | | |
|---|---|---|---|---|---|---|---|---|
|  |  |  |  | CD73 | CD90 | CD105 | CD34 | HLA-DR |
| SAMPLE 2 | PL (UCB + MB) | 5.7 | 96.34 | 97.1 | 98.1 | 97.5 | 3.1 | 3.2 |
|  | UCB PL | 4.9 | 95.11 | 96.3 | 96.6 | 96.4 | 3.9 | 3.7 |
|  | MB PL | 5.2 | 95.33 | 95.5 | 97.1 | 96.5 | 3.5 | 3.8 |
|  | FBS | 5.5 | 96.12 | 96.9 | 97.8 | 96.9 | 3.4 | 3.6 |
| SAMPLE 3 | PL (UCB + MB) | 5.5 | 96.99 | 98.5 | 97.9 | 98.1 | 3.4 | 3.6 |
|  | UCB PL | 4.8 | 96.12 | 96.8 | 96.8 | 97.8 | 3.7 | 3.8 |
|  | MB PL | 5.1 | 95.99 | 95.9 | 96.5 | 96.9 | 3.6 | 4.1 |
|  | FBS | 5.2 | 96.45 | 97.2 | 97.3 | 97.6 | 3.5 | 3.9 |

TABLE 19

Buccal Epithelial Cell culture with (UCB + MB) PL vs UCB PL vs MB PL vs FBS

|  |  | CELL COUNT (million) | CELL VIABILITY (%) | Cell characterization CK14 cell surface marker expression (%) |
|---|---|---|---|---|
| SAMPLE 1 | PL (UCB + MB) | 6.4 | 97.22 | 97.5 |
|  | UCB PL | 5.7 | 96.23 | 95.7 |
|  | MB PL | 5.6 | 95.88 | 96.1 |
|  | FBS | 5.9 | 96.88 | 96.8 |
| SAMPLE 2 | PL (UCB + MB) | 6.2 | 96.99 | 98.4 |
|  | UCB PL | 5.3 | 96.11 | 95.6 |
|  | MB PL | 5.5 | 96.20 | 96.2 |
|  | FBS | 6.0 | 96.55 | 97.3 |
| SAMPLE 3 | PL (UCB + MB) | 6.6 | 97.45 | 97.4 |
|  | UCB PL | 5.8 | 96.52 | 95.2 |
|  | MB PL | 5.9 | 96.23 | 95.8 |
|  | FBS | 6.2 | 96.77 | 96.9 |

In concurrence with the data for the earlier two cells lines, the cell viability and the number of cells as per the three cell lines of Tables 17-19 is higher for UCB+MB PL as compared to that of FBS, UCB PL, and MB PL.

Example 14

Product Safety

The acute toxicological effects and the tolerability of Autologous Adult Live Cultured Osteoblasts after single dose administration via subcutaneous route to Sprague Dawley rats for 14 days post dosing observation period was determined. This study was conducted to provide information on health hazards likely to arise from acute exposure in human beings.

Study Guidelines:
Schedule Y guideline, The Drugs and Cosmetics ($II^{nd}$ Amendment) Rules, 2005, Ministry of Health and Family Welfare, Government of India; and Sponsor's suggestions.
Guidance Document for Regulatory Approvals of Stem Cells and Cell Based Products (SCCPs) Document no.: STEM CELL AND CELL BASED PRODUCTS (SCCPs)/sps/2013-001 Version: 004 Dec. 30, 2013.
National Guidelines for Stem Cell Research (ICMR) 2017.
OECD Guidelines for the Testing of Chemicals No. 423 entitled "Acute Oral Toxicity—Acute Toxic Class Method", Adopted: 17 Dec. 2001.
Committee for the Purpose of Control and Supervision of Experiments on Animals (CPCSEA), Indian Journal of Pharmacology, 2003, 35; 257-274.

Good Laboratory Practice:
This study was performed following the OECD Principles on Good Laboratory Practice (revised 1997, issued January 1998) ENV/MC/CHEM (98) 17.

Quality Assurance:
The Quality Assurance Unit at PRADO has reviewed the draft study plan; inspected selected study specific critical phases and audited the raw data and draft report.

Materials and Methods

Details of the methods mentioned in the subsequent section of the study report are as per the relevant Standard Operating Procedures (SOPs) at PRADO.

Test Item Details

| Name of Test Item | Autologous Adult Live Cultured Osteoblasts |
|---|---|
| Sample ID | OSPCS01, OSPCS02 and OSPCS03 |
| Assay (Purity)/Cell characterization | ≥80% |
| Appearance | Suspension containing mixed precipitated pale yellow colored autologous adult live cultured Osteoblasts |
| Storage conditions | 2-8° C. |
| Handling Precautions | Standard laboratory precautions, and aseptic techniques were followed at all the times while handling the product |

Vehicle Details:

| Name of Vehicle | Cell culture medium. DMEM (Dulbecco's Modified Eagle Medium) Gibco-Thermo fisher Scientific |
|---|---|
| Appearance | Scarlet colored liquid medium |
| Storage conditions | 2-8° C. |
| Handling Precautions | Standard laboratory precautions, and aseptic techniques were followed at all the times while handling the product |

Test System Details:

| Species (Strain) | Rat (Sprague Dawley) |
|---|---|
| Sex | Male and Female Female were nulliparous and nonpregnant |

-continued

| | |
|---|---|
| Age (At the initiation of acclimatization) | Young adults between 8-12 weeks |
| Body weight (at initiation of Dosing) | Male: 205 g-250 g<br>Female: 190 g-234 g |
| Source | National Institute of Biosciences, Pune. |

Justification for Selection of Test System:

Rat was selected as a test system for this study because it is recommended by the regulatory guidelines (enumerated above) and readily available laboratory rodent species. Moreover, Sprague Dawley rats are most widely used outbred rat in biomedical research and also these are multipurpose model used for safety and efficacy testing.

Experimental Procedures

Animal Welfare:

All procedures followed during conduct of the study were in accordance with the Standard Operating Procedures of the PRADO and the guidelines set by the Committee for the Purpose of Control and Supervision of Experiments on Animals (CPCSEA) as published in The Gazette of India, Dec. 15, 1998 and an approved Institutional Animal Ethics Committee (IAEC) protocol No. (IAEC-18-069).

Husbandry Practices:

| | |
|---|---|
| Location | ARFRoom No. 02 |
| Temperature | 19.1 to 24.9° C. |
| Humidity | 35 to 69% |
| Lighting (Artificial) | Photoperiod was a sequence of 12 hrs light and dark.<br>Light hours were controlled by an automated system. |
| Air Changes | 10 to 15 air changes per hour were maintained throughout the in life phase of this study. |
| Cages | 3 animals per sex per cage were housed together in the polycarbonate cages. |
| Cage Dimensions | Approximately 410 mm × 282 mm × 152 mm |
| Feed | Standard Rat diet was provided ad libitum (Nutrivet LifeSciences, Pune). |
| Water | Reverse Osmosis water treated with UV light was provided ad libitum. |
| Analysis of feed and water | Results of periodic contaminant analysis of feed, water, as well as nutrient content analysis of feed samples were within the permissible limits. |
| Animal Identification | Animals were identified by tail marking throughout the study period. Group of animals per cage were identified by cage card information. |

Acclimatization

A total of 20 rats (10 males and 10 females) were selected and were allowed to acclimatize for a period of nine days prior to dose administration. During this period, animals were observed daily for clinical signs.

Randomization

On the last day of acclimatization period, 10 rats (5 males and 5 females) were randomly allocated for this study as Group G3. Considering the animal ethics, the data of control group was considered for this study was from PRADO/TOX-167 study.

Preparation of the Dose Formulation

Autologous Adult Live Cultured Osteoblasts were provided by the Sponsor and the culture was ready to inject directly.

Experimental Design

| Group No. | Treatment | Dose (Number of cells/ animal) | Animal Numbers Male | Female |
|---|---|---|---|---|
| G1 | Control (Vehicle)* | 0 | 01-05 | 06-10 |
| G3 | Autologous Adult Live Cultured Osteoblasts | 5 × 10$^6$ cells/0.4 ml | 21-25 | 26-30 |

Note:
*Considering animal ethics and 3Rs, the control group (G1) used for this study was from PRADO/TOX-167 study. The group number G3 and animal numbers were allotted to avoid any conflict.

Sample ID Distribution

| Group | Sample ID | Animal ID |
|---|---|---|
| G3 | Sample ID-1 (OSPCS01) | 21-22 and 26-27 |
| | Sample ID-2 (OSPCS02) | 23-24 and 28-29 |
| | Sample ID-3 (OSPCS03) | 25 and 30 |

Justification for Selection of Dose and Route of Administration

As suggested by the sponsor, the maximum feasible numbers of cells per animal were selected as a dose. The subcutaneous route of administration was selected to check the acute toxicity. Efforts have been made to select route of administration as close as possible to that proposed for clinical use.

Dose Administration

All the animals receiving Autologous Adult Live Cultured Osteoblasts were injected with 5×10$^6$ cells as a single dose which was the maximum feasible number of cells injected per animals. Control animals received vehicle supplied by the Sponsor. The dose volume for each animal was constant, i.e. 0.4 ml/animal irrespective of the body weight of the animals.

Observations

Following observations were recorded on all animals.

Mortality and Clinical Signs Observations

After subcutaneous administration of test item, all the animals were observed carefully for treatment related clinical signs, morbidity and mortality at various intervals of 10 min, 30 min, 1 hr, 2 hrs, 4 hrs and 6 hrs post dosing on first day and once daily thereafter for 14 days. The following observations were included; changes in behavior, skin, fur, eyes and mucous membranes, occurrence of secretions and excretions and basic observations of autonomic activity (e.g., lacrimation, piloerection, pupil size and unusual respiratory pattern).

Body Weight

Body weights were recorded weekly. Individual animal body weights were recorded before the test item was administered and weekly thereafter. Body weight gain was calculated for individual animal.

Clinical Pathology Observations

After completion of observation period of 14 days, all the animals were fasted overnight. The blood was collected from the retro-orbital sinus in all the animals for hematological and clinical chemistry analysis.

Hematology

For hematology analysis whole blood was collected in vials containing EDTA as an anticoagulant. Following hematological determinations were carried out using Transasia XP—100 Auto Analyzer;

| Sr. No. | Parameters | Unit |
|---|---|---|
| 1 | Total Erythrocyte Count (RBC) | $10^6/$ |
| 2 | Haematocrit (HCT) | % |
| 3 | Mean Corpuscular Volume (MCV) | fL |
| 4 | Hemoglobin Concentration (HGB) | g/dL |
| 5 | Mean Corpuscular Hemoglobin (MCH) | pg |
| 6 | Mean Corpuscular Hemoglobin Concentration (MCHC) | g/dL |
| 7 | Platelet Count (PLT) | $10^3/$ |
| 8 | Total Leukocyte Count (WBC) | $10^3/\mu L$ |

*Differential leukocyte count and Reticulocyte count were done manually.

Clinical Chemistry

Blood samples were collected in vials containing heparin as an anticoagulant and plasma was separated. Following parameters were evaluated on Transasia EM—180 Auto analyzers:

| Sr. No. | Parameter | Unit |
|---|---|---|
| 1 | Glutamate Oxaloacetate Transaminase (GOT) | U/L |
| 2 | Glutamate Pyruvate Transaminase (GPT) | U/L |
| 3 | Calculated Blood Urea Nitrogen (CBUN) | U/L |
| 4 | Creatinine (CREAT) | g/dl |
| 5 | Glucose (GLU) | mg/dl |
| 6 | Total Cholesterol (CHOLE) | mg/dl |
| 7 | Total Protein (PRO) | mg/dl |
| 8 | Albumin (ALB) | mg/dl |
| 9 | Protein: Albumin ratio (PAR) | mg/dl |
| 10 | Blood Urea Level (BUL) | mg/dl |

Necropsy and Gross Pathology

At termination of the study all the surviving animals were humanely sacrificed by carbon dioxide asphyxiation. All animals in the study were subjected to a gross necropsy and the gross pathological observations both external and internal were recorded.

Data Analysis and Interpretation of Results

All the individual raw data related to mortality, clinical signs, body weights and gross pathology was summarized in terms of groups and sex and presented in tabular format. Data was analyzed by student's t-test (unpaired) using Graph Pad Prism (Version 7.0).

Archives

All original raw data, QAU audited draft study plan, the approved study plan, the QAU reviewed draft study report and a copy of the final study report along with electronic data (DVD) files of the PDF (final study plan and final study report) will be retained for 9 years from the date of approval of final report. Thereafter, the archived material will be destroyed or stored for extended period as per the consent from the Sponsor.

Introduction

The objective of the study is to determine the acute toxicological effects and to check the tolerability of Autologous Adult Live Cultured Osteoblasts after single dose administration via subcutaneous route to Sprague Dawley rats for 14 days post dosing observation period.

Materials and Methods

Autologous Adult Live Cultured Osteoblasts cultured using UCB and MB Platelet Lysate (Source: 3 Individual Human Autologous Adult Live Cultured Osteoblasts (OSPCS01, OSPCS02 and OSPCS03) were administered subcutaneously as a single dose of $5 \times 10^6$ cells/0.4 ml/animal in a group of five male and five female rats. The animals were observed for mortality and treatment related clinical signs, if any for a period of 14 days post dosing and their body weights were recorded weekly. Necropsy and gross pathology observations were performed on all rats at termination of the study Results All the animals treated with a single dose of $5 \times 10^6$ cells/0.4 ml of Autologous Adult Live Cultured Osteoblasts survived till the scheduled necropsy. There were no abnormal clinical signs observed in any animal throughout the treatment period which could be related to the treatment of test item. Furthermore, no treatment related gross pathological alterations in any tissues or organs of the treated animals were observed at the time of necropsy on day 15.

Necropsy and Gross Pathology (Table-A and Table-B)

The detailed gross pathological examination (both external and internal) including cranial, thoracic and abdominal cavities and their contents in all treated animals did not show any lesions of pathological significance in any of the organs when compared with the control group.

Table-A: Gross pathology observations—males and females

TABLE A

| Gross Pathology Observations - Male and Female | | | | |
|---|---|---|---|---|
| Tissue/Findings/ | Males | | Females | |
| Sex Dose | 0.4 ml (Vehicle) | 0.4 ml $5 \times 10^6$ cells | 0.4 ml (Vehicle) | 0.4 ml $5 \times 10^6$ cells |
| Dose Group | G1 | G3 | G1 | G3 |
| Number Examined | 5 | 5 | 5 | 5 |
| NAD | 5 | 5 | 5 | 5 |

Key: NAD-No abnormality detected

TABLE B

| Individual Animal Gross Pathology Findings - Male | | | |
|---|---|---|---|
| | | Observations | |
| Animal No. | Organs | External | Internal |
| G1 | | Control | Dose: 0.4 ml Vehicle |
| 1 | All organs | NAD | NAD |
| 2 | All organs | NAD | NAD |
| 3 | All organs | NAD | NAD |
| 4 | All organs | NAD | NAD |
| 5 | All organs | NAD | NAD |
| G3 | | cells/0.4 ml | Dose: $5 \times 10^6$ |
| 21 | All organs | NAD | NAD |
| 22 | All organs | NAD | NAD |
| 23 | All organs | NAD | NAD |
| 24 | All organs | NAD | NAD |
| 25 | All organs | NAD | NAD |

Key: NAD- No abnormality detected.
Gross pathology included all organs of cranial, thoracic and abdominal cavities.

CONCLUSION

Based on the present study conditions and the results obtained, it can be concluded that Autologous Adult Live Cultured Osteoblasts (OSPCS01, OSPCS02 and OSPCS03) at the dose of $5 \times 10^6$ cells/0.4 ml/animal when administered via subcutaneous route was well tolerated and no treatment related adverse effects or mortality were observed.

Advantages of the Present Disclosure

The present disclosure provides a method for isolating platelets based on sedimentation methods instead of the traditionally used centrifugation methods, from the discarded human umbilical cord blood (UCB) plasma and discarded maternal blood (MB) plasma; wherein the recovery was obtained in the range of 96.29%-100%. The platelet lysate produced by said method is directed to producing non-animal source cell culture supplement as an optimized supplement as compared to FBS. Due to the human origin and processing steps of the method of the present invention, the platelet lysate so produced is xenogeneic protein free supplement. Further, the raw material used in the method of preparation in the present invention is obtained from a discarded source, for example, from a laboratory. Thus, making a cost-effective method to prepare a cell culture supplement. The platelet lysate of the present disclosure provides robustness, reliability, consistency, stability and shelf-life compared to conventionally available media supplement. The combining of human fetal source embodied in umbilical cord blood (UCB) and human adult peripheral blood embodied in maternal blood (MB) as platelet source allows for combination of proteins and growth factors that enhances the efficiency of the resultant platelet lysate. The use of maternal blood (MB), which consists of higher quantity of growth factors, proteins, hormones etc., when compared to any other adult's peripheral blood due to gestational and hemodynamic changes; which thereby makes it a potential source of selection in preparing platelet lysate. The present disclosure further advantageously identifies and provides that the umbilical cord blood and maternal blood (UCB+MB) following cryopreservation anywhere from 1 month to 12 months retains efficacy in function and is able to sustain cell viability, stability and expansion of respective cell lineage to an optimal concentration. In turn, such cell lineages obtained from such optimized formulation of the umbilical cord blood and maternal blood (UCB+MB) platelet lysate is capable of being further cryopreserved with retention of resulting cell's viability, stability and expansion post-thawing in culture for respective cell lineage to an optimal concentration. The present invention further demonstrates the advantageous use of the optimized formulation of the umbilical cord blood and maternal blood (UCB+MB) platelet lysate in various human tissue derived cells therapeutic applications, including but not limited to, mesenchymal stem cells derived from human umbilical cord tissue, osteoblasts differentiated from human bone marrow derived mesenchymal stem cells, cardiomyocytes differentiated from human umbilical cord tissue derived mesenchymal stem cells, chondrocytes from human cartilage biopsy, and buccal biopsy derived dermal fibroblasts as well as epithelial cells culture with success over and above individual sources of platelet lysates, i.e., umbilical cord blood (UCB) and/or maternal blood (MB) as well as FBS.

We claim:

1. A method for preparing a platelet lysate, said method comprising:
   a) obtaining an umbilical cord blood (UCB) sample;
   b) contacting the umbilical cord blood (UCB) sample with at least one sedimentation reagent to obtain an umbilical cord blood (UCB) sedimentation mixture;
   c) subjecting the umbilical cord blood (UCB) sedimentation mixture to at least one sedimentation to obtain an umbilical cord blood (UCB) derived platelet-rich plasma;
   d) obtaining a maternal blood (MB) sample, and subjecting the maternal blood (MB) sample to at least one sedimentation to collect maternal blood (MB) derived platelet-rich plasma;
   e) mixing the umbilical cord blood (UCB) derived platelet-rich plasma of step (c) and the maternal blood (MB) derived platelet-rich plasma of step (d) to obtain an umbilical cord blood and maternal blood (UCB+MB) platelet-rich plasma mixture;
   f) storing the umbilical cord blood and maternal blood (UCB+MB) platelet-rich plasma mixture to obtain a frozen umbilical cord blood and maternal blood (UCB+MB) platelet-rich plasma mixture; and
   g) subjecting the frozen umbilical cord blood and maternal blood (UCB+MB) platelet-rich plasma mixture to freeze-thaw cycles to obtain a lysate from a combination of umbilical cord blood derived platelets and maternal blood derived platelets.

2. The method as claimed in claim 1, wherein the lysate is selected from the group consisting of platelet lysate, cell lysate, plasma, and combinations thereof.

3. The method as claimed in claim 1, wherein the umbilical cord blood and maternal blood (UCB+MB) platelet-rich plasma mixture comprises platelets in a range of $0.3 \times 10^9$ to $1.5 \times 10^9$ platelets/ml.

4. The method as claimed in claim 1, wherein mixing of umbilical cord blood (UCB) derived platelet-rich plasma of step (c) and the maternal blood (MB) derived platelet-rich plasma of step (d) is done in a volume ratio having a range of 10:1 to 30:1.

5. The method as claimed in claim 1, wherein the freeze-thaw cycles range from 1 to 5.

6. The method as claimed in claim 1, wherein the at least one sedimentation to obtain the umbilical cord blood (UCB) derived platelet-rich plasma comprises sedimentation having a time range of at least 30 minutes each.

7. The method as claimed in claim 1, wherein subjecting the maternal blood (MB) sample to sedimentation is done for a time in a range of 50-70 minutes.

8. The method as claimed in claim 1, wherein the lysate obtained in step (g) is filtered using a 0.22µ filter.

9. The method as claimed in claim 1, wherein the lysate obtained in step (g) is subjected to screening for presence of infectious diseases (ID).

10. The method as claimed in claim 1, wherein the umbilical cord blood (UCB) sedimentation mixture comprises the umbilical cord blood (UCB) sample and the at least one sedimentation reagent is in a volume ratio of 3:1 to 9:1.

11. An umbilical cord blood and maternal blood (UCB+MB) enriched platelet lysate comprising:
   (a) a platelet lysate obtained from umbilical cord blood (UCB) derived platelet-rich plasma, said UCB derived platelet-rich plasma comprising UCB derived platelets; and
   (b) a platelet lysate obtained from maternal blood (MB) derived platelet-rich plasma, said MB derived platelet-rich plasma comprising MB derived platelets, wherein the umbilical cord blood derived platelets and the maternal blood derived platelets have a combined platelet count in a range of $0.3 \times 10^9$ to $1.5 \times 10^9$ platelets/ml.

12. The umbilical cord blood and maternal blood (UCB+MB) enriched platelet lysate as claimed in claim 11 for use in culturing cells.

13. The umbilical cord blood and maternal blood (UCB+MB) enriched platelet lysate as claimed in claim 12, wherein the cells are selected from the group consisting of progenitor cells, osteoblasts, chondrocytes, buccal epithelial cells, cord tissue-derived mesenchymal stem cells, bone marrow-derived mesenchymal stem cells, dermal culture, and cardiomyocytes.

14. The umbilical cord blood and maternal blood (UCB+MB) enriched platelet lysate as claimed in claim 11 for use in cell and tissue culture.

15. The umbilical cord blood and maternal blood (UCB+MB) enriched platelet lysate as claimed in claim 11 for use in therapeutic applications.

16. The umbilical cord blood and maternal blood (UCB+MB) enriched platelet lysate as claimed in claim 11, wherein said umbilical cord blood and maternal blood (UCB+MB) enriched platelet lysate is cryopreserved for a time in a range of 1 day to 12 months at a temperature in a range of −70° C. to −86° C. for use in culturing cells.

17. The umbilical cord blood and maternal blood (UCB+MB) enriched platelet lysate as claimed in claim 16, wherein the cells are selected from the group consisting of progenitor cells, osteoblasts, chondrocytes, buccal epithelial cells, dermal culture, cord tissue-derived mesenchymal stem cells, bone marrow-derived mesenchymal stem cells, and cardiomyocytes.

18. The umbilical cord blood and maternal blood (UCB+MB) enriched platelet lysate as claimed in claim 16 for use in therapeutic applications, and in-vitro assays.

\* \* \* \* \*